United States Patent [19]

Argenta et al.

[11] Patent Number: 5,645,081
[45] Date of Patent: *Jul. 8, 1997

[54] METHOD OF TREATING TISSUE DAMAGE AND APPARATUS FOR SAME

[75] Inventors: Louis C. Argenta, Winston-Salem; Michael J. Morykwas, Pfafftown, both of N.C.

[73] Assignee: Wake Forest University, Winston-Salem, N.C.

[*] Notice: The portion of the term of this patent subsequent to Mar. 9, 2013, has been disclaimed.

[21] Appl. No.: 792,001

[22] Filed: Nov. 14, 1991

[51] Int. Cl.$^6$ .................................. A61B 19/00
[52] U.S. Cl. .................................. 128/897; 602/42
[58] Field of Search .................... 128/897-8; 602/42-53

[56] References Cited

U.S. PATENT DOCUMENTS

| | | |
|---|---|---|
| Re. 29,319 | 7/1977 | Nordby et al. |
| 765,746 | 7/1904 | Miner. |
| 843,674 | 2/1907 | Funk. |
| 1,355,679 | 10/1920 | McConnell. |
| 1,355,846 | 10/1920 | Rannells. |
| 1,385,346 | 7/1921 | Taylor. |
| 2,232,254 | 2/1941 | Morgan. |
| 2,338,339 | 1/1944 | LaMere. |
| 2,969,057 | 1/1961 | Simmons. |
| 3,026,526 | 3/1962 | Montrose. |
| 3,026,874 | 3/1962 | Stevens. |
| 3,367,332 | 2/1968 | Groves. |
| 3,478,736 | 11/1969 | Roberts et al. |
| 3,481,326 | 12/1969 | Schamblin. |
| 3,486,504 | 12/1969 | Austin, Jr. |
| 3,610,238 | 10/1971 | Rich, Jr. |
| 3,682,180 | 8/1972 | McFarlane. |
| 3,826,254 | 7/1974 | Mellor. |
| 3,874,387 | 4/1975 | Barbieri. |
| 3,896,810 | 7/1975 | Akiyama. |
| 3,908,664 | 9/1975 | Loseff. |

(List continued on next page.)

FOREIGN PATENT DOCUMENTS

| | | |
|---|---|---|
| 561757 | 9/1932 | Germany. |
| 2809828 | 9/1978 | Germany. |
| 4111122 | 4/1993 | Germany. |
| 641061 | 8/1950 | United Kingdom. |
| 1273342 | 5/1972 | United Kingdom. |
| 9011795 | 10/1990 | WIPO .......................... A61M 27/00 |
| 9100718 | 1/1991 | WIPO. |
| WO9116030 | 10/1991 | WIPO. |
| WO9219313 | 11/1992 | WIPO. |

OTHER PUBLICATIONS

Rastgeldi, S.: I. Pressure Treatment of Peripheral Vascular Diseases. II. Intermittent Pressure Treatment of Peripheral Vascular Diseases. Opuscula Medica, Suppl. XXVII, 1972.
Junod, "Hyperemia by Suction Apparatus", Chapter VIII.
Saunders, J.W., The Lancet, pp. 1286–1287, Jun. 28, 1952, "Negative–Presure Device for Controlled Hypotension During Surgical Operations".
Landis et al., Robinette Foundation of the Hospital of the University of Pennsylvania, "The Effects of Alternate Suction and Pressure on Blood Flow to the Lower Extremeties".
Hargens et al., Space Physiology Laboratory, Life Science Division, NASA Ames Research Center, "Control of Circulatory Functions in Altered Gravitational Fields".
Wolthuis et al., Physiological Reviews, 54: 566–595, Jul. 1974, "Physiological Effects of Locally Applied Reduced Pressure in Man".

(List continued on next page.)

Primary Examiner—Angela D. Sykes
Assistant Examiner—John P. Lacyk
Attorney, Agent, or Firm—Dann Dorfman Herrell and Skillman

[57] ABSTRACT

The invention disclosed is a method of treating tissue damage comprising applying a negative pressure to a wound sufficient in time and magnitude to promote tissue migration and thus facilitate closure of the wound. The method is applicable to wounds, burns, infected wounds, and live tissue attachments. Configurations of apparatus for carrying out the method are also disclosed.

82 Claims, 1 Drawing Sheet

U.S. PATENT DOCUMENTS

| | | |
|---|---|---|
| 3,954,105 | 5/1976 | Nordby et al. |
| 3,993,080 | 11/1976 | Loseff. |
| 4,080,970 | 3/1978 | Miller. |
| 4,112,947 | 9/1978 | Nehring. |
| 4,149,541 | 4/1979 | Gammons et al. |
| 4,172,455 | 10/1979 | Beaussant. |
| 4,224,945 | 9/1980 | Cohen. |
| 4,250,882 | 2/1981 | Adair. |
| 4,261,363 | 4/1981 | Russo. |
| 4,275,721 | 6/1981 | Olson. |
| 4,297,995 | 11/1981 | Golub. |
| 4,373,519 | 2/1983 | Errede. |
| 4,382,441 | 5/1983 | Svedman. |
| 4,469,092 | 9/1984 | Marshall et al. |
| 4,525,166 | 6/1985 | Leclerc. |
| 4,540,412 | 9/1985 | Van Overloop. |
| 4,573,965 | 3/1986 | Russo. |
| 4,608,041 | 8/1986 | Nielsen. |
| 4,624,656 | 11/1986 | Clark et al. |
| 4,759,354 | 7/1988 | Quarfoot. |
| 4,764,167 | 8/1988 | Tu. |
| 4,765,316 | 8/1988 | Marshall. |
| 4,778,456 | 10/1988 | Lokken. |
| 4,820,265 | 4/1989 | DeSatnick et al. |
| 4,820,284 | 4/1989 | Hauri. |
| 4,823,110 | 4/1989 | Richard. |
| 4,836,192 | 6/1989 | Abbate. |
| 4,906,233 | 3/1990 | Moriuchi et al. |
| 4,917,112 | 4/1990 | Kalt. |
| 4,921,492 | 5/1990 | Schultz et al. |
| 4,941,882 | 7/1990 | Ward et al. |
| 4,953,565 | 9/1990 | Tachibana et al. |
| 4,969,880 | 11/1990 | Zamierowski. |
| 4,969,881 | 11/1990 | Viesturs. |
| 5,086,764 | 2/1992 | Gilman. |
| 5,106,362 | 4/1992 | Gilman. |
| 5,113,871 | 5/1992 | Viljanto. |
| 5,149,331 | 9/1992 | Ferdman. |
| 5,228,431 | 7/1993 | Giarretto. |

OTHER PUBLICATIONS

Viljanto et al., Br. J. Surg., 63: 427–430, 1976, "Local hyperalimentation of open wounds".

Dillon, Angiology—The Journal of Vascular Diseases, pp. 47–55, Jan. 1986, "Treatment of Resistant Venous Stasis Ulcers and Dermatitis with the End–Diastolid Pneumatic Compression Boot".

Lundvall et al., Acta Physiol Scand, 136: 403–409, accepted Jan. 28, 1989, "Transmission of externally applied negative pressure to the underlying tissue. A study on the upper arm of man".

Klemp et al., The Journal of Investigative Dermatology, pp. 725–726 (1989), "Subcutaneous Blood Flow in Early Male Pattern Baldness".

A. Harle, Z. Orthop., 127: 513–517 (1989), "Schwachstellen herkommlicher Drainagen".

Dunlop et al., Br. J. Surg., 77: 562–563 (1990), "Vacuum drainage of groin wounds after vascular surgery: a controlled trial".

Maddin et al., International Journal of Dermatology, 29: 446–450 (1990), "The Biological Effects of a Pulsed Electrostatic Field with Specific Reference to Hair: Electrotrichogenesis".

Nakayama et al., Ann. Plast. Surg., 26: 499–502 (1991), "A New Dressing Method for Free Skin Grafting in Hands".

Hargens et al., Aviation, Space and Environmental Medicine, pp. 934–937, Oct. 1991, "Lower Body Negative Pressure to Provide Load Bearing in Space".

Author unknown, Science, Sep. 1992, p. 42, "The Not–So–Bald–Truth".

Techno Takatsuki Co., Ltd., 8–16 Hatchonishimachi, Takatsuki City, Osaka, Japan, "HiBlow Air Pump".

Wells Johnson Company, 2045 N. Forbes Blvd., Suite 106, Tucson, AZ, "Suction Tips".

Industrial Equipment News, P.O. Box 1158, Skokie, IL 60076–9786, "Miscellaneous Equipment".

Letsou et al. "Stimulation of Adenylate Cyclase Activity in Cultured Endothelial Cells Subjected to Cyclic Stretch." Cardiovascular Surgery 3. Toronto. Sep. 1989. 634–639.

Bucalo et al. "Inhibition of Cell Proliferation by Chronic Wound Fluid." Wound Repair and Regeneration. Miami. 1993. 181–186.

Falanga, Vincent. "Growth Factors and Chronic Wounds: The Need to Understand the Microenvironment." Journal of Dermatology, vol. 19: 667–672. 1992.

Urschel et al. "The Effect of Mechanical Stress on Soft and Hard Tissue Repair; a Review." British Journal of Plastic Surgery. 41, 182–186. 1988.

Gogia, Prem P. "The Biology of Wound Healing." Ostomy/Wound Management. Nov.–Dec. 1992. pp. 12–20.

Wysocki et al. "Wound Fluid from Chronic Leg Ulcers Contains Elevated Levels of Metalloproteinases MMP–2 and MMP–9." The Society for Investigative Dermatology, Inc. Jul. 1993. 64–68.

Olenius et al. "Mitotic Activity in Expanded Human Skin." Plastic and Reconstructive Surgery. Feb. 1993. 213–215.

Aeros, "Moblvac II."

Aeros, Aeros Instruments, Inc. 1111 Lakeside Drive, Gurnee, IL 60031. Aug., 1993. "Care–E–Vac."

Emerson, Series 55. J.H. Emerson Co., 22 Cottage Park Ave., Cambridge, MA 02140. "Emerson Post–Operative Suction Pumps."

Emerson, J.H. Emerson Co., (address: same as above). "Emerson Transport Suction Unit."

Aeros, Aeros Instruments, Inc. 3411 Commercial Ave., Northbrook, IL 60062. Oct. 1988. Part No. 1504–02 7M. "Instavac Aspirator."

"Pleur–evac. Adult–Pediatric, Non–Metered." Code No.: A–4000. Control No.: F7961J.

Instruction Manual, Creative Medical Laboratories, Inc. P.O. Box 6347, Rochester, Minn. 55903. "TUGS" (Transportable Universal Gradient Suction).

Deknatel, Div. of Howmedica, Inc. Queens Village, NY 11429. "Pleur–evac."

Sparta Instrument Corp. 26602 Corporate Ave., Hayward, CA 94545. "Power Source Multi–Purpose Surgical Aspirator."

Wells Johnson Company, 2045 N. Forbes Blvd., Suite 106, Tucson, AZ. "Point 5 Aspirator."

Microtek Heritage, Inc. P.O. Box 2487, Columbus, MS 39704. "Wound–Evac ET."

Fleischmann, W. *Wund Forum Spezial.* IHW '94. "Vakuumversiegelung zur Behandlung von Problemwunden" (with English translation: Vacuum Sealing for Treatment of Problematical Wounds.

Fleischmann, W. *Acta Orthopaedica Belgica.* vol. 58, Suppl. I–1992 "Treatment of Bone and Soft Tissue Defects in Infected Nonunion."

Fleischmann, W. *Unfall Chirurg.* Springer–Variag 1993. "Vakuumversiegelung zur Behandlung des Weichteilschadens bei offenen Frakturen." (English abstract, no English translation.).

Valenta, A. *American Journal of Nursing.* Apr. 1994. "Using the Vacuum Dressing Alternative for Difficult Wounds."

Jeter, K.F. et al. (eds.), "Managing Draining Wounds and Fistulae: New and Established Methods," *Chronic Wound Care*: Health Management Publications, 1990, pp. 240–246.

Mulder, G.D. et al. (eds.), *Clinician's Pocket Guide to Chronic Wound Repair,* (Spartanburg, SC: Wound Healing Publications), 1991, pp. 54–55.

Chariker, M.E. et al. (eds.), "Effective Management of Incisional and Cutaneous Fistulae with Closed Suction Wound Drainage," *Contemporary Surgery,* vol. 34, Jun. 1989, pp. 59–63.

M. Gosta Arturson, The Pathophysiology of Severe Thermal Injury, *JBCR,* 6(2):129–146 (Mar.–Apr. 1985).

R.A.F. Clark et al., *The Molecular and Cellular Biology of Wound Repair,* Chapter 1 (1988).

METHOD OF TREATING TISSUE DAMAGE AND APPARATUS FOR SAME

FIELD OF THE INVENTION

This invention relates generally to wound healing, and more specifically is directed at wounds that are unlikely to heal completely under conventional methods.

BACKGROUND OF THE INVENTION

The treatment of open wounds that are too large to spontaneously close has been a troublesome area for many years. Wound closure requires that epithelial and subcutaneous tissue adjacent to the wound migrate toward and eventually close the wound. Some wounds are sufficiently large or infected that they are unable to close spontaneously. In such instances, a zone of stasis, an area in which localized swelling of tissues restricts the flow of blood to these tissues, forms near the surface of the wound. Without sufficient blood flow, the wound is unable to successfully fight bacterial infection and accordingly is unable to close spontaneously.

The most common technique for closure of open wounds has long been the use of sutures or staples. These mechanical closure methods provide tension on the skin tissue at the wound border that encourages epithelial tissue to migrate toward the wound and cover it. While suturing and stapling of wounds is widely practiced, it has a major drawback: the tensile force required to achieve closure with sutures or staples causes very high localized stresses at the suture insertion points, resulting in the rupture of the tissue at these points. Substantial rupture will eventually cause dehiscence in some wounds, which results in additional tissue loss. Moreover, some infected wounds harden and inflame to such a degree that closure by suturing is not feasible. Wounds not reparable by suturing or stapling generally require prolonged hospitalization, with its attendant high costs, and major surgical procedures, such as grafts of surrounding tissue. Examples of such wounds include large, deep, open wounds, pressure sores resulting from prolonged pressure, ulcers resulting from chronic osteomyelitis, and partial thickness burns that subsequently develop into full thickness burns.

To date, there has been no consistently satisfactory method for treating such wounds. What is needed is a method of closing the wound without the localized stresses that accompany suturing while at the same time treating any infection present in the wound along with a simple apparatus to carry out the method. Such a method and apparatus would reduce hospitalization and increase the probability of wound closure.

SUMMARY OF THE INVENTION

A first aspect of the invention is a method of treating tissue damage which comprises applying a negative pressure to a wound over an area sufficient to promote the migration of epithelial and subcutaneous tissue toward the wound and for a time period sufficient to facilitate closure of the wound. The method is particularly useful for treating pressure sores.

A second aspect of the invention is a method of treating a burn wound which comprises applying a negative pressure to the burn over an area and for a time sufficient to inhibit progression in the depth of the burn. The method is preferably used on a partial thickness burn soon after its infliction.

A third aspect of the invention is a method of treating tissue damage which comprises applying a negative pressure to a wound for a time sufficient to reduce bacterial density in a wound. A preferred use of this method is its application to a wound for at least 3 days to reduce the bacterial density of an infected wound to the point at which surgical closure can be attempted.

A fourth aspect of the invention is a method of enhancing the attachment of adjacent tissue to a wound which comprises applying a negative pressure to a joined complex of wound and adjacent living tissue at a sufficient magnitude and for a sufficient time to promote the migration of epithelial and subcutaneous tissue toward the complex. A preferred use of this method is enhanced attachment of adjacent tissue to tissues of the wound edges. Another use is enhanced attachment of an open skin graft.

A fifth aspect of the invention is an apparatus for facilitating the healing of wounds which comprises vacuum means for creating a negative pressure on the area of tissue surrounding the wound, sealing means operatively associated with the vacuum means to maintain the negative pressure on the wound, and screen means for preventing overgrowth of tissue in the wound area. A preferred embodiment of the invention comprises a section of open-cell foam configured to be placed over a wound, a flexible tube inserted into the foam section for attachment to a suction pump, and a flexible polymer sheet overlying the foam section and tubing and configured to be adhered to the skin surrounding the wound.

DETAILED DESCRIPTION OF THE INVENTION

Figure 1:
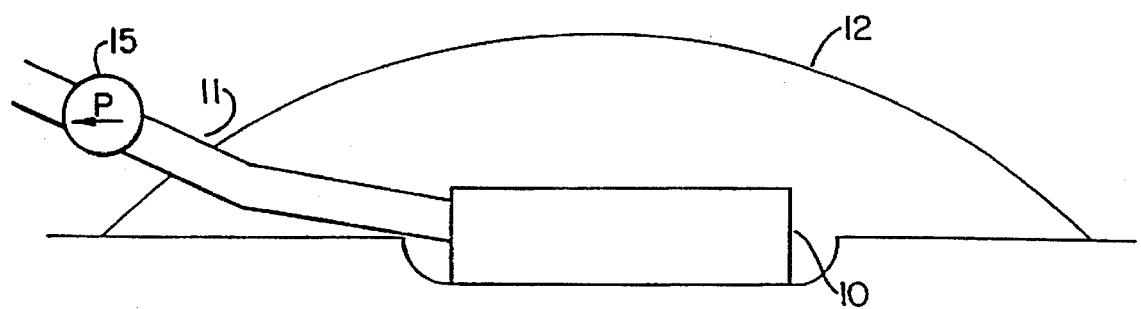
FIG. 1 shows a cross-sectional view of a negative pressure device comprising a open-cell polymer screen, a flexible hose connecting the foam section to a suction pump, and a flexible polymer sheet overlying the foam-hose assembly to provide the necessary seal.

The present invention includes a method of treating tissue damage which comprises the stages of applying a negative pressure to a wound over an area sufficient to promote migration of epithelial and subcutaneous tissue toward the wound, with the negative pressure being maintained for a time sufficient to facilitate closure of the wound. Wound closure requires that epithelial and subcutaneous tissue migrate from the wound border toward the wound. The use of negative pressure provides tension on this border tissue that causes accelerated tissue migration. It has been observed that the use of the method also causes within the wound increased formation of granulation tissue, a matrix of collagen, fibronectin, and hyaluronic acid carrying macrophages, fibroblasts, and neovasculature that aids in healing.

The method is particularly suited for use on pressure sores. A pressure sore is a wound that develops due to constant compressive pressure on the skin surface and underlying tissue. Blood flow to the compressed tissue is restricted to the extent that the overlying tissue dies and subsequently allows the underlying tissue to become infected. The decrease of blood flow to the wound prevents a normal immune reaction to fight the infection, the presence of which prevents tissue migration from the wound border.

Pressure sores often occur on bedridden patients who are unable to feel the sore or to move sufficiently to relieve the contact pressure. Such wounds can become very serious, requiring extensive and repeated skin grafts; some are even fatal. As described above, application of negative pressure to the sore permits migration of wound border tissue to occur and thus allows sores to heal without these more drastic procedures.

The method can be practiced with the application of substantially continuous negative pressure, where the pressure is relieved only to change the dressing on the wound, or it can be practiced with the use of a cyclic application of pressure in alternate periods of application and non-application. The ratio of duration of application period to non-application period can be as low as 1:10 or as high as 10:1, but is most preferably 1:1. A preferred pattern is 5 minutes of pressure application followed by 5 minutes of relief.

The method is preferably practiced using a negative pressure ranging from 0.01 to 0.99 atmospheres, and more preferably practiced using a negative pressure ranging between 0.5 to 0.8 atmospheres. The time period for use of the method on a wound is preferably at least 12 hours, but can be, for example, 1 day, 2 days, 5 days, 7 days, 14 days, 30 days, or even longer. There is no upper limit beyond which use of the method is no longer beneficial; the method increases the rate of closure up to the time the wound actually closes.

The present invention also includes a method of treating damaged tissue which comprises the steps of applying a negative pressure to a wound for a time and at a magnitude sufficient to reduce bacterial density in the wound. Open wounds are almost always contaminated with harmful bacteria. Generally a bacterial density of $10^5$ bacterial organisms per gram of tissue is regarded as infected. (It is generally accepted that at this level of infection, grafted tissue will not adhere to a wound).

These bacteria must be killed, either through the wound host's natural immune response or through some external method, before a wound will close. We have observed that application of negative pressure to a wound will reduce the bacterial density of the wound; it is believed that this effect is due to either the bacteria's incompatibility with a negative pressure environment or the increased blood flow to the wound area, as blood brings with it cells and enzymes to destroy the bacteria.

The method can be used to reduce bacterial density in a wound by at least half. More preferably, it can be used to reduce bacterial density by at least 1,000 fold. Most preferably, the method can be used to reduce bacterial density by at least 1,000,000 fold. The ranges of pressure magnitude and application duration are as described above, although Example 3 demonstrates dramatic reduction in wound contamination after a 4-day application of negative pressure. Pressure can be applied continuously or cyclically in the application/nonapplication ratios described above.

The present invention also includes a method of treating a burn which comprises the steps of applying a negative pressure to the burn over an area and for a time sufficient to inhibit formation of a full thickness burn. A partial thickness burn, one which has a surface layer of dead tissue and an underlying zone of stasis, is often sufficiently infected that it will transform within 24–48 hours into a full thickness burn, one in which all epidermal structures are destroyed. As explained above, the application of a negative pressure to the wound prevents the infection from becoming sufficiently severe to cause destruction of the underlying epidermal structures. As above, the magnitude, pattern, and duration of pressure application can vary with the individual wound.

The present invention also provides a method for enhancing the attachment of living tissue to a wound which comprises the steps of first joining the living tissue to the wound to form a wound-tissue complex, then applying a negative pressure to the wound-tissue complex over an area sufficient to promote migration of epithelial and subcutaneous tissue toward the complex, with the negative pressure being maintained for a time period sufficient to facilitate closure of the wound. Attachment of living tissue to a wound is a common procedure that can take many forms. For example, one common technique is the use of a "flap", a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure to the wound-graft complex reduces bacterial density in the complex and improves blood flow to the wound, thereby improving the attachment of the grafted tissue.

The acceptable ranges of time, magnitude, and application/non-application ratio are as described above. Each of these variables is affected by the size and type of wound.

The present invention also includes an apparatus for facilitating the healing of wounds. In general, an apparatus is provided for facilitating the healing of wounds comprising vacuum means for creating a negative pressure on the area of skin including and surrounding the wound and sealing means operatively associated with said vacuum means for maintaining said negative pressure on said wound by contacting the skin surrounding said wound. More specifically, an apparatus comprises vacuum means such as a pump for creating a negative pressure on the area of skin surrounding the wound, sealing means such as an adhesive sheet operatively associated with the vacuum means for maintaining negative pressure on the wound by contacting the skin surrounding the wound, and screen means such as an open-cell foam section located within the sealing means for preventing the overgrowth of tissue in the wound area.

The screen means is placed over substantially the expanse of the wound to prevent its overgrowth. The size and configuration of the screen can be adjusted to fit the individual wound. It can be formed from a variety of porous semi-rigid materials. The material must be sufficiently porous to allow oxygen to reach the wound, and sufficiently rigid to prevent wound overgrowth. Most preferred is the use of an open-cell polymer foam, which permits direct connection of the screen means to the vacuum means through a flexible hose inserted into the foam. Such foam can vary in thickness and rigidity, although it is preferred that a spongy material be used for the patient's comfort if the patient must lay upon the device during its operation. It can also be perforated to reduce its weight. Another embodiment comprises a section of honeycombed polyethylene sheet cut to the shape of the wound.

Possible sealing means include a flexible sealing rim contacting the skin surrounding the wound, a flexible polymer sheet overlying the screen means and the vacuum means and attached to the skin through an adhesive applied to the sheet surface facing the skin, and an inflatable sealing cuff that conforms to the skin when inflated and that is held in place by the suction of the vacuum means. If an adhesive sheet is used, it must have sufficient adhesion to remain in contact with the skin and form a seal under the negative pressure. Additionally, it must be sufficiently flexible to overlay the screen means and still conform to the skin around the wound. The sealing means also can include a semi-rigid cup that protects the wound from external contact. For example, a suitable cup-cuff assembly is provided by an adult CPR mask with an inflatable sleeve.

Suitable vacuum means includes any suction pump capable of providing at least 0.1 pound suction to the wound, and preferably up to 3 pounds suction, and most preferably up to 14 pounds suction, and a flexible hose that leads from the pump to a point within the pressurized volume created by the sealing means. The pump can be any ordinary suction pump suitable for medical purposes that is capable of providing the necessary suction. The dimension of the tubing are limited only by the pump's ability to provide the suction level needed for operation. A ¼ inch diameter tube has proven suitable. The vacuum means may operate substantially continuously, or may operate cyclically with alternate periods of application and nonapplication of pressure to the wound.

A preferred embodiment of the invention, shown in FIG. 1, comprises a substantially flat section of open cell polyester foam section 10 (Fischer Scientific, Pittsburgh, Pa. 15219) sufficiently large to cover the wound and thus prevent wound overgrowth, a flexible hollow tube 11 (Fischer Scientific) inserted into the open cell foam section 10 and joined thereto with an adhesive and extending to attach at its opposite end to a Gast Vacuum pump 15 (Fischer Scientific), and an Ioban adhesive sheet 12 (Minnesota Mining and Manufacturing, St. Paul, Minn. 55144) overlying the foam section 10 and tubing 11 and adhered to the skin surrounding the wound, thus forming a seal that allows creation of a vacuum when the suction pump operates. Such an apparatus would most preferably be packaged in a sterile condition to ameliorate the need for sterilization of the apparatus prior to use (note that the adhesive sheet 12 could be packaged separately from the foam-tube assembly). A particular advantage of this configuration is its use with pressure sores: the device can be placed in the depths of the wound and the patient can lie upon it without either affecting the utility of the device or further damaging the wound. This becomes critical if the patient cannot be moved from this posture for other medical reasons.

The present invention is explained further in the following examples. These examples are provided for illustrative purposes only and are not to be taken as limiting.

EXAMPLE 1

Rate of Wound Healing under Negative Pressure

This example demonstrates the use of negative pressure to increase the rate of healing of full thickness defects by increasing vascularity and the amount of granulation tissue present.

Figure 2:
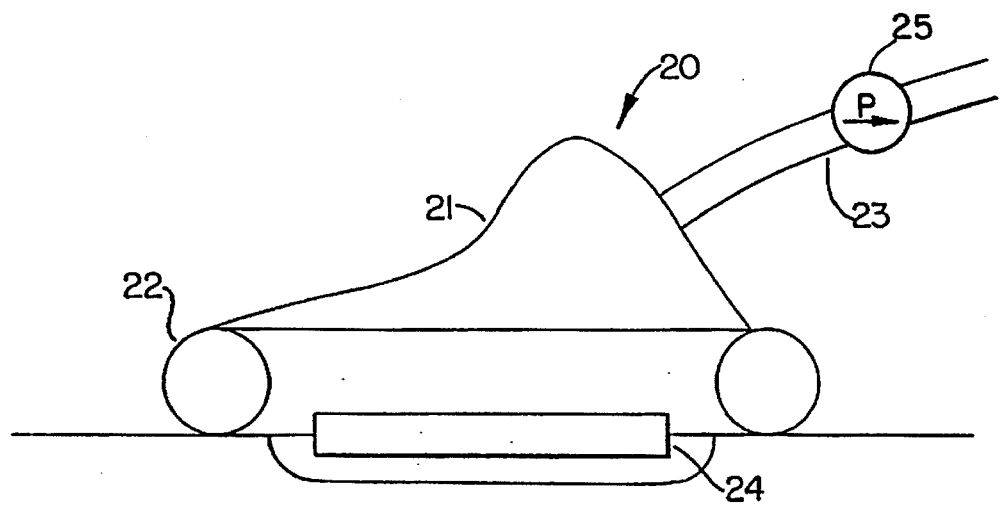
FIG. 2 shows a cross-sectional view of a negative pressure device comprising a porous screen, an inflatable cuff attached to a semi-rigid cup, and a flexible hose extending from a suction pump to a point within the sealed volume of the cup-cuff assembly.

Fifteen-kilogram pigs were obtained and conditioned for 1 week prior to use. The backs of the pigs were shaved and scrubbed for surgery. Two full thickness circular defects were created on the midline of the animals, 2.5 cm in diameter and 1 cm thick. Alginate impressions were taken of each defect to determine its volume. Cefazolin (Kefzol) (500 mg) was administered intramuscularly (antibiotic). The suction devices used, shown in FIG. 2, comprised an adult CPR mask 20 (Doug Brown and Associates, Huntington Beach, Calif. 92648) comprising a semi-rigid cup 21 and inflatable cuff 22 in contact with the skin, an open cell polyester screen 24 overlying the wound, and a flexible ¼ inch diameter hose 23 (Fischer Scientific) connected by a Nalgene tubing connector to a vacuum pump 25 (Fischer Scientific) and extending through a sealed hole in the cup. Each device was configured such that the suction hose ran from the cup on the animal up through a pulley suspended over the center of the pen and down to a vacuum trap bottle to collect any liquid exudate, then down to the vacuum pump. A suction device was attached over each defect, and suction (2–6 pounds vacuum) was applied to one of the devices. The devices were removed only so that impressions could be made of each defect. This procedure was continued until the volume of both defects was zero.

Table 1 shows data expressed as the amount of granulation tissue formed per day and as the percent difference in rate of granulation tissue formation. The data shows that in all cases the use of negative pressure increased the rate of wound closure and the formation of granulation tissue at a statistically significant rate.

EXAMPLE 2

Rate of Burn Healing under Negative pressure

This example was designed to demonstrate the use of continuous closed suction for the treatment of deep, partial thickness thermal burns (second degree burns).

The backs of 15 kg pigs were shaved and scrubbed for surgery. A 1.5 inch diameter brass rod was heated to 190° C. in an oil bath. The rod was pressed onto the pig's skin for 15 seconds following a well-known technique of relating depth of burn to time and temperature. Three burns were created over the spine of each pig, separated by 5 cm intervals. Suction apparatus cups of the configuration described above were placed over two of the burns, with silver sulphadiazine (Silvadine) cream, the standard antibiotic cream applied to human burns prior to excision of burned tissue, applied to the third. Cefazolin (Kefzol) (500 mg) was administered intramuscularly (antibiotic). Suction (2–6 pounds vacuum) was applied to one of the cups. A small (2 mm) punch biopsy was taken of the wounded area and examined histologically for depth of burn.

TABLE 1

Rate of granulation tissue formation for control and reduced pressure treated full thickness defects in pigs.

| Animal | Granulated Treatment | Tissue/Day(cc) | % Increase* |
|---|---|---|---|
| 1 | Suction | 0.48 | 26.3 |
|   | Control | 0.38 |  |
| 2 | Suction | 1.16 | 28.9 |
|   | Control | 0.90 |  |
| 3 | Suction | 0.58 | 75.8 |
|   | Control | 0.33 |  |
| 4 | Suction | 0.71 | 65.1 |
|   | Control | 0.43 |  |
| 5 | Suction | 0.71 | 65.1 |
|   | Control | 0.43 |  |

*(Suction−Control)/Control

TABLE 2

Rate of reduction in bacterial density for control and reduce and pressure treated pigs (n = 5).

Log Organisms Per Gram Tissue

| Treatment | | Day 0 | Day 1 | Day 2 | Day 3 | Day 4 | Day 5 | Day 7 |
|---|---|---|---|---|---|---|---|---|
| Control | Mean | 8.44 | 8.04 | 8.17 | 7.13 | 7.13 | 8.82 | 7.08 |
|  | SD | +.38 | ±.13 | ±.98 | ±.15 | ±.24 | ±1.12 | ±.52 |
| Vacuum | Mean | 7.69 | 7.36 | 7.37 | 6.79 | 6.43 | 3.98 | 4.32 |
|  | SD | ±.83 | ±.84 | ±1.40 | ±.55 | ±.45 | ±3.46 | ±3.74 |

Biopsies were analyzed by a dermatopathologist who was not told the nature of the study. It was concluded that the suctioned tissue specimens were healthier and healing more quickly than non-suctioned specimens.

EXAMPLE 3

Reduction of Bacterial Density under Negative Pressure

This example illustrates the effects of continuous closed suction on the bacterial density of infected tissue.

Fifteen-kilogram pigs were shaved and prepared for surgery. Two 2.5 cm diameter defects were created on the dorsum of each pig using sterile technique, with a 7.5 cm interval retained between the edges of the defects. Hemostasis was obtained by electrocautery. One ml of culture broth containing $10^8$ Staph. aureus organisms was injected just beneath the surface tissue in the center of each wound. Suction cups of the configuration described above were placed over each defect, and a T-shirt was placed over the animal. Suction (2–6 pounds vacuum) was applied 24 hours after surgery to only one of the defects, allowing each animal to act as its own control. No antibiotics were given during the course of the study.

Each day, a small (3 mm biopsy punch) piece of granulation tissue was removed from the center of each defect. The number of organisms present in the tissue was determined by weighing the tissue, homogenizing the tissue, serially diluting the supernatant, and plating the diluted supernatant on blood agar plates. Samples of the original broth were treated in an identical manner to determine effects of mechanical manipulations on bacteria viability. The procedure was performed until the wounds were healed.

Table 2 compares the bacterial density of treated wounds and control wounds over time. The data is expressed as the mean log of the number of viable organisms per gram of tissue as a function of time. Clearly, the application of negative pressure increases the rate at which bacteria are destroyed. Using $10^5$ organisms per gram of tissue as a baseline for infection, the data show that on average a suctioned wound was disinfected after 4 days of treatment, while the average non-treated wound was still infected after 7 days.

EXAMPLE 4

Treatment of Pressure Sore With Negative Pressure

Mr. L. J. is a 45-year-old diabetic male who has been a paraplegic as the result of a gunshot wound for 12 years. He has a history of recurrent right ischeal fossa pressure sore and right trochanteric pressure ulcer. L. J. was admitted to the hospital for treatment and closure of the pressure sores. A flap was placed onto the wound and secured with sutures and staples.

The incisions of the flap dehisced, resulting in a large, open wound. The tissues of the flap were very edematous and indurated. Nine days after the flap was detached, a negative pressure device was placed over the wound. The device comprised an open-cell polyester foam section (Fischer Scientific) approximately ½ inch in thickness attached to a suction pump by a flexible hose (Fischer Scientific) and covered and sealed by Ioban polymer sheet (Minnesota Mining and Manufacturing, St. Paul, Minn. 55144). A continuous vacuum of 5 psi was applied to the wound. The design of the device allowed the patient to lay comfortably on the device during operation.

The depth of the wound decreased dramatically. The devices were changed and the wound examined on a three times per week basis. Reduced pressure treatment was continued for 6 weeks, at which time the wound was healed.

EXAMPLE 5

Treatment of Pressure Sore With Negative Pressure

Mr. W. E. is a 51-year-old male who had both legs amputated at the hip approximately 20 years ago. He was afflicted with a large pressure sore in the buttocks region. The pressure sore had been present 7 months and measured 8 inches laterally and 3 in its greatest width. An open cell foam reduced pressure device as described in Example 4 was placed over the wound and a negative pressure of 5 psi was applied cyclically in alternate periods of 5 minutes on, 5 minutes off. The open cell foam device was used as the patient was lying on the device. The device was changed on a three times per week schedule.

After 5 weeks of treatment, the wound measured 3 inches laterally and 1.5 inches at its greatest width. At that point the wound was essentially healthy granulation tissue that accepted a cultured keratinocyte allograft and healed completely.

EXAMPLE 6

Treatment of Wound Dehiscence With Negative Pressure

Mr. C. L. is a 50-year-old male who had undergone a colostomy revision through a midline laparotomy. He was readmitted to the hospital for wound dehiscence and evisceration following forceful coughing. The abdominal wall was closed with Prolene mesh coverage. Six weeks after placement of the Prolene mesh, the wound was still open and measured 28 cm by 23 cm with sparse granulation tissue grown through the Prolene mesh. A large reduced pressure cup device of the type described in Example 1 with an underlying porous Aquaplast sheet (WFR/Aquaplast Corp., Wyckoff, N.J. 07481) was placed on the Prolene mesh/ wound surface and the space closed with a tent of Ioban. Five psi of continuous negative pressure was applied. The device was changed three times per week.

After 6 days, granulation tissue had grown through the Prolene mesh, totally covering the mesh. The patient was taken to the operating room where the surrounding tissue was undermined and grafted onto the wound to partially close the defect. Split thickness skin grafts were used to cover the remainder of the defect, and were placed on the bed of granulation tissue. The wound accepted 80% of the grafts, and the remaining areas closed with dressing changes alone.

EXAMPLE 7

Treatment of Ankle Osteomyelitic Ulcer With Negative Pressure

Mr. R. F. is a 39-year-old white male who had severe trauma to his left lower extremity secondary to a motor vehicle accident 10 years ago. He had contracted chronic osteomyelitis and an open ulcer with exposed bone of his left lateral ankle (lateral malleolar ulcer). Necrotic soft tissue and bone were surgically removed from the ankle. The patient was placed on a 2½ week course of antibiotics. The day after surgery, a reduced pressure device of the type described in Example 1 was placed over the wound, and a negative pressure of 5 psi was applied. The device was changed on a three times per week schedule. After 14 days of treatment, the wound was smaller and filled with granulation tissue. A split thickness skin graft was placed over the center of the defect and healed primarily.

EXAMPLE 8

Treatment of Burn With Negative Pressure

Patient B. is admitted with second and third degree burns over the face and upper extremities, including both hands, as a result of a house fire. A large mitten-shaped reduced pressure device of the type described in Example 4 is placed over the patient's right hand, with open cell foam inserts placed between the fingers to apply reduced pressure to the interdigit spaces. Three pounds of vacuum is applied cyclically in a pattern of 5 minutes on, 5 minutes off. The device is changed on a three times per week schedule. Treatment is continued until the necrotic tissue sloughs off or is excised, followed by split thickness skin graft placement.

The foregoing examples are illustrative of the present invention, and are not to be construed as limiting thereof. The invention is defined by the following claims, with equivalents of the claims to be included therein.

That which is claimed is:

1. An apparatus for facilitating the healing of wounds, comprising:
   vacuum means for creating a negative pressure between about 0.1 and 0.99 atmospheres on the area of skin including and surrounding the wound;
   sealing means operatively associated with said vacuum means for maintaining said negative pressure on said wound by contacting the skin surrounding said wound; and
   screen means for positioning at the wound within the sealing means for preventing the overgrowth of tissue in the wound.

2. An apparatus according to claim 1, in which said screen means comprises an open-cell polymer foam.

3. An apparatus according to claim 1, in which said screen means comprises a flat, porous, semi-rigid member.

4. An apparatus according to claim 1, in which said sealing means includes a flexible sealing rim in contact with said skin surrounding said wound.

5. An apparatus according to claim 1, in which said sealing means includes a flexible polymer sheet overlying said screen means, said polymer sheet having adhesive on at least a surface facing the wound to attach and seal said polymer sheet to said surrounding skin.

6. An apparatus according to claim 1, in which said sealing means includes a sealing cuff in contact with said skin surrounding the wound.

7. An apparatus according to claim 6, in which said sealing cuff is inflatable.

8. An apparatus according to claim 1, in which said vacuum means includes pump means for providing at least 0.1 pounds suction.

9. An apparatus according to claim 1, in which said vacuum means includes a pump means for providing at least 3 pounds suction.

10. An apparatus according to claim 1, in which said vacuum means includes a pump means for providing at least 14 pounds suction.

11. An apparatus according to claim 1, in which said vacuum means operates continuously.

12. An apparatus according to claim 1, in which said vacuum means operates cyclically to provide periods of application and non-application of suction.

13. An apparatus according to claim 1 wherein said vacuum means supplies a negative pressure between about 0.3 and 0.99 atmospheres to the wound.

14. An apparatus according to claim 1 wherein said vacuum means supplies a negative pressure between about 0.5 and 0.99 atmospheres to the wound.

15. An apparatus according to claim 1 wherein said vacuum means supplies a negative pressure between about 0.5 and 0.8 atmospheres to the wound.

16. An apparatus for facilitating the healing of wounds, comprising:
   vacuum means for creating a negative pressure on the area of skin including and surrounding the wound;
   sealing means operatively associated with said vacuum means for maintaining said negative pressure on said wound by contacting the skin surrounding said wound, wherein said sealing means includes a semi-rigid cup configured to protect said wound from external contact; and
   screen means for positioning at the wound within the sealing means for preventing the overgrowth of tissue in the wound.

17. An apparatus for applying negative pressure to a wound beneath a fluid-impermeable seal comprising:
   an open cell polymer foam section for positioning beneath said seal configured to overlie the wound such that said negative pressure is maintained within said foam and applied to the wound; and
   a flexible tube having an inlet end inserted into said open cell polymer foam section and an outlet end for extending from beneath said seal and for supplying said negative pressure; and
   wherein said apparatus is in an aseptic package.

18. An apparatus for treating a wound, comprising:
   an open-cell foam section configured to overlie the wound;
   a fluid-impermeable cover overlying said foam section, said cover adapted to form a seal with skin surrounding the wound for maintaining negative pressure beneath said cover; and a single tubular member having a first end inserted beneath at least a portion of the foam section and having a second end extending from beneath said cover to a location external to said cover for supplying negative pressure beneath the cover.

19. The apparatus of claim 18 wherein said open-cell foam section is configured to overlie only a region of said wound within the margin of said wound.

20. The apparatus of claim 18 wherein said first end of the tubular member is embedded within the foam section.

21. An apparatus according to claim 18 wherein said vacuum source supplies a negative pressure between about 0.3 and 0.99 atmospheres to the wound.

22. An apparatus according to claim 18 wherein said vacuum source supplies a negative pressure between about 0.5 and 0.99 atmospheres to the wound.

23. An apparatus according to claim 18 wherein said vacuum source supplies a negative pressure between about 0.5 and 0.8 atmospheres to the wound.

24. An apparatus for treating a wound, comprising:
a semi-rigid, fluid-impermeable cup for positioning over the wound and for maintaining a negative pressure upon said wound, said cup having only a single external fluid communication port;
sealing means for sealing said cup about the wound, said sealing means including a cuff for inflating and conforming to the surrounding skin to seal said cup in place by said negative pressure;
tubular means extending from said fluid communication port of said cup for supplying said negative pressure; and
screen means for positioning beneath the cup at the wound for preventing overgrowth of the wound.

25. The apparatus of claim 24 wherein said screen means is a porous sheet.

26. The apparatus of claim 24 wherein said screen means is an open-cell foam.

27. An apparatus for facilitating the healing of wounds, comprising:
vacuum means for creating a negative pressure on the area of skin including and surrounding the wound, wherein said vacuum means operates cyclically to provide periods of application and non-application of suction with the ratio of duration of application period to non-application period between about 1:10 and 10:1;
sealing means operatively associated with said vacuum means for maintaining said negative pressure on said wound by contacting the skin surrounding said wound; and
screen means for positioning at the wound within the sealing means for preventing the overgrowth of tissue in the wound.

28. An apparatus according to claim 27 in which the duration of said application period is about 5 minutes.

29. An apparatus according to claim 28 in which the duration of said non-application period is about 5 minutes.

30. An apparatus according to claim 23, in which said screen means comprises an open-cell polymer foam.

31. An apparatus according to claim 24, in which said screen means comprises a flat, porous, semi-rigid member.

32. An apparatus according to claim 27, in which said sealing means includes a flexible sealing rim in contact with said skin surrounding said wound.

33. An apparatus according to claim 27, in which said sealing means includes a flexible polymer sheet overlying said screen means, said polymer sheet having adhesive on at least a surface facing the wound to attach and seal said polymer sheet to said surrounding skin.

34. An apparatus according to claim 27, in which said sealing means includes a sealing cuff in contact with said skin surrounding the wound.

35. An apparatus according to claim 34, in which said sealing cuff is inflatable.

36. An apparatus according to claim 27, in which said vacuum means includes pump means for providing at least 0.1 pounds suction.

37. An apparatus according to claim 27, in which said vacuum means includes a pump means for providing at least 3 pounds suction.

38. An apparatus according to claim 27, in which said vacuum means includes a pump means for providing at least 14 pounds suction.

39. An apparatus for facilitating the healing of wounds, comprising:
vacuum means for creating a negative pressure on the area of skin including and surrounding the wound;
sealing means operatively associated with said vacuum means for maintaining said negative pressure on said wound by contacting the skin surrounding said wound, wherein said sealing means comprises a fluid-impermeable cover; and
screen means for positioning at the wound within the sealing means for preventing the overgrowth of tissue in the wound.

40. An apparatus according to claim 39, in which said screen means comprises an open-cell polymer foam.

41. An apparatus according to claim 39, in which said screen means comprises a flat, porous, semi-rigid member.

42. An apparatus according to claim 39, in which said sealing means includes a flexible sealing rim in contact with said skin surrounding said wound.

43. An apparatus according to claim 39, in which said cover includes a flexible polymer sheet overlying said screen means, said polymer sheet having adhesive on at least a surface facing the wound to attach and seal said polymer sheet to said surrounding skin.

44. An apparatus according to claim 39, in which said sealing means includes a sealing cuff in contact with said skin surrounding the wound.

45. An apparatus according to claim 44, in which said sealing cuff is inflatable.

46. An apparatus according to claim 39, in which said vacuum means includes pump means for providing at least 0.1 pounds suction.

47. An apparatus according to claim 39, in which said vacuum means includes a pump means for providing at least 3 pounds suction.

48. An apparatus according to claim 39, in which said vacuum means includes a pump means for providing at least 14 pounds suction.

49. An apparatus according to claim 39, in which said vacuum means operates continuously.

50. An apparatus according to claim 39, in which said vacuum means operates cyclically to provide periods of application and non-application of suction.

51. An apparatus according to claim 50 in which said vacuum means provides periods of application and non-application of suction with the ratio of duration of application period to non-application period between about 1:10 and 10:1.

52. An apparatus according to claim 51 in which the duration of said application period is about 5 minutes.

53. An apparatus according to claim 52 in which the duration of said non-application period is about 5 minutes.

54. An apparatus for facilitating the healing of wounds, comprising:

vacuum means for creating a negative pressure on the area of skin including and surrounding the wound;

sealing means operatively associated with said vacuum means for maintaining said negative pressure on said wound by contacting the skin surrounding said wound; and screen means for positioning at the wound within the sealing means, said screen means having a pore size sufficiently large to prevent the overgrowth of tissue in the wound.

55. An apparatus according to claim 54, in which said screen means comprises an open-cell polymer foam.

56. An apparatus according to claim 54, in which said screen means comprises a flat, porous, semi-rigid member.

57. An apparatus according to claim 54, in which said sealing means includes a flexible sealing rim in contact with said skin surrounding said wound.

58. An apparatus according to claim 54, in which said cover includes a flexible polymer sheet overlying said screen means, said polymer sheet having adhesive on at least a surface facing the wound to attach and seal said polymer sheet to said surrounding skin.

59. An apparatus according to claim 54, in which said sealing means includes a sealing cuff in contact with said skin surrounding the wound.

60. An apparatus according to claim 59, in which said sealing cuff is inflatable.

61. An apparatus according to claim 54, in which said vacuum means includes pump means for providing at least 0.1 pounds suction.

62. An apparatus according to claim 54, in which said vacuum means includes a pump means for providing at least 3 pounds suction.

63. An apparatus according to claim 54, in which said vacuum means includes a pump means for providing at least 14 pounds suction.

64. An apparatus according to claim 54, in which said vacuum means operates continuously.

65. An apparatus according to claim 54, in which said vacuum means operates cyclically to provide periods of application and non-application of suction.

66. An apparatus according to claim 65, in which said vacuum means operates cyclically to provide periods of application and non-application of suction with the ratio of duration of application period to non-application period between about 1:10 and 10:1.

67. An apparatus according to claim 66 in which the duration of said application period is about 5 minutes.

68. An apparatus according to claim 67 in which the duration of said non-application period is about 5 minutes.

69. An apparatus for treating a wound comprising:

an open-cell foam section configured to overlie the wound;

a cover overlying said foam section, said cover adapted to form a seal with skin surrounding the wound for maintaining a negative pressure beneath said cover;

a single tubular member having a first end inserted beneath at least a portion of the foam section and having a second end extending from beneath said cover to a location external to said cover; and a vacuum source connected with the second end of the tubular member for supplying said negative pressure between about 0.1 and 0.99 atmospheres to the wound.

70. An apparatus according to claim 69 wherein said vacuum source supplies a negative pressure between about 0.3 and 0.99 atmospheres to the wound.

71. An apparatus according to claim 69 wherein said vacuum source supplies a negative pressure between about 0.5 and 0.99 atmospheres to the wound.

72. An apparatus according to claim 69 wherein said vacuum source supplies a negative pressure between about 0.5 and 0.8 atmospheres to the wound.

73. An apparatus according to claim 69 wherein said open-cell foam section is configured to overlie only a region of said wound within the margin of said wound.

74. An apparatus according to claim 69 wherein said first end of the tubular member is embedded within the foam section.

75. An apparatus for treating a wound comprising:

an open-cell foam section configured to overlie the wound, said foam section having a pore size sufficiently large to prevent overgrowth of the wound;

a cover overlying said foam section, said cover adapted to form a seal with skin surrounding the wound for maintaining a negative pressure beneath said cover; and a single tubular member having a first end inserted beneath at least a portion of the foam section and having a second end extending from beneath said cover to a location external to said cover for supplying said negative pressure beneath the cover.

76. An apparatus according to claim 75 wherein said open-cell foam section is configured to overlie only a region of said wound within the margin of said wound.

77. An apparatus according to claim 75 wherein said first end of the tubular member is embedded within the foam section.

78. An apparatus for treating a wound comprising:

an open-cell foam section configured to overlie the wound;

a cover overlying said foam section, said cover adapted to form a seal with skin surrounding the wound for maintaining a negative pressure beneath said cover;

a single tubular member having a first end inserted beneath at least a portion of the foam section and having a second end extending from beneath said cover to a location external to said cover; and a vacuum source for supplying a negative pressure on the area of skin including and surrounding the wound, wherein said vacuum source operates cyclically to provide periods of application and non-application of suction with the ratio of duration of application period to non-application period between about 1:10 and 10:1.

79. An apparatus according to claim 78 in which the duration of said application period is about 5 minutes.

80. An apparatus according to claim 79 in which the duration of said non-application period is about 5 minutes.

81. An apparatus according to claim 78 wherein said open-cell foam section is configured to overlie only a region of said wound within the margin of said wound.

82. An apparatus according to claim 78 wherein said first end of the tubular member is embedded within the foam section.

* * * * *

UNITED STATES PATENT AND TRADEMARK OFFICE
CERTIFICATE OF CORRECTION

PATENT NO. : 5,645,081 Page 1 of 1
APPLICATION NO. : 07/792001
DATED : July 8, 1997
INVENTOR(S) : Argenta et al.

It is certified that error appears in the above-identified patent and that said Letters Patent is hereby corrected as shown below:

Front page, [*] Notice "March 9, 2013"
      should read -- June 10, 2014 --

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 5,645,081 |
| APPLICATION NO. | : 07/792001 |
| DATED | : July 8, 1997 |
| INVENTOR(S) | : Louis C. Argenta and Michael J. Morykwas |

It is certified that error appears in the above-identified patent and that said Letters Patent is hereby corrected as shown below:

Claim 30, line 1, the numeral "23", should read --27--.

Claim 31, line 1, the numeral "24", should read --27--.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,645,081 | Page 1 of 1 |
| APPLICATION NO. | : 07/792001 | |
| DATED | : July 8, 1997 | |
| INVENTOR(S) | : Louis C. Argenta and Michael J. Morykwas | |

It is certified that error appears in the above-identified patent and that said Letters Patent is hereby corrected as shown below:

Column 11, Claim 30, line 1, the numeral "23", should read --27--.

Column 11, Claim 31, line 1, the numeral "24", should read --27--.

This certificate supersedes the Certificate of Correction issued August 19, 2008.

Signed and Sealed this

Sixteenth Day of September, 2008

JON W. DUDAS
*Director of the United States Patent and Trademark Office*

US005645081C1

(12) EX PARTE REEXAMINATION CERTIFICATE (7129th)
United States Patent
Argenta et al.

(10) Number: US 5,645,081 C1
(45) Certificate Issued: Nov. 3, 2009

(54) METHOD OF TREATING TISSUE DAMAGE AND APPARATUS FOR SAME

(75) Inventors: Louis C. Argenta, Winston-Salem, NC (US); Michael J. Morykwas, Pfafftown, NC (US)

(73) Assignee: Wake Forest University Health Sciences, Winston-Salem, NC (US)

Reexamination Request:
No. 90/008,692, Jun. 11, 2007
No. 90/010,186, Jun. 3, 2008

Reexamination Certificate for:
Patent No.: 5,645,081
Issued: Jul. 8, 1997
Appl. No.: 07/792,001
Filed: Nov. 14, 1991

Certificate of Correction issued Nov. 14, 2006.

Certificate of Correction issued Aug. 19, 2008.

Certificate of Correction issued Sep. 16, 2008.

(51) Int. Cl.
*A61B 19/00* (2006.01)

(52) U.S. Cl. .......................................... 128/897; 602/42
(58) Field of Classification Search ........................ None
See application file for complete search history.

(56) References Cited

U.S. PATENT DOCUMENTS

| | | |
|---|---|---|
| 765,746 A | 7/1904 | Miner |
| 774,529 A | 11/1904 | Nieschang |
| 843,674 A | 2/1907 | Funk |
| 1,000,001 A | 8/1911 | Holz |
| 1,355,679 A | 10/1920 | McConnell |
| 1,355,846 A | 10/1920 | Rannells |
| 1,385,346 A | 7/1921 | Taylor |
| 1,936,129 A | 11/1933 | Fisk |
| 2,025,492 A | 12/1935 | Aird |
| 2,122,121 A | 6/1938 | Tillotson |
| 2,195,771 A | 4/1940 | Estler |
| 2,221,758 A | 11/1940 | Elmquist |
| 2,232,254 A | 2/1941 | Morgan |
| 2,280,915 A | 4/1942 | Johnson |
| 2,338,339 A | 1/1944 | LaMere |
| 2,443,481 A | 6/1948 | Sene |
| 2,547,758 A | 4/1951 | Keeling |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 2,969,057 A | 1/1961 | Simmons |
| 3,026,526 A | 3/1962 | Montrose |
| 3,026,874 A | 3/1962 | Stevens |
| 3,042,041 A | 7/1962 | Jascalevich |
| 3,115,138 A | 12/1963 | McElvenny |
| 3,115,318 A | 12/1963 | Caillette |
| 3,315,665 A | 4/1967 | Macleod |
| 3,324,855 A | 6/1967 | Heimlich |
| 3,367,332 A | 2/1968 | Groves |

(Continued)

FOREIGN PATENT DOCUMENTS

| | | |
|---|---|---|
| DE | 561757 | 10/1932 |
| DE | 847475 | 6/1952 |
| DE | 847475 | 8/1952 |

(Continued)

OTHER PUBLICATIONS

K. F. Jeter, T.E. Tintle and M. Chariker, "Managing Draining Wounds and Fistulae: New and Established Methods," in Chronic Wound Care, Edited by D. Krasner, pp. 240–246.*

(Continued)

*Primary Examiner*—Beverly M. Flanagan

(57) ABSTRACT

The invention disclosed is a method of treating tissue damage comprising applying a negative pressure to a wound sufficient in time and magnitude to promote tissue migration and thus facilitate closure of the wound. The method is applicable to wounds, burns, infected wounds, and live tissue attachments. Configurations of apparatus for carrying out the method are also disclosed.

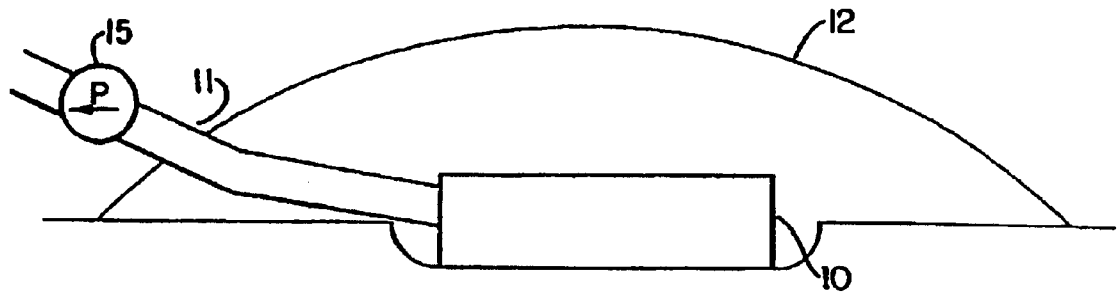

U.S. PATENT DOCUMENTS

| | | | |
|---|---|---|---|
| 3,382,867 A | 5/1968 | Reaves |
| 3,429,313 A | 2/1969 | Romanelli |
| 3,478,736 A | 11/1969 | Roberts et al. |
| 3,481,326 A | 12/1969 | Schamblin |
| 3,486,504 A | 12/1969 | Austin, Jr. |
| 3,520,300 A | 7/1970 | Flower et al. |
| 3,528,416 A | 9/1970 | Chamberlain |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,713,622 A | 1/1973 | Dinger |
| 3,753,439 A | 8/1973 | Brugarolas et al. |
| 3,782,377 A | 1/1974 | Rychlik |
| 3,812,972 A | 5/1974 | Rosenblum |
| 3,814,095 A | 6/1974 | Lubens |
| 3,826,254 A | 7/1974 | Mellor |
| 3,874,387 A | 4/1975 | Barbieri |
| 3,896,810 A | 7/1975 | Akiyama |
| 3,903,882 A | 9/1975 | Augurt |
| 3,908,664 A | 9/1975 | Loseff |
| 3,935,863 A | 2/1976 | Kliger |
| 3,938,540 A | 2/1976 | Holbrook et al. |
| 3,954,105 A | 5/1976 | Nordby et al. |
| 3,976,060 A | 8/1976 | Hildebrandt |
| 3,978,855 A | 9/1976 | McRae |
| 3,993,080 A | 11/1976 | Loseff |
| 3,998,227 A | 12/1976 | Holbrook et al. |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,156,066 A | 5/1979 | Gould |
| 4,157,715 A | 6/1979 | Westerhoff |
| 4,169,563 A | 10/1979 | Leu |
| 4,172,455 A | 10/1979 | Beaussant |
| 4,184,510 A | 1/1980 | Murry et al. |
| 4,191,204 A | 3/1980 | Nehring |
| 4,221,215 A | 9/1980 | Mandelbaum |
| 4,224,941 A | 9/1980 | Stivala |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,392,853 A | 7/1983 | Muto |
| 4,399,816 A | 8/1983 | Spangler |
| 4,419,097 A | 12/1983 | Rowland |
| 4,452,845 A | 6/1984 | Lloyd et al. |
| 4,457,755 A | 7/1984 | Wilson |
| 4,459,139 A | 7/1984 | vonReis et al. |
| 4,465,062 A | 8/1984 | Versaggi et al. |
| 4,465,485 A | 8/1984 | Kashmer et al. |
| 4,469,092 A | 9/1984 | Marshall et al. |
| 4,475,909 A | 10/1984 | Eisenberg |
| 4,480,638 A | 11/1984 | Schmid |
| RE31,887 E | 5/1985 | Hodgson |
| 4,525,166 A | 6/1985 | Leclerc |
| 4,527,064 A | 7/1985 | Anderson |
| 4,533,352 A | 8/1985 | Van Beek |
| 4,540,412 A | 9/1985 | Van Overloop |
| 4,543,100 A | 9/1985 | Brodsky |
| 4,553,967 A | 11/1985 | Ferguson |
| 4,569,674 A | 2/1986 | Phillips et al. |
| 4,573,965 A | 3/1986 | Russo |
| 4,576,158 A | 3/1986 | Boland |
| 4,579,555 A | 4/1986 | Russo |
| 4,605,399 A | 8/1986 | Weston et al. |
| 4,608,041 A | 8/1986 | Nielsen |
| 4,615,338 A | 10/1986 | Ilizarov |
| 4,624,656 A | 11/1986 | Clark et al. |
| 4,627,427 A | 12/1986 | Arco |
| 4,633,863 A | 1/1987 | Filips |
| 4,637,819 A | 1/1987 | Ouellette |
| 4,640,688 A | 2/1987 | Hauser |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. |
| 4,713,052 A | 12/1987 | Beck |
| 4,717,382 A | 1/1988 | Clemens et al. |
| 4,733,659 A | 3/1988 | Edenbaum |
| 4,743,232 A | 5/1988 | Kruger |
| 4,747,166 A | 5/1988 | Kuntz |
| 4,753,231 A | 6/1988 | Lang et al. |
| 4,759,354 A | 7/1988 | Quarfoot |
| 4,764,167 A | 8/1988 | Tu |
| 4,765,316 A | 8/1988 | Marshall |
| 4,773,409 A | 9/1988 | Cilento |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,822,278 A | 4/1989 | Oliva |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg |
| 4,846,162 A | 7/1989 | Moehring |
| 4,851,545 A | 7/1989 | Song et al. |
| 4,860,737 A | 8/1989 | Lang et al. |
| 4,863,449 A | 9/1989 | Therriault |
| 4,872,450 A | 10/1989 | Austad |
| 4,875,473 A | 10/1989 | Alvarez |
| 4,877,019 A | 10/1989 | Vives |
| 4,878,901 A | 11/1989 | Sachse |
| 4,890,608 A | 1/1990 | Steer |
| 4,897,081 A | 1/1990 | Poirier |
| 4,906,233 A | 3/1990 | Moriuchi et al. |
| 4,906,240 A | 3/1990 | Reed |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,973,331 A | 11/1990 | Pursley |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya |
| 5,002,528 A | 3/1991 | Palestrant |
| 5,002,529 A | 3/1991 | Cunningham |
| 5,002,543 A | 3/1991 | Bradshaw |
| 5,003,971 A | 4/1991 | Buckley |
| 5,014,389 A | 5/1991 | Ogilvie |
| 5,019,086 A | 5/1991 | Neward |
| 5,034,003 A | 7/1991 | Denance |

| | | | |
|---|---|---|---|
| 5,034,006 A | 7/1991 | Hosoda | |
| 5,034,012 A | 7/1991 | Frigg | |
| 5,035,884 A | 7/1991 | Song et al. | |
| 5,042,978 A | 8/1991 | Quenin | |
| 5,060,662 A | 10/1991 | Farnswoth, III | |
| 5,071,403 A | 12/1991 | Larsson | |
| 5,073,172 A | 12/1991 | Fell | |
| 5,086,763 A | 2/1992 | Hathman | |
| 5,086,764 A | 2/1992 | Gilman | |
| 5,100,396 A | 3/1992 | Zamierowski | |
| 5,100,404 A | 3/1992 | Hayes | |
| 5,101,808 A | 4/1992 | Kobayashi | |
| 5,102,413 A | 4/1992 | Poddar | |
| 5,103,806 A | 4/1992 | McLeod | |
| 5,106,362 A | 4/1992 | Gilman | |
| 5,106,629 A | 4/1992 | Cartmell | |
| 5,113,871 A | 5/1992 | Viljanto | |
| 5,135,518 A | 8/1992 | Vera | |
| 5,147,338 A | 9/1992 | Lang | |
| 5,149,331 A | 9/1992 | Ferdman et al. | |
| 5,152,757 A | 10/1992 | Eriksson | |
| 5,152,794 A | 10/1992 | Davidson | |
| 5,160,322 A | 11/1992 | Scheremet | |
| 5,167,613 A | 12/1992 | Karami | |
| 5,170,781 A | 12/1992 | Loomis | |
| 5,176,663 A | 1/1993 | Svedman | |
| 5,176,667 A | 1/1993 | DeBring | |
| 5,178,137 A | 1/1993 | Goor | |
| 5,191,880 A | 3/1993 | McLeod | |
| 5,228,431 A | 7/1993 | Giarretto | |
| 5,261,893 A | 11/1993 | Zamierowski | |
| 5,636,643 A | 6/1997 | Argenta et al. | |
| 5,720,720 A | 2/1998 | Laske | |
| 6,551,317 B2 | 4/2003 | Berish et al. | |
| 2003/0108587 A1 | 6/2003 | Orgill et al. | |

FOREIGN PATENT DOCUMENTS

| | | |
|---|---|---|
| DE | 1963258 | 6/1971 |
| DE | 2809828 | 9/1978 |
| DE | 4111122 | 4/1993 |
| EP | 0620720 | 10/1994 |
| EP | 0688189 | 9/2000 |
| EP | 0688189 B2 | 6/2005 |
| GB | 114754 | 4/1918 |
| GB | 641061 | 8/1950 |
| GB | 1273342 | 5/1972 |
| GB | 1457164 | 12/1976 |
| GB | 2 195 255 | 4/1988 |
| GB | 2195255 | 4/1988 |
| SU | 1416108 | 7/1985 |
| SU | 1251912 | 8/1986 |
| WO | 80/01139 | 6/1980 |
| WO | 87/00439 | 1/1987 |
| WO | WO 87/04626 | 8/1987 |
| WO | 87/04626 | 8/1987 |
| WO | 90/10424 | 9/1990 |
| WO | WO 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 94/20041 | 9/1994 |

OTHER PUBLICATIONS

Zivadinovic, G., et al., "Vacuum therapy in the treatment of peripheral blood vessels," Timok Medical Journal, Abstract book of the 5th Timok Medical Days, Majdanpek, 6 sheets of English translation, (1986), NPL–703.

Safronov, A.A., "Vacuum therapy for trophic ulcers of the tibia with concurrent skin autoplasty," Dissertation abstract, additional abstract, Moscow, 20 sheets of English translation, (1967). NPL–704.

Safronov, A.A., Abstract of Invention No. 240188, "Device for wound or ulcer treatment," (2 sheets English translation and 2 sheets in Russian) (1969). NPL–705.

Westaby, S., et al., "A wound irrigation device," Lancet, pp. 503–504 (Sep. 2, 1978). NPL–701.

Declaration of Dr. Kenneth R. Diller, Sc.D.

U.S. Appl. No. 07/792,001, Amendment and Reply under 37 C.F.R. § 1.111, mailed Apr. 29, 1996.

D.P. Orgill, L.R. Bayer, J. Neuwalder, and R.C. Felter, "Microdeformational Wound Therapy—A New Era in Wound Healing," in *Global Surgery: Future Directions in Surgery* (Touch Briefings, London, U.K. 2005) pp. 22–25.

M.J. Morykwas, B.J. Faler, D.J. Pearce, and L.C.Argenta, "Effects of Varying Levels of Subatmospheric Pressure on the Rate of Granulation Tissue Formation in Experimental Wounds in Swine," *Annals of Plastic Surgery* 47 (2001) 457–551.

*V.A.C. Therapy Clinical Guidelines: A Reference Source for Clinicians* (KCI Licensing Inc., San Antonio, TX 2007).

R. Fujimori, M. Hiramoto, and S. Ofuji, "Sponge Fixation Method for Treatment of Early Scars," *Plastic & Reconstructive Surgery* 47 (1968) 322–327.

N.A. Bagautdinov, "Variant of External Vacuum Aspiration in the Treatment of Purulent Diseases of Soft Tissue," in Current Problems of Modern Clinical Surgery: Interdepartmental Collection, edited by V.Ye. Volkov et al. (Chuvashia State University, Cheboksary, U.S.S.R. 1986) pp. 94–96.

G. Živadinović, V. Ðukić, Ž. Maksinivić, Ð. Radak, and P. Peška, "Vacuum Therapy in the Treatment of Peripheral Blood Vessels," *Timok Medical Journal* 11 (1986) 161–164.

F.E. Johnson, "An Improved Technique for Skin Graft Placement Using a Suction Drain," *Surgery, Gynecology, and Obstetrics* 159 (1984) 584–585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

C.E. Tennant, "The Use of Hyperemia in the Postoperative Treatment of Lesions of the Extremities and Thorax," *Journal of the American Medical Association* 64 (1915) 1548–1549.

Selections from W. Meyer and V. Schmieden, *Bier's Hyperemic Treatment in Surgery, Medicine, the Specialties: A Manual of Its Practical Application* (W.B. Saunders Co., Philadelphia, PA 1909), pp. 17–25, 44–64, 90–96, 167–170, and 210–211.

S. Westaby, and W.G. Everett, "A Wound Irrigation Device," *The Lancet* 312 (1978) 503–504.

D.E. Tribble, "An Improved Sump Drain–Irrigation Device of Simple Construction," *Archives of Surgery* 105 (1972) 511–513.

Declaration of Dr. Ian L. Gordon, M.D., Ph.D.

U.S. Appl. No. 10/647,068—Official Action P02977US1–OA–10 (Jan. 17, 2008).

Meehan, P.A., "Open adbominal wounds: a creative approach to a challenging problem", Progressions, 4(2):3–8, 11 (1992). NPL–276.

EP 0 620 720 (DE 692 24 847) Nullity Action filed by Molnlycke Health Care AB at the German Federal Patent Court to nullify EP 0 620 720 (DE 692 24 847) (EP equivalent of US5645081) and English translation, dated Mar. 10, 2008. MolnlyckeDEWH1–001.

Classification of features of Claim 1 of EP 0 620 720 B2 (EP equivalent of US5645081) labeled as "Anlage MFP1" in German with English translation (attachment to Nullity Action filed by Molnlycke on Mar. 10, 2008). MolnlyckeDEWH1–002.

Thomas, S., "Wound management and dressings," cover sheet, preface, sheet labeled "Chapter 5" and pp. 36–39 (1990). MolnlyckeDEWH1–003.

EP 0 620 720 Revocation Proceeding filed by Molnlycke Health Care AB at the UK High Court of Justice Chancery Division, Patents Court, Royal Courts of Justic, to revoke EP 0 620 720 (EP equivalent of US 5645081), dated Mar. 14, 2008. MolnlyckeUKHW1–001.

KCI et al. v. Blue Sky Medical Group et al., Case No. 2007–1340, –1341, –1342, Plaintiff–Cross Appellant's (Patent Owner's) Brief, with addendum chart, filed on Mar. 3, 2008. CAFC1340–002.

KCI et al. v. Blue Sky Medical Group et al., Case No. 2007–1340, –1341, –1342, Reply brief of appellants, Medela AG and Medela, Inc., filed by Medela on May 15, 2008. CAFC1340–003.

KCI et al. v. Blue Sky Medical Group et al., Case No. 2007–1340, –1341, –1342, Response and reply brief of defendant–appellant, Blue Sky Medical Group Inc., filed by Blue Sky on May 5, 2008. CAFC1340–004.

U.S. Appl. No. 10/161,076—Applicants' response P02915US0–OA–11 (Mar. 14, 2008).

U.S. Appl. No. 10/227,161—Applicants' response P02977US0–OA–13 (Jan. 30, 2007).

U.S. Appl. No. 10/647,068—Applicants'response P02977US1–OA–11 (Jan. 30, 2007).

Svedman, P., et al., "A dressing system providing fluid supply and suction drainage used for continuous or intermittent irrigation", Ann. Plast. Surg., 17(2):125–33 (Aug. 1986). NPL–389_.

"Pressure equivalents," McGraw–Hill Encyclopedia of Science & Technology, 6th ed., New York, pp. 249, (1987). NPL–687bw.

ITI v. KCI, Case No. 07–589, Reply brief in support of defendants' motion to dismiss complaint, filed by KCI on Dec. 12, 2007. DED–005.

ITI v. KCI, Case No. 07–589, First amended complaint, filed by ITI on Jan. 25, 2008. DED–006.

ITI v. KCI, Case No. 07–589, Defendants' motion, Proposed order, and Opening brief in support of defendants' motion to dismiss first amended complaint, or, alternatively, to transfer the case to the Middle District of North Carolina, filed by KCI on Mar. 12, 2008. DED–007.

ITI v. KCI, Case No. 07–589, Plaintiff's opposition to defendants' motion to dismiss, with declarations, filed by ITI on Apr. 4, 2008. DED–008.

ITI v. KCI, Case No. 07–589, Reply brief in support of defendants' motion to dismiss first amended complaint, or, alternatively, to transfer the case to the Middle District of North Carolina, filed by KCI on Apr. 21, 2008. DED–009.

KCI v. Medela, Case No. 08–cv–00087, (formerly 2:07cv187), Plaintiff's memorandum in support of continuing to stay litigation pending reexamination of U.S. Patent No. 7,216,651 and conclusion of related appeal, filed by Medela on May 9, 2008. SA087–001.

KCI v. Medela, Case No. 08–cv–00087, (formerly 2:07cv187), Plaintiffs KCI's and Wake Forest's brief in opposition to Medela's motion to stay, Proposed order denying Medela's motion to stay, with Exhibits, filed by KCI on May 16, 2008. SA087–002.

KCI v. Medela, Case No. 08–cv–00087, (formerly 2:07cv187), Defendants' reply to KCI's and Wake Forest's Brief in opposition to continue to stay litigation pending reexamination of U.S. Patent No. 7,216,651 and conclusion of related appeal, with Proposed order, filed by Medela on May 21, 2008. SA087–003.

KCI, et al., v. Blue Sky Medical Group, Inc., et al., SA08–cv–102, (formerly 2:07cv188), Defendants Blue Sky Medical Group, Inc's and Smith & Nephew, Inc.'s motion to stay, with Proposed order and Exhibits, filed by Blue Sky on May 9, 2008. SA00102–001.

KCI, et al., v. Blue Sky Medical Group, Inc., et al., SA08–cv–102, (formerly 2:07cv188), Plaintiffs KCI's and Wake Forest's brief in opposition to defendants' motion to stay, with Proposed order and Exhibits, filed by KCI on May 16, 2008. SA00102–002.

KCI, et al., v. Blue Sky Medical Group, Inc., et al., SA08–cv–102, (formerly 2:07cv188), Defendants Blue Sky Medical Group, Inc.'s and Smith & Nephew, Inc.'s reply in support of their motion to stay, with exhibit, filed by Blue Sky on May 21, 2008. SA00102–003.

Medela v. KCI, Case No. 7cv449, Plaintiff's memorandum in support of continuing to stay litigation pending reexamination of U.S. Patent No. 7,216,651 and conclusion of related appeal, filed by Medela on May 9, 2008. SA449–007.

Medela v. KCI, Case No. 7cv449, Plaintiffs KCI's and Wake Forest's brief in opposition to Medela's motion to stay with Proposed order and exhibits, filed by KCI on May 16, 2008. SA449–008.

Medela v. KCI, Case No. 7cv449, Plaintiff's reply to KCI's and Wake Forest's Brief in opposition to continue to stay litigation pending reexamination of U.S. Patent No. 7,216,651 and conclusion of related appeal, with Proposed order and exhibit, filed by Medela on May 21, 2008. SA449–009.

Blue Sky v. KCI, Case No. 7cv454, Plaintiffs Blue Sky Medical Group, Inc.'s and Smith & Nephew, Inc.'s motion to stay, Proposed order, and exhibits, filed by Blue Sky on May 9, 2008. SA454–008.

Blue Sky v. KCI, Case No. 7cv454, Plaintiffs KCI's and Wake Forest's brief in opposition to defendants' motion to stay, with Proposed order and exhibits, filed by KCI on May 16, 2008. SA454–009.

Blue Sky v. KCI, Case No. 7cv454, Plaintiffs Blue Sky Medical Group, Inc.'s and Smith & Nephew, Inc.'s reply in support of their motion to stay, filed by Blue Sky on May 21, 2008. SA454–010.

KCI et al. v. Blue Sky Medical Group et al., Case No. 2007–1340, –1341, –1342, Corrected reply brief of appellants, Medela AG and Medela, Inc., filed by Medela on May 21, 2008. CAFC1340–005.

WFU v. ITI, 1:08–cv–32, Answer to complaint with jury demand, filed by ITI on Mar. 4, 2008. MDNC32–002.

*WUF* v. *ITI*, 1:08–cv–32, Defendant ITI's motion to transfer venue, Proposed order, and Brief in support of defendant ITI's motion to transfer venue, or in the alternative, motion to stay, filed by ITI on Mar. 12, 2008. MDNC32–003.

*WFU* v. *ITI*, 1:08–cv–32, Plaintiffs' brief in opposition to defendant's motion to transfer venue, or in the alternative, motion to stay, filed by WFU on Apr. 18, 2008. MDNC32–004.

*WFU* v. *ITI*, 1:08–cv–32, Defendant ITI's reply brief in support of its motion to transfer venue, or in the alternative, motion to stay, with exhibits, filed by ITI on May 5, 2008. MDNC32–005.

*KCI* v. *BlueSky*, Trial Transcript for Orgill/Bridi/McGregor/Girolami/Taylor, dated Jul. 12, 2006. BS–116.

Request for Inter Partes Reexamination of U.S. Patent No. 7,216,651, requested May 30, 2008. IPRE–001.

Exhibits to Request for Inter Partes Reexamination of U.S. Patent No. 7,216,651, requested May 30, 2008. IPRE–002.

Bagautdinov, N.A., "Alternative method of external vacuum aspiration in the treatment of purulent soft tissue disease," Curr. Problems Contemporary Clin. Surg.: Interscholastic Collection, pp. 94–96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May 7, 2008); I.N. Ulianov Chuvash State University, Cheboksary, (1986). NPL–690.

Zivadinovic, G., et al., "Vacuum therapy in the treatment of peripheral blood vessels," Conference Papers of the 5th Timok Medical Days, Majdanpek, No. 3–4, pp. 161–164, (5 sheets English translation; 5 sheets in Serbian, certification dated May 9, 2008) (1986). NPL–691.

Johnson, F.E., "An improved technique for skin graft placement using a suction drain", Surg. Gynecol. Obstet., 159 (6):584–585 (Dec. 1984). NPL–226__.

Safronov, A.A., Dissertation Abstract, "Vacuum therapy of trophic ulcers of the lower leg with simultaneous autoplasty of the skin," (Central Scientific Research Institute of Traumotology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967). NPL–692.

Tribble, D.E., "An improved sump drain–irrigation device of simple construction," Arch. Surg., 105:511–513, (Sep. 1972). NPL–693.

Tennant, C.E., "The use of hyperemia in the postoperative treatment of lesions of the extremities and thorax," Jour. A.M.A., 64(19):1548–1549, (May 8, 1915). NPL–694.

Orgill, D.P., et al., "Microdeformational wound therapy—a new era in wound healing," Business Briefing: Global Surgery—Future Directions, pp. 22, 24–25 (2005). NPL–695.

"V.A.C.® Therapy Clinical Guidelines: A reference source for clinicians," KCI, The Clinical Advantage® (Jul. 2007). NPL–696.

*KCI et al.* v. *Blue Sky Medical Group et al.*, Case No. 2007–1340, –1341, –1342, Federal Circuit Decision dated Feb. 2, 2009. CAFC1340–008.

*Wake Forest University Health Sciences, et al.*, v. *Smith & Nephew, et al.*, In the High Court of Justice, Chancery Division, Patents Court, (UK) Case No. HC08 C03563, Witness Statement of Sabing Lee, dated Jan. 6, 2009. SNUK–001.

*WFU* v. *S&N*, (UK) Case No. HC08 C03563, Witness Statement of John Hicks, dated Jan. 6, 2009. SNUK–002.

*WFU* v. *S&N*, (UK) Case No. HC08 C03563, Witness Statement of Martin Connors, dated Jan. 5, 2009. SNUK–003.

*WFU* v. *S&N*, (UK) Case No. HC08 C03563, Witness Statement of Nadeem Bridi, with Exhibit NB–1 and NB–2, dated Jan. 9, 2009. SNUK–004.

*WFU* v. *S&N* (UK) Case No. HC08 C03563, Defendants' skeleton argument for hearing floating from Tuesday Jan. 13, 2009,filed Jan. 12, 2009. SNUK–005.

*WFU* v. *S&N* (UK) Case No. HC08 C03563, Plaintiffs' skeleton argument for hearing, filed Jan. 12, 2009. SNUK–006.

*KCI, et al.*, v. *Blue Sky Medical Group, Inc., et al.*, SA08–cv–102, (formerly 2:07cv188), Defendants Blue Sky Medical Group, Inc. and Smith & Nephew, Inc.'s answer to third amended complaint, filed Jan. 20, 2009. SA00102–005.

EP 0 620 720 (DE 692 24 847) Medela's Brief in Reply to the Complaint Reply Brief with English translation, dated Dec. 19, 2008. DENA–WH1–010.

EP 0 688 189 (DE 694 25 881) Medela's Reply Brief dated Dec. 19, 2008. DENA–WH2–006.

*KCI et al.* v. *Blue Sky Medical Group et al.*, Case No. 2007–1340, –1341, –1342, Medela's petition for rehearing and suggestion for rehearing en banc, dated Feb. 17, 2009. CAFC1340–009.

*KCI* v. *Medela*, Case No. 08–cv–00087, (formerly 2:07cv187), First amended disclosure of asserted claims and infringement contentions, Exhibits A–C, and Plaintiffs' notice of disclosure of first amended asserted claims and infringement contentions filed Feb. 27, 2009. SA087–004.

*KCI* v. *Medela*, Case No. 08–cv–00087, (formerly 2:07cv187), Medela, Inc. and Medela AG's proposal terms and claim elements for construction, dated Apr. 10, 2009. SA087–005.

*KCI, et al.*, v. *Blue Sky Medical Group, Inc., et al.*, SA08–cv–102, (formerly 2:07cv188), First amended disclosure of asserted claims and infringement contentions, Exhibits A–E, and Plaintiff's notice of disclosure of first amended asserted claims and infringement contentions, filed Feb. 27, 2009. SA102–006.

*KCI, et al.*, v. *Blue Sky Medical Group, Inc., et al.*, SA08–cv–102, (formerly 2:07cv188). Memorandum in support of Plaintiffs' motion for a preliminary injunction and Exhibits 1–16, dated Mar. 13, 2009 SA102–007.

*KCI, et al.*, v. *Blue Sky Medical Group, Inc., et al.*, SA08–cv–102, (formerly 2:07cv188), Supplement to memorandum in support of Plaintiffs' motion for a preliminary injunction, with exhibit, filed Mar. 27, 2009. SAO0102–O09.

*KCI et al.* v. *Blue Sky Medical Group et al.*, Case No. 2007–1340, –1341, –1342, Opposition of KCI, et al. to Medela's petition for rehearing and suggestion for rehearing en banc, dated Mar. 6, 2009. CAFC1340–010.

*KCI, et al.*, v. *Blue Sky Medical Group, Inc., et al.*, SA08–cv–102, (formerly 2:07cv188), Smith & Nephew, Inc.'s opposition to Plaintiffs' motion for a preliminary injunction, with proposed order, and Exhibits C, H, N, P. R, T, U, V, X, Y, and Z, filed by S&N on Apr. 3, 2009. SA102–021.

*KCI, et al.*, v. *Blue Sky Medical Group, Inc., et al.*, SA08–cv–102, (formerly 2:07cv188), Declaration of Ian L. Gordon, M. D., Ph.D. in support of Smith & Nephew, Inc.'s opposition to Plaintiffs' motion for preliminary injunction, filed by S&N on Apr. 3, 2009. SA102–022.

Transeal transparent wound dressing, DeRoyal, 4 sheets (2003). NPL–733.

Kuznetsov, V.A., "Vacuum and vacuum–sorption treatment of open septic wounds," in II All–union conference "Wounds and wound infections" "(Presentation abstracts)" in Russian with English translation dated Apr. 2, 2009, with table of contents, Moscow, Oct. 28–29, 1986. NPL–734.

Bagautdinov, N.A., "Variant of external vacuum aspiration in the treatment of purulent disease of soft tissue," pp. 94–96 and introduction by V.E. Volkov and an opinion by V. V. Shutova dated Feb. 4, 2009, in Russian with English translation, with alleged card catalogue card with English translation, and certification of translation dated Feb. 19, 2009, Current Problems in Modern Clinical Surgery, (1986). NPL–724.

Kuznetsov, V.A., "Vacuum and vacuum–sorption treatment of open septic wounds," in II All–union conference "Wounds and wound infection" "(Abstracts of presentations)" in Russian with English translation, and card with English translation, Moscow, Oct. 28–29, 1986. NPL–725 (Bagautdinov II).

*KCI, et al.*, v. *Blue Sky Medical Group, Inc., et al.*, SA08–cv–102, (formerly 2:07cv188), Defendant Blue Sky Medical Group, Inc.'s opposition to plaintiffs' motion for a preliminary injunction, with proposed order and Declaration of Edward B. Armstrong III, filed Apr. 3, 2009. SA102–016.

*KCI, et al.*, v. *Blue Sky Medical Group, Inc., et al.*, SA08–cv–102, (formerly 2:07cv188), Defendants' reply to plaintiffs' response in opposition to defendants' motion to extend time, compel depositions and increase page limit for defendants' opposition brief, filed by Blue Sky and S&N, Mar. 20, 2009. SA102–017.

*KCI, et al.*, v. *Blue Sky Medical Group, Inc., et al.*, SA08–cv–102, (formerly 2:07cv188), Defendants' response to "Plaintiffs' motion for a preliminary injunction and request for evidentiary hearing," with proposed order, filed by Blue Sky and S&N Feb. 26, 2009. SA102–018.

*WFU* v. *S&N* (UK) Case No. HC08 C03563, Trial transcript day 1, Mar. 23, 2009. SNUK–010.

*WFU* v. *S&N* (UK) Case No. HC08 C03563, Trial transcript day 2, Mar. 24, 2009. SNUK–011.

*WFU* v. *S&N* (UK) Case No. HC08 C03563, Trial transcript day 3, Mar. 25, 2009. SNUK–012.

*KCI, et al.*, v. *Blue Sky Medical Group, Inc., et al.*, SA08–cv–102, (formerly 2:07cv188), Defendants BlueSky Medical Group, Inc. and Smith & Nephew, Inc.'s proposed terms and claim elements for construction, dated Apr. 10, 2009. SA102–015.

EP 0 620 720 (DE 692 24 847), Reply brief by Wake Forest, with brief in German and Attachment A, dated Jun. 3, 2008. DENA–WH1–015.

EP 0 620 720 (DE 692 24 847), Reply brief by Wake Forest to Medela, with brief in German and enclosures H–L, dated Jan. 16, 2009. DENA–WH1–016.

EP 0 620 720 (DE 692 24 847), English translation of the Minutes of the oral proceeding held on Mar. 17, 2009, DENA–WH1–017.

*Innovative Therapies, Inc.*, v. *Kinetic Concepts, Inc., KCI Licensing, Inc., and KCI USA, Inc.*, Appeal from the U.S. District Court for the District of Delaware in case No. 07–cv–589, Federal Circuit Court of Appeals, Case No. 2009–1085, Brief of KCI filed by KCI on Apr. 17, 2009. CAFC1085–001.

Robson, M.C., et al., Chapter 10 "Wounds and wound healing," p. 107–114 in Essentials of General Surgery, P.F. Lawrence ed., Williams & Wilkins, (1988). NPL–714.

Robson, M.C., et al., Chapter 11 "Wounds and wound healing," p. 119–126 in Essentials of General Surgery, 2nd edition, P.F. Lawrence ed., Williams & Wilkins, (1992). NPL–715.

Smith, D.J. Jr. et al., Chapter 7 "Wounds and wound healing," p. 113–122 in Essentials of General Surgery, 3d edition, P.F. Lawrence ed., Lippincott Williams & Wilkins (2000). NPL–716.

Talboy, G.E., et al., "Chapter 8: Wounds and wound healing," p. 147–161 in Essentials of General Surgery, B. Sun ed., Lippincott Williams & Wilkins, (2006). NPL–717.

Garrison, R.N., et al., "Chapter 9: Surgical infections," p. 163–179 in Essentials of General Surgery, B. Sun ed., Lippincott Williams & Wilkins, (2006). NPL–718.

Sumpio, B.E., et al., "Role of negative pressure wound therapy in treating peripheral vascular graft infections," Vascular, 16(4):194–200, (2008). NPL–719.

Taber's Cyclopedic Medical Dictionary, Edition 20, pp. 306–309, 728–729, 765, 1726, and 2006–2009. (2005). NPL–720.

Mills, N., Polymer Foams Handbook: engineering and biomechanics applications and design guide, pp. 2–3, (2007). NPL–722.

Bucknall, T.E., et al., eds., "Sutures and dressings," p. 88–93 in Wound Healing for Surgeons, (1984). NPL–723.

EP 0 620 720 (DE 692 24 847), Smith & Nephew brief, with English translation and exhibits VP1, VP2, VP3, VP4, and VP6, dated Mar. 12, 2009. DENA–Wh1–013.

*KCI, et al.*, v. *Blue Sky Medical Group, Inc., et al.*, SA08–cv–102, (formerly 2:07cv188), Plaintiffs' motion for a preliminary injunction and request for evidentiary hearing, with proposed order, filed by KCI Feb. 20, 2009. SA102–019.

Parker, S.P., ed., McGraw–Hill Dictionary of Scientific and Technical Terms, 5th ed., pp. 139, 533, 772, and 1672 (1994). NPL–726.

Merriam–Webster Online, "reepithelialization," printout of webpage dated Apr. 17, 2009. NPL–727.

Oxford English Dictionary Online, "deformable," "deform," and "flexible," printout of webpages dated Apr. 17, 2009. NPL–728.

Alger, M.S.M., Polymer Science Dictionary, (4 sheets), Elsevier Science Publishers Ltd. (1989). NPL–729.

Stedman's Medical Dictionary, 25th ed., pp. 554, 667–668, and 1603–1604, Williams & Wilkins, (1990). NPL–730.

Webster's New World Dictionary of the American Language, pp. 1105, Simon & Schuster, Inc., (1984). NPL–731.

Larichev, A.B. et al., "Vacuum–therapy in the complex of treatment of festering wounds," Khirurgiia (Mosk.), 6:22–26, (13 sheets English translation, 5 sheets in Russian, English abstract on pp. 22), (2008). NPL–707.

Ersh, Z. Ya, "Use of polyurethane foam for treating purulent cavities and wounds," Purulent Septic Unit of Hospital No. 35 (2 sheets English and 2 sheets Russian), allegedly submitted for publication Mar. 21, 1984. NPL–708.

Lokhvitskii, S.V., et al., "External vacuum aspiration in the treatment of purulent disorders of the soft tissues," Inpatient Surgery Clinic of the Therapeutic Department at Karagandy Medical Institute, Municipal Hospital No. 1, Temirtau, pp. 130–134 (5 sheets English, 5 sheets Russian), allegedly submitted Sep. 22, 1982. NPL–709.

Kanshin, N.N., "Closed treatment of suppurative processes by the method of active lavage drainage," Third Surgical Clinic of the N.V. Sklifosovkiy Moscow Scientific Research Institute of Emergency Care, pp. 18–23, (6 sheets in English, 6 sheets in Russian and English abstract on pp. 22–23), allegedly submitted 1979. NPL–710.

Bui, T.D., et al., "Negative pressure wound therapy with off–the–shelf components," Am. J. Surg., 192:235–237, (2006). NPL–706.

Vacuum Assisted Closure (V.A.C. (R)) Therapy: an overview of scientific, clinical, and cost effectiveness evidence, (19 sheets) KCI Licensing, Inc., 2009. NPL–711.

Scherer, S.S., et al., "The mechanism of action of the vacuum–assisted closure device," Plast. Reconstr. Surg., 122:786–797, (presented at the Wound Healing Society Meeting 2007 in Tampa, Florida, Apr. 28–May 1) (2008). NPL–712.

Greene, A.K., et al., "Microdeformational wound therapy," Ann. Plast. Surg., 56(4):418–422, (2006). NPL–713.

KCI, "The V.A.C. operations summary," 7 sheets, (1999). NPL–732.

*KCI v. Medela*, Case No. 08–cv–00087, (formerly 2:07cv187), Plaintiffs' preliminary claim constructions and identification of extrinic evidence, filed by KCI on Apr. 17, 2009. SA087–020.

*KCI v. Medela*, Case No. 08–cv–00087, (formerly 2:07cv187), Medela, Inc. and Medela AG's preliminary claim constructions and identification of extrinsic evidence dated Apr. 17, 2009, with Exhibit AA (Declaration of Dr. I.L. Gordon, dated Apr. 2, 2009 (filed Apr. 3, 2009)). SA087–021.

*KCI, et al., v. Blue Sky Medical Group, Inc., et al.*, SA08–cv–102, (formerly 2:07cv188), Plaintiffs' preliminary claim constructions and identification of extrinsic evidence, by KCI dated Apr. 17, 2009. SA102–020.

*KCI, et al., v. Blue Sky Medical Group, Inc., et al.*, SA08–cv–102, (formerly 2:07cv188), Plaintiffs' reply in support of motion for a preliminary injunction with regard to Blue Sky Medical Group, Inc., filed by KCI on Apr. 15, 2009. SA102–008.

*KCI, et al., v. Blue Sky Medical Group, Inc., et al.*, SA08–cv–102, (formerly 2:07cv188), Plaintiffs' reply in support of motion for a preliminary injunction, with Exhibits 17 and 24, filed Apr. 15, 2009. SA102–023.

Murphey, G.C., et al., "Depth of penetration of negative pressure wound therapy into underlying tissues," Wound Repair and Regeneration, 17:113–117 (2009). NPL–735.

Jargin, S.V., "Limited access to foreign medical literature in Russia," Chartered Institute of Library and Information Professionals Health Libraries Group Newsletter, 25(4):7–10, (Dec. 2008). NPL–736.

*KCI, et al., v. Blue Sky Medical Group, Inc., et al.*, SA08–cv–102, (formerly 2:07cv188). Defendant Blue Sky Medical Group, Inc.'s sur–reply in further support of its opposition to Plaintiffs' motion for preliminary injunction, filed by Blue Sky on Apr. 22, 2009. SA102–024.

*KCI, et al., v. Blue Sky Medical Group, Inc., et al.*, SA08–cv–102, (formerly 2:07cv188), Defendant Smith & Nephew, Inc.'s sur–reply in further support of its opposition to Plaintiffs' motion for preliminary injunction, with Exhibits CC, GG, II–PP, filed by S&N on Apr. 22, 2009. SA102–025.

3M™ Tegaderm™ Transparent film dressings—wound, Commonly asked questions, 4 sheets, (Jan. 2007). NPl–737.

British Pharmacopoeia 19, vol. II, p. 927 and p. 548 of 1986 addendum, (vol. II—1980, addendum—1986). NPL–738.

*KCI, et al., v. Blue Sky Medical Group, Inc., et al.*, SA08–cv–102, (formerly 2:07cv188), Defendants Blue Sky Medical Group, Inc. and Smith & Nephew, Inc.'s preliminary claim constructions and extrinsic evidence, by Blue Sky and S&N dated Apr. 17, 2009. SA102–026.

Website printout "Chemical of the week" polymers, 5 sheets, printout dated Apr. 17, 2009. NPL–739bw.

Orgill, D.P., et al., "Functional reconstruction following electrical injury", Ann. N.Y. Acad. Sci., 888:96–104 (Oct. 30, 1999), NPL–321.

Orgill, D.P., et al., "Guidelines for treatment of complex chest wounds with negative pressure wound therapy", Supplement B to Wounds: A Compendium of Clinical Research and Practice, (24 sheets), (Dec. 2004). NPL–578.

Orgill, D.P., "Utilizing negative pressure wound therapy on open chest/stemotomy wounds", Ostomy Wound Manage, 50(11A suppl):15S–17S (Nov. 2004). NPL–579.

Orgill, D.P., "Advancing the treatment options of chest wounds with negative pressure wound therapy", Ostomy Wound Manage., 51(2A suppl):39S–43S (Feb. 2005). NPL–580.

Colwell, A.S., et al., "Management of early groin vascular bypass graft infections with sartorius and rectus femoris flaps", Ann. Plast. Surg., 52(1):49–53 (Jan. 2004). NPL–532.

Saxena, V., et al., "Vacuum–assisted closure: microdeformations of wounds and cell proliferation", Plast. Reconstruct. Surg. 114(5):1086–96 (Oct. 2004). NPL–493.

*KCI v. Medela*, Case No. 08–cv–00087, (formerly 2:07cv187), Defendants Medela AG and Medela, Inc. preliminary invalidity contentions, dated Apr. 3, 2009. SA087–006.

*KCI v. Medela*, Case No. 08–cv–00087, (formerly 2:07cv187), Appendix A of Defendants Medela AG and Medela, Inc. preliminary invalidity contentions (Claim Chart: Jeter), dated Apr. 3, 2009. SA087–007.

*KCI v. Medela*, Case No. 08–cv–00087, (formerly 2:07cv187), Appendix B of Defendants Medela AG and Medela, Inc. preliminary invalidity contentions (Claim Chart: Chariker 1989 use), dated Apr. 3, 2009. SA087–008.

*KCI v. Medela*, Case No. 08–cv–00087, (formerly 2:07cv187), Appendix C of Defendants Medela AG and Medela, Inc. preliminary invalidity contentions (Claim Chart: Chariker/Jeter uses and presentations), dated Apr. 3, 2009. SA087–009.

*KCI v. Medela*, Case No. 08–cv–00087, (formerly 2:07cv187), Appendix D of Defendants Medela AG and Medela, Inc. preliminary invalidity contentions (Claim Chart: MCL treatments), dated Apr. 3, 2009. SA087–010.

*KCI v. Medela*, Case No. 08–cv–00087, (formerly 2:07cv187), Appendix E of Defendants Medela AG and Medela, Inc. preliminary invalidity contentions (Claim Chart: Zamierowski '880), dated Apr. 3, 2009. (SA087–011.

*KCI v. Medela*, Case No. 08–cv–00087, (formerly 2:07cv187), Appendix F of Defendants Medela AG and Medela, Inc. preliminary invalidity contentions (Claim Chart: Svedman art), dated Apr. 3, 2009. SA087–012.

*KCI v. Medela*, Case No. 08–cv–00087, (formerly 2:07cv187), Appendix G of Defendants Medela AG and Medela, Inc. preliminary invalidity contentions (Claim Chart: GB 2,195,255), dated Apr. 3, 2009. SA087–013.

*KCI v. Medela*, Case No. 08–cv–00087, (formerly 2:07cv187), Appendix H of Defendants Medela AG and Medela, Inc. preliminary invalidity contentions (Claim Chart: Argenta and Morykwas (1997) Ann. Plast. Surg. 38:563–77), dated Apr. 3, 2009. SA087–014.

*KCI v. Medela*, Case No. 08–cv–00087, (formerly 2:07cv187), Appendix I of Defendants Medela AG and Medela, Inc. preliminary invalidity contentions (Claim Chart: Morykwas and Argenta (1993) Abstract FASEB J., Experimental Biology '93, New Orleans, Louisiana, presentation 800), dated Apr. 3, 2009. SA087–015.

*KCI v. Medela*, Case No. 08–cv–00087, (formerly 2:07cv187), Appendix J of Defendants Medela AG and Medela, Inc. preliminary invalidity contentions (Claim Chart: Johnson), dated Apr. 3, 2009. SA087–016.

*KCI v. Medela*, Case No. 08–cv–00087, (formerly 2:07cv187), Appendix K of Defendants Medela AG and Medela, Inc. preliminary invalidity contentions (Claim Chart: Bagautdinov I and II), dated Apr. 3, 2009. SA087–017.

*KCI v. Medela*, Case No. 08–cv–00087, (formerly 2;07cv187), Appendix L of Defendants Medela AG and Medela, Inc. preliminary invalidity contentions (Claim Chart: Harvey), dated Apr. 3, 2009. SA087–018.

*KCI v. Medela*, Case No. 08–cv–00087, (formerly 2:07cv187), Appendix M of Defendants Medela AG and Medela, Inc. preliminary invalidity contentions (Claim Chart: Nakayama 1990 and 1991), dated Apr. 3, 2009. SA087–019.

*KCI, et al., v. Blue Sky Medical Group, Inc., et al.*, SA08–cv–102, (formerly 2:07cv188), Defendants' preliminary invalidity contentions, filed by Blue Sky on Apr. 3, 2009. SA102–010.

*KCI, et al., v. Blue Sky Medical Group, Inc., et al.*, SA08–cv–102, (formerly 2:07cv188), Exhibit A of Defendants' preliminary invalidity contentions (Claim Chart: US 7,216,651), filed by Blue Sky on Apr. 3, 2009. SA102–011.

*KCI, et al., v. Blue Sky Medical Group, Inc., et al.*, SA08–cv–102, (formerly 2:07cv188), Exhibit B of Defendants' preliminary invalidity contentions (Claim Chart: US 7,198,046), filed by Blue Sky on Apr. 3, 2009. SA102–012.

*KCI, et al., v. Blue Sky Medical Group, Inc., et al.*, SA08–cv–102, (formerly 2:07cv188), Exhibit C of Defendants' preliminary invalidity contentions (Claim Chart US 5,636,643), filed by Blue Sky on Apr. 3, 2009. SA102–013.

*KCI, et al., v. Blue Sky Medical Group, Inc., et al.*, SA08–cv–102, (formerly 2:07cv188), Exhibit D of Defendants' preliminary invalidity contentions (Claim Chart US 5,645,081), filed by Blue Sky on Apr. 3, 2009. SA102–014.

*WFU v. S&N* (UK) Case No. HC08 C03563, Defendants' civil evidence act notice, with Opinions by Y.A. Grikhanov, L. A. Matyushenkova, V.V. Shutova, and Opinion of L.N. Tikhonova (with enclosures) served Feb. 20, 2009. SNUK–008.

*WFU v. S&N* (UK) Case No. HC08 C03563, Defendants 2nd civil evidence act notice, with Declaration of S.L. Danilovna (in Russian and 8 pp. English translation, with Current Problems in Modern Clinical Surgery), served Mar. 13, 2009. SNUK–021.

*WFU v. S&N* (UK) Case No. HC08 C03563, Expert report of Dr. Ian Louis Gordon, with Annex 1 and Exhibits 1, 4, and 7, dated Mar. 6, 2009. SNUK–009.

*WFU v. S&N* (UK) Case No. HC08 C03563, Second expert report of Dr. Ian Louis Gordon, dated Mar. 16, 2009. SNUK–014.

*WFU v. S&N* (UK) Case No. HC08 C03563, Second witness statement of Sabing Lee, with Exhibit SL–6, dated Jan. 12, 2009. SNUK–015.

*WFU v. S&N* (UK) Case No. HC08 C03563, Defendants' opening trial skeleton argument, dated Mar. 19, 2009. SNUK–017.

*WFU v. S&N* (UK) Case No. HC08 C03563, Defendants' closing submissions, dated Mar. 26, 2009. SNUK–019.

*WFU v. S&N* (UK) Case No. HC08 C03563, Grounds of invalidity, filed by S&N, served Jan. 19,2009. SNUK–022.

*WFU v. S&N* (UK) Case No. HC08 C03563, Defendants' admissions in respect of the allegation of infringement, filed by S&N, served Jan. 30, 2009. SNUK–023.

*WFU v. S&N* (UK) Case No. HC08 C03563, Defendants' statement of opposition to the proposed amendment, filed by S&N, served Mar. 12, 2009. SNUK–026.

*WFU v. S&N* (UK) Case No. HC08 C03563, Witness statement of Edward Armstrong, dated Mar. 11, 2009. SNUK–020.

*WFU v. S&N* (UK) Case No. HC08 C03563, Approved judgment of Mr. Justice Lewison, dated Jan. 13, 2009. SNUK–027.

*WFU v. S&N* (UK) Case No. HC08 C03563, First expert report of Dr. Dennis Paul Orgill, with Exhibits 4, 5, and 12, dated Mar. 6, 2009. SNUK–007.

*WFU v. S&N* (UK) Case No. HC08 C03563, Transcript of hearing, Jan. 13, 2009. SNUK–013.

Kirk–Othmer, Encyclopedia of Chemical Technology, 2nd completely revised edition, vol. 9, pp. 220–232, John Wiley & Sons, Inc., (1966). NPL–744.

*WFU v. S&N* (UK) Case No. HC08 C03563, KCI's opening skeleton argument, dated Mar. 19, 2009. SNUK–016.

*WFU v. S&N* (UK) Case No. HC08 C03563, KCI's closing note of argument, dated Mar. 25, 2009. SNUK–018.

Stedman's Medical Dictionary, 25th ed., pp. 1739, Williams & Wilkins, (1990). NPL–743.

Standard Operating Procedure, The determination of moisture vapour permeability (MVP) and water transmission rate (WTR), implementation date: Sep. 11, 2006 and QA Operational Laboratories Analytical Report dated Nov. 13, 2008. NPL–745.

British Pharmacopoeia Selections: (1988) vol. II, p. 1126–1127, A223–A224; Addendum 1992, p. 1494; (1993) vol. II, p. 1266, A218–A219. NPL–746.

*WFU v. S&N* (UK) Case No. HC08 C03563, Claimants' letter regarding independent validity, filed by KCI, dated Jan. 30, 2009. SNUK–024.

*WFU v. S&N* (UK) Case No. HC08 C03563, Statement of reasons, filed by KCI, served Mar. 4, 2009. SNUK–025.

Inter Partes Reexam of US 7,216,651, Reexam Nos. 90/008,693 and 95/001,048, Third party comments addressing issues raised by the Feb. 12, 2009 office action and the Apr. 12, 2009 Patent Owner's reply, filed by S&N, dated May 12, 2009. IPRE–006.

Inter Partes Reexam of US 7,216,651, Reexam Nos. 90/008,693 and 95/001,048, Third party requester's petition pursuant to 37 C.F.R. §1.183 for waiver of 37 C.F.R. §1.943(b) requirement, filed by S&N, dated May 12, 2009. IPRE–007.

Inter Partes Reexam of US 7,216,651, Reexam Nos. 90/008,693 and 95/001,048, Exhibit A of Third Party Comments: Declaration of Dr. Nail A. Bagaoutdinov, filed by S&N, dated May 8, 2009. IPRE–008.

Inter Partes Reexam of US 7,216,651, Reexam Nos. 90/008,693 and 95/001,048, Exhibit B of Third Party Comments: Declaration of Dr. Mark Chariker, with Appendix C, filed by S&N, dated May 11, 2009. IPRE–009.

Inter Partes Reexam of US 7,216,651, Reexam Nos. 90/008,693 and 95/001,048, Exhibit C of Third Party Comments: Dr. Ian L. Gordon, M.D., Ph.D., Declaration, with Appendix D, filed by S&N, dated May 12, 2009. IPRE–010.

Inter Partes Reexam of US 7,216,651, Reexam Nos. 90/008,693 and 95/001,048, Exhibit E of Third Party Comments: Excerpts from the trial transcript in the U.S.D.C.—Western District of Texas, Case No. SA–03–CA–832, entitled *Kinetic Concepts v. Bluesky Medical Corp.*, filed by S&N on May 12, 2009. IPRE–011.

Inter Partes Reexam of US 7,216,651, Reexam Nos. 90/008,693 and 95/001,048, Exhibit G of Third Party Comments: Excerpts of U.K. trial transcript for *Wake Forest University v. Smith & Nephew PLC* of Mar. 24, 2009, filed by S&N on May 12, 2009. IPRE–012.

Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988). NPL–769.

Solovev, V.A., "The method of treatment of immature external fistulas in the upper gastrointestinal tract," S.M. Kirov Gorky State Medical Institute, Gorky, U.S.S.R., (Exhibit J of Third party comments) (1987). NPL–770.

*WFU v. S&N* (UK) Case No. HC08 C03563, Approved judgment before Mr. Roger Wyand QC, (Exhibit H of Third party comments) dated May 1, 2009. SNUK–028.

Taber's Cyclopedic Medical Dictionary, 16th edition, pp. 613–614, 643, 679, 1444, and 1686–1688, (1989). NPL–740.

Parker, S.P., ed., McGraw–Hill Dictionary of Scientific and Technical Terms, 4th ed., pp. 1462, (1989). NPL–741.

Gove, P.B., ed., Webster's Third New International Dictionary Unabridged, pp. 869 and 2627 (1986). NPL–742.

Peacock, Jr., E.E., Wound Repair, 3d edition, W.B. Saunders Company pp. 12–14, pp. 38–51, Chapter 6 Repair of skin wounds, (1984). NPL–721.

Spartanburg Regional Medical Center Operative reports, 35 sheets, dated 1989. NPL–747.

Johnson, F.E., "Expanded use of suction drains," pp. 469 and 1 sheet of drawings (allegedly dated 1985). NPL–748.

Brossy, J.–J., "Foam elastomer dressings in surgery," SA Medical Journal, 59:559–560, (Apr. 1981). NPL–749.

Groves, A.R., et al., "Silastic foam dressing: an appraisal," Annals of the Royal College of Surgeons of England, vol. 67, pp. 117–118, and additional page, (1985). NPL–750.

Harding, K.G., et al., "Silastic foam dressing for skin graft donor sites—a preliminary report," Br. J. Plast. Surg., 33:418–421, (1980). NPL–751.

Malone, W.D., "Wound dressing adherence: a clinical comparitive study," Archives of Emergency Medicine, 4:101–105, (1987). NPL–752.

Moblvac II advertising materials, 4 sheets, allegedly dated 1984. NPL–753.

Bucknall, T.E. ed., et al., "Wound healing for surgeons," Introduction, Chapter 1 The healing wound, Chapter 2 Wound strength, Chapter 3 Factors affecting healing, Chapter 4 Sutures and dressings, Chapter 5 Clinical trials, Chapter 6 Skin healing and burns, and Chapter 7 The abdominal wall, (1984). NPL–754.

Brubacher, L.L., "To heal a draining wound," RN, 45(3):30–36 (Mar. 1982). NPL–755.

Dahlin, P.A., et al., "Cerebrospinal fluid leak because of pressure sore fistula in a quadriplegic," Spine, 12(1):72–75, (1987). NPL–756.

Downie, P.A., ed., Cash's textbook of medical condiitons for physiotherapists, Chapter 1 Inflammation and healing, Chapter 2 Oedema, Chapter 19 Skin conditions, Chapter 20 Burns, B. Lippincott Co., (1979). NPL–757.

Ersh, Z. Ya., "Use of polyurethane foam for cleaning of purulent cavities and wounds," I.I. Grekov J. of Surg., 133(9):134–135 and additional sheets (10 sheets in English and 5 sheets in Russian) (1984). NPL–758.

Fasol, P., et al., "The foil vacuum dressing for the treatment of infected skin defects," Acta Chir. Austriaca 116–118, (2 sheets English and 3 sheets German) (1976). NPL–759.

"Heparin use may reduce restenosis risk," Aorn J., 46(3):456, (Sep. 1987). NPL–760.

Gruendemann, B.J., et al., Alexander's Care of the patient in surgery, 8th ed., C.V. Mosby Co., pp. 138–139 (1987). NPL–761.

Kirk–Othmer Encyclopedia of chemical technology, 3d ed., vol. 8, pp. 201–203 (1979). NPL–762.

Kostyuchenok, B.M., et al., "Vacuum treatment of purulent wounds," Soviet Medicine, pp. 18–21, (4 sheets English, 4 sheets Russian, with English abstract on last page), (1984). NPL–763.

Kuzin, M.I., et al., "Method of vacuum treatment of wounds," Wounds and Wound Infection, pp. 348–350, (2 sheets) (1981). NPL–764.

Kuzin, M.I., et al., "Vacuum treatment of a purulent wound," Wounds and Wound Infection, Handbook for Physicians, 2nd revised and supplemented ed., pp. 243–246, (3 sheets) (1990). NPL–765.

Tranchell, H.G., et al., Circulatory Ulcers A Physicial Approach, John Wright & Sons Ltd., Bristol, Foreword, I. Ulcers: a comparison, II. The ulcer, pp. 44–47, and 54–55, (1960). NPL–766.

Parish, L.C., et al., "The infected decubitus ulcer," Int. J. Dermatol., 28:643–647 (Dec. 1989). NPL–768.

Davydov, Y.A., et al., "Device and method for vacuum therapy of purulent lactation mastites," Khirurgiya, (4):131–132, (Apr. 1988). DV15.

Davidov, Y.A., et al., "Justifying the usage of forced early secondary sutures in treatment of purulent wounds by the vacuum therapy," Vestnik Chirugia 126–129, (2 sheets in English and 3 sheets in Russian) (Mar. 1990). DV16.

Davydov, Y.A., et al., "Pathogenic mechanisms of the effect of vacuum therapy on the course of the wound process," Khirurgiya, 6:42–47 (7 sheets English and 8 sheets Russian, with English abstract on pp. 46–47) (1990). DV17.

Davydov, Y.A., et al., "Bacteriological and cytological evaluation of vacuum therapy of purulent wounds", Vestnik khirurgii, 10:48–52, (5 sheets English, 5 sheets Russian, English abstract on pp. 52) (Received 1987). DV18.

Davydov, Y.A., et al., "Vacuum therapy in the treatment of purulent lactation mastitis," pp. 66–70 (5 sheets English, 5 sheets Russian, English abstract on pp. 70) (Received 1986). DV19.

EP 0 620 720 (DE 692 24 847), Medela brief, with English translation, with Exhibits 22, 23, 25, and 26, dated Mar. 6, 2009. DENA–WH1–011.

EP 0 620 720 (DE 692 24 847), Wake Forest brief in response to Medela's Mar. 6, 2009 brief, with English translation, and Exhibit Y: report of Dr. Christian Willy, brief dated Mar. 11, 2009. DENA–WH1–012.

EP 0 620 720 (DE 692 24 847), Wake Forest's Brief as filed with the Court, with Exhibits Z1–Z3, dated Mar. 16, 2009. DENA–WH1–014.

EP 0 688 189 (DE 694 25 881) Brief filed by Wake Forest Jan. 30, 2009. DENA–WH2–007.

KCI v. Medela, Case No. 08–cv–00087, (formerly 2:07cv187), Plaintiffs' opening preliminary claim construction brief, with Exhibit F, filed by KCI on May 15, 2009. SA087–024.

KCI, et al., v. Blue Sky Medical Group, Inc., et al., SA08–cv–102, (formerly 2:07cv188). Plaintiffs' opening claim construction brief, with Exhibit F, filed by KCI on May 15, 2009. SA102–031.

EP 0 688 189 (DE 694 25 881) Brief dated Jan. 20, 2009. DENA–WH2–009.

KCI, et al., v. Blue Sky Medical Group, Inc., et al., SA08–cv–102, (formerly 2:07cv188), Plaintiffs' reply in support of second supplement to memorandum in support of Plaintiffs' motion for a preliminary injunction, filed Jun. 17, 2009. SA102–047.

KCI, et al., v. Blue Sky Medical Group, Inc., et al., SA08–cv–102, (formerly 2:07cv188), Direct testimony of Rohit Kashyap, Ph.D. in support of Plaintiffs' motion for a preliminary injunction, dated Jun. 18, 2009. SA102–048.

KCI, et al., v. Blue Sky Medical Group, Inc., et al., SA08–cv–102, (formerly 2:07cv188), Direct testimony of James E. Malackowski in support of Plaintiffs' motion for a preliminary injunction, dated Jun. 18, 2009. SA102–049.

KCI, et al., v. Blue Sky Medical Group, Inc., et al., SA08–cv–102, (formerly 2:07cv188), Direct testimony of Dr. Dennis Paul Orgill, dated Jun. 18, 2009. SA102–050.

KCI, e al., v. Blue Sky Medical Group, Inc., et al., SA08–cv–102, (formerly 2:07cv188), Plaintiffs' motion to strike Defendant Smith & Nephew, Inc.'s Bagaoutdinov declaration, filed Jun. 18, 2009. SA102–051.

3M™ Inzisionsfolien—Produktubersicht, by 3M Medica, 6 annotated sheets. NPL–772.

Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III). NPL–773.

Buschbaum, H.J., ed., et al., Strategies in Gynecologic Surgery, pp. 203, Springer–Verlag, NY, (1986). NPL–774.

Flynn, J–B. McC., et al., Technological Foundations in Nursing, pp. 506–507, Appleton & Lange, Norwalk, CT, (1990). NPL–775.

GOMCO Mobile constant and intermittent model 6030 & 6031, Operation, Maintenance and Service Manual, with annotations, 21 sheets, (Jan. 1987). NPL–776.

Kahlson, G., et al., "Wound healing as dependent on rate of histamine formation," The Lancet, pp. 230–234, (Jul. 30, 1960). NPL–777.

Karev, I.D., et al., "Foam drainage system for treating purulent wounds," pp. 87–88, (2 sheets English translation, 2 sheets Russian and certification of translation dated Apr. 6, 2009) (allegedly dated 1986). NPL–778.

Kozier, B., et al., Techniques in Clinical Nursing, 3d ed., pp. 559–560, pp. 603–605, Addison–Wesley Publishing Company, Inc., Health Sciences, Redwood City, CA, (1989). NPL–779.

McLean, W. C., "The role of closed wound negative pressure suction in radial surgical procedures of the head and neck," The Laryngoscope, 74(1)70–94, (Jan. 1964). NPL–780.

Norton, B.A., et al., Skills for Professional Nursing Practice: communication, physical appraisal, and clinical techniques, pp. 298–302, pp. 328–329, Appleton–Century–Crofts, Norwalk, CT (1986). NPL–781.

Bagautdinov, N.A., Report on Practical Application entitled "Variant of vacuum treatment of purulent wounds," Kazan Municipal Hospital No. 8, (1 sheet in English 1 sheet in Russian and certificate of translation dated May 8, 2009), (allegedly dated Dec. 24, 1985). (Practical Report I) NPL–782.

Kuznetsov, V.A. et al., Report on Practical Application entitled "Method of vacuum–sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II) NPL–783.

Bagautdinov, N.A., Report on Practical Application entitled "Method of vacuum treatment of open purulent wounds," Medical–Sanitary Ward of the Arzamas Instrument Plant, (1 sheet in English, 1 sheet in Russian and certificate of translation dated Apr. 27, 2009) (allegedly dated 1986). (Practical Report III) NPL–784.

Roth, B., et al., "Ubersichtsarbeit: Indication for suction–rinse drainage and hygienic certainty in drainages," GMS Krankenhaushyg. Interdiszip, 1(1):Doc27 (7 sheets in German with English abstract on first sheet) (2006). NPL–785.

Schneider, F.R., Handbook for the Orthopaedic Assistant, 2nd ed., pp. 185, The C.V. Mosby Company, St. Louis, (1976). NPL–786.

Thomas, S., Wound Management and Dressings, Chapter 4: Semipermeable film dressings (continued onto pp. 26–34), Chapter 5: Foam dressings (continued onto pp. 36–42), and pp. 166, The Pharmaceutical Press, London, (1990). NPL–787.

Witkowski, J.A., et al., "Synthetic dressings: wound healing in the 80's," (5 sheets), Hospital Therapy, (Nov. 1986). NPL–788.

KCI, et al., v. Blue Sky Medical Group, Inc., et al., SA08–cv–102, (formerly 2:07cv188), Witness statement of Ian L. Gordon, M.D., Ph.D., dated Jun. 17, 2009 (certificate of service dated Jun. 18, 2009). SA102–052.

Davydov, Y.A., et al., "Vacuum therapy in the treatment of acute purulent diseases of soft tissues and purulent wounds", Vest. Khir. 141(9):43–46 (6 sheets English, 6 sheets Russian, English abstract on pp. 46) (1988). DV20.

EP 0 620 720 (DE 692 24 847), Decision of Federal Patent Court, in German with English translation, dated Mar. 17, 2009. DENA–WH1–018.

*KCI, et al., v. Blue Sky Medical Group, Inc., et al.*, SA08–cv–102, (formerly 2:07cv188), Second supplement to Defendant Smith & Nephew, Inc.'s opposition to Plaintiffs' motion for preliminary injunction, filed by S&N May 12, 2009. SA102–029.

*KCI, et al., v. Blue Sky Medical Group, Inc., et al.*, SA08–cv–102, (formerly 2:07cv188), Declaration of Nail A. Bagaoutdinov in support of Defendant Smith & Nephew, Inc.'s opposition to Plaintiffs' motion for a preliminary injunction, with Exhibits NB–01–NB–05, dated May 8, 2009, filed May 12, 2009. SA102–030.

*KCI, et al., v. Blue Sky Medical Group, Inc., et al.*, SA08–cv–102, (formerly 2:07cv188), Supplement to Exhibit A of Plaintiffs' infringement contentions, served by KCI on S&N May 15, 2009. SA102–032.

*KCI, et al., v. Blue Sky Medical Group, Inc., et al.*, SA08–cv–102, (formerly 2:07cv188), Supplement to Exhibit B of Plaintiffs' infringement contentions, served by KCI on S&N May 15, 2009. SA102–033.

*KCI, et al., v. Blue Sky Medical Group, Inc., et al.*, SA08–cv–102, (formerly 2:07cv188), Supplement to Exhibit C of Plaintiffs' infringement contentions, served by KCI on May 15, 2009. SA102–034.

*KCI, et al., v. Blue Sky Medical Group, Inc., et al.*, SA08–cv–102, (formerly 2:07cv188), Supplement to Exhibit D of Plaintiffs' infringement contentions, served by KCI on S&N May 15, 2009. SA102–035.

*KCI, et al., v. Blue Sky Medical Group, Inc., et al.*, SA08–cv–102, (formerly 2:07cv188), Deposition of Dr. Ian Gordon taken Apr. 29, 2009. SA102–036.

*KCI, et al., v. Blue Sky Medical Group, Inc., et al.*, SA08–cv–102, (formerly 2:07cv188), Deposition of Dr. Dennis Orgill taken Apr. 27, 2009. SA102–037.

*KCI, et al., v. Blue Sky Medical Group, Inc., et al.*, SA08–cv–102, (formerly 2:07cv188), Defendant's first supplemental preliminary invalidity contentions, filed by S&N Jun. 4, 2009. SA102–041.

*KCI, et al., v. Blue Sky Medical Group, Inc., et al.*, SA08–cv–102, (formerly 2:07cv188), S&N's invalidity contentions for US 7,216,651—First supplemental Exhibit A filed by S&N Jun. 4, 2009. SA102–042.

*KCI, et al., v. Blue Sky Medical Group, Inc., et al.*, SA08–cv–102, (formerly 2:07cv188), S&N's invalidity contentions for US 7,198,046—First supplemental Exhibit B filed by S&N Jun. 4, 2009. SA102–043.

*KCI, et al., v. Blue Sky Medical Group, Inc., et al.*, SA08–cv–102, (formerly 2:07cv188), S&N's invalidity contentions for US 5,636,643—First supplemental Exhibit C filed by S&N Jun. 4, 2009. SA102–044.

*KCI, et al., v. Blue Sky Medical Group, Inc., et al.*, SA08–cv–102, (formerly 2:07cv188), S&N's invalidity contentions for US 5,645,081—First supplemental Exhibit D filed by S&N Jun. 4, 2009. SA102–045.

*WFU v. S&N* (UK) Case No. HC08 C03563, Order entered May 1, 2009. SNUK–029.

*KCI v. Medela*, Case No. 08–cv–00087, (formerly 2:07cv187), Medela, Inc. and Medela AG's responsive claim construction brief with Exhibits E, F, and P, filed by Medela Jun. 5, 2009. SA087–026.

*KCI, et al., v. Blue Sky Medical Group, Inc., et al.*, SA08–cv–102, (formerly 2:07cv188), Defendant Smith & Nephew, Inc.'s responsive claim construction brief, with Exhibit 5, filed by S&N Jun. 5, 2009. SA102–039.

*KCI, et al., v. Blue Sky Medical Group, Inc., et al.*, SA08–cv–102, (formerly 2:07cv188), Defendant Smith & Nephew, Inc.'s response to KCI's second supplement to its motion for preliminary injunction, filed by S&N Jun. 9, 2009. SA102–038.

EP 0 688 189 (DE 694 25 881) Brief filed by Medela (with English translation) and Enclosures NK16, dated Apr. 27, 2009. DENA–WH2–008.

EP 0 620 720 (DE 692 24 847), English translation of the Decision of the Federal Patent Court dated Mar. 17, 2009, full translation by Vossius & Partner. DENA–WH1–019.

Excerpts from Bier's Hyperemic Treatment, pp. 17–25, 44–46, 90–96, 167–170, 210–211 (1909). NPL–767.

*KCI, et al., v. Blue Sky Medical Group, Inc., et al.*, SA08–cv–102, (formerly 2:07cv188), Second joint supplement to preliminary injunction briefing with attached opinion, filed Jun. 4, 2009. SA102–040.

*KCI v. Medela*, Case No. 08–cv–00087, (formerly 2:07cv187), Joint claim construction and prehearing statement, filed May 8, 2009. SA087–022_SA102.

*KCI v. Medela*, Case No. 08–cv–00087, (formerly 2:07cv187), Exhibit B (parts 1, 2, and 3) to Joint claim construction and prehearing statement, filed May 8, 2009. SA087–025_SA102.

*KCI v. Medela*, Case No. 08–cv–00087, (formerly 2:07cv187), Declaration of Dr. Dennis Paul Orgill in support of claim construction, with Exhibit DO–1, dated Apr. 24, 2009. SA087–023.

*KCI, et al., v. Blue Sky Medical Group, Inc., et al.*, SA08–cv–102, (formerly 2:07cv188), Declaration of Dr. Dennis Paul Orgill in support of claim construction, with Exhibits DO–1 and DO–7, dated Apr. 24, 2009. SA102–028.

Chariker, M.E., et al., "An algorithmic approach to the use of gauze–based negative–pressure wound therapy as a bridge to closure in pediatric extremity trauma," Plast. Reconstr. Surg., 123:1510–1520, (2009). NPL–771.

*KCI, Inc., et al., v. Convatec, Inc., et al.*, 1:08–cv–00918, Plaintiffs' infringement contentions in response to interrogatory No. 1 of Defendants' first set of interrogatories (Nos. 1–3), filed by KCI, Jun. 1, 2009. MDNC918–002.

*KCI, Inc., et al., v. Convatec, Inc., et al.*, 1:08–cv–00918, Exhibit A of Plaintiffs' infringement contentions in response to interrogatory No. 1 of Defendants' first set of interrogatories (Nos. 1–3)—Chart identifying where each element of each asserted claim of the 7,216,651 patent is found in the Engenex System, filed by KCI Jun. 1, 2009. MDNC918–003.

*KCI, Inc., et al., v. Convatex, Inc., et al.*, 1:08–cv–00918, Exhibit B of Plaintiffs' infringement contentions in response to interrogatory No. 1 of Defendants' first set of interrogatories (Nos. 1–3)—Chart identifying where each element of each asserted claim of the 7,198,046 patent is found in the Engenex System, filed by KCI Jun. 1, 2009. MDNC918–004.

*KCI, Inc., et al., v. Convatec, Inc., et al.,* 1:08–cv–00918, Exhibit C of Plaintiffs' infringement contentions in response to interrogatory No. 1 of Defendants' first set of interrogatories (Nos. 1–3)—Chart identifying where each element of each asserted claim of the 5,636,643 patent is found in the Engenex System, filed by KCI Jun. 1, 2009. MDNC918–005.

*KCI, Inc., et al., v. Convatec, Inc., et al.,* 1:08–cv–00918, Exhibit D of Plaintiffs' infringement contentions in response to interrogatory No. 1 of Defendants' first set of interrogatories (Nos. 1–3)—Chart identifying where each element of each asserted claim of the 5,645,081 patent is found in the Engenex System, filed by KCI Jun. 1, 2009. MDNC918–006.

*KCI, et al., v. Blue Sky Medical Group, Inc., et al.,* SA08–cv–102, (formerly 2:07cv188), Plaintiffs' second supplement to memorandum in support of Plaintiffs' motion for a preliminary injunction, with Ex. 27, filed by KCI May 22, 2009. SA102–046.

EP 03756228.7 Supplemental European Search Report—P02915EP0–SR (May 26, 2009).

*WFU & KCI v. S&N,* VID 143, (Regarding Au 674837) Federal Court of Australia, Order by Judge Ryan, including reasons for judgment, dated Jun. 15, 2009. AU143–001.

*KCI, et al., v. Blue Sky Medical Group, Inc., et al.,* SA08–cv–102, (formerly 2:07cv188), Plaintiffs' motion to strike portions of the witness statement of Ian L. Gordon, filed by KCI Jun. 9, 2009. SA102–053.

*KCI, et al., v. Blue Sky Medical Group, Inc., et al.,* SA08–cv–102, (formerly 2:07cv188), Plaintiffs' motion to strike defendant Smith & Nephew Inc.'s foreign declarations, with Exhibit C (Declaration of Edward A. Betancourt dated Nov. 3, 2006), filed by KCI Jun. 19, 2009. SA102–054.

*KCI, et al., v. Blue Sky Medical Group, Inc., et al.,* SA08–cv–102, (formerly 2:07cv188), Letter to Judge Furgeson, Jr., filed by KCI Jun. 26, 2009. SA102–055_SA087.

*KCI, et al., v. Blue Sky Medical Group, Inc., et al.,* SA08–cv–102, (formerly 2:07cv188), Plaintiffs' supplement to opening claim construction brief, with Declaration of Joel Fischer dated Jun. 26, 2009 and Exhibit 1: Memo dated Jan. 30, 2009 from Mocon; filed by Jun. 28, 2009. SA102–056_SA087.

Demorest, R.L., "New standards in water vapour permeability testing," British Plastics & Rubber, 3 sheets, (handwritten label on first sheet shows "Exhibit TT"), (May 1995). NPL–789.

Roy, J.N., "Vaseline oil in the dressing of the radical mastoid operation," J. Laryngology, pp. 585–590, (Nov. 1907). NPL–790.

Blake, J.B., "The use of sterile oil to prevent intraperitoneal adhesions: A clinical and experimental study," Transactions of the American Surgical Association, pp. 383–390, (Jun. 1908). NPL–791.

Wilkie, D.P.D., et al., "The use of oil in abdominal surgery," Surgery, Gynecology and Obstetrics, pp. 126–132 (1910). NPL–792.

Thomas, S., "Wound Management and Dressings," The Pharmaceutical Press, London, 223 sheets, (1990). NPL–793.

Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975). NPL–797.

Turner, T.D., ed., et al., Advances in Wound Management, including "The role of foam dressings in wound management" by S. Thomas, "Clinical aspects of Synthaderm®", by T. Martin, et al., "Lyofoam®—Used in the treatment of leg ulcers" by J. Creevy, and "Clinical experience of Silastic® foam dressing," by K.G. Harding; John Wiley & Sons, 17 sheets, (Proceedings dated Mar. 20–21, 1985) (1986). NPL–798.

*KCI, et al., v. Blue Sky Medical Group, Inc., et al.,* SA08–cv–102, (formerly 2:07cv188), Plaintiffs' second supplement to opening claim construction brief, with Supplemental declaration of J. Fischer, dated Jul. 10, 2009, filed by KCI Jul. 10, 2009. SA102–057_SA087.

Request for Ex Parte Reexamination of U.S. Patent No. 5,645,081, requested Jun. 3, 2008. EPRE–001.

Exhibits to Request for Ex Parte Reexamination of U.S. Patent No. 5,645,081, requested Jun. 3, 2008. EPRE–002.

Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of Index card, 1 sheet Russian, certification dated May 7, 2008) (1986). NPL–697.

Zivadinovic, G., et al., "Vacuum therapy in the treatment of peripheral blood vessels," Conference Papers of the 5th Timok Medical Days, Majdanpek, No. 3–4, pp. 161–164, (5 sheets English translation; 5 sheets in Serbian, certification dated May 9, 2008) (1986). NPL–691.

Chardak, W.M., et al., "Experimental studies on synthetic substitutes for skin and their use in the treatment of burns," Ann. Surg., 155(1):127–139, (Jan. 1962). NPL–698.

Fujimori, R., et al., "Sponge fixation method for treatment of early scars," Plast. & Reconst. Surg., 42(4):322–326, (Oct. 1968). NPL–699.

Kirk–Othmer, Encyclopedia of Chemical Technology, 2nd completely revised edition, vol. 14, pp. 227, John Wiley & Sons, Inc., (1967). NPL–700.

Meyer, W., et al., excerpts from "Bier's Hyperemic Treatment", W.B. Saunders and Co., (47 sheets) (1908). NPL–702.

*KCI v. BlueSky,* Transcript of Deposition of Jeffrey A. Neizgoda, M.D., with Exhibits, dated May 1, 2006, parts 1–24 of 50. BS–94.

Kuznetsov, V.A., et al., Report on Practical Application entitled "Method of vacuum–sorption treatment of purulent wounds," Kazan Municipal Hospital No. 8, (1 sheet in English, 1 sheet in Russian and certificate of translation dated Apr. 28, 2009), (allegedly dated May 19, 1986), NPL–800.

P. Svedman et al., A Dressing System Providing Fluid Supply and Suction Drainage Used for Continuous or Intermittent Irrigation, Annals of Plastic Surgery, vol. 17, No. 2, Aug. 1986, pp. 125–133.

P. Svedman et al., A Dressing Allowing Continuous Treatment of a Biosurface, IRCS Medical Science: Biomedical Technology; Clinical Medicine; Surgery and Transplantation, vol. 7, Mar. 1979, p. 221.

Steven D. Chinn et al., *Closed Wound Suction Drainage*, the Journal of Foot Surgery, vol. 24, No. 1, 1985, pp. 76–81.

*Medela, Inc. v. Kinetic Concepts, Inc., et al.,* Case No. 7cv449 in the United States District Court Western District of Texas San Antonio Division, Complaint for Declaratory Judgment, filed by Medela Inc. on May 22, 2007. SA449–001.

*Medela v. KCI,* Case No. 7cv449, Opposed motion to dismiss, or in the alternative, motion to transfer case, with exhibits 2–4 and proposed order, filed by KCI on Jul. 13, 2007. SA449–002.

*Medela v. KCI,* Case No. 7cv449, Answer to Complaint for Declaratory Judgment, filed by KCI on Jul. 13, 2007. SA449–003.

*Medela v. KCI,* Case No. 7cv449, Response to motion to dismiss, with Declaration and Exhibits B–G, filed by Medela, Inc. on Aug. 3, 2007. SA449–004.

*Medela v. KCI,* Case No. 7cv449, Reply to response to motion to transfer, filed by KCI on Aug. 17, 2007. SA449–005.

*Medela v. KCI,* Case No. 7cv449, Order staying defendants' motion entered Oct. 11, 2007. SA449–006.

*Blue Sky Medical Group, Inc., et al., v. Kinetic Concepts, Inc. et al.,* Case No. 7cv454 in the United States District Court Western District of Texas San Antonio Division, Complaint for Declaratory Judgment and cover sheet, filed by Blue Sky on May 23, 2007. SA454–001.

*Blue Sky v. KCI,* Case No. 7cv454, First Amended and Supplemental Complaint for Declaratory Judgment, filed by Blue Sky on Jul. 12, 2007. SA454–002.

*Blue Sky v. KCI,* Case No. 7cv454, Motion to dismiss , or in the alternative, motion to transfer case, with proposed order and exhibits 2–4, filed by KCI on Aug. 1, 2007. SA454–003.

*Blue Sky v. KCI,* Case No. 7cv454, Answer to first amended complaint with jury demand, filed by KCI on Aug. 1, 2007. SA454–004.

*Blue Sky v. KCI,* Case No. 7cv454, Response in opposition to motion to dismiss, or in the alternative motion to transfer case, with exhibits A–G and proposed order, filed by Blue Sky on Aug. 16, 2007. SA454–005.

*Blue Sky v. KCI,* Case No. 7cv454, Reply to response to motion, filed by KCI on Aug. 30, 2007. SA454–006.

*Blue Sky v. KCI,* Case No. 7cv454, Order staying defendant's motion pending the outcome of Blue Sky's motion regarding opposed motion to dismiss or in the alternative, motion to transfer case, entered Oct. 11, 2007. SA454–007.

*Innovative Therapies, Inc., v. Kinetic Concepts, Inc., et al.,* Case No. 07–cv–00589 in the United States District Court for the District of Delaware, Complaint filed with jury demand, cover sheet and acknowledgement of consent form, filed by ITI on Sep. 25, 2007. DED–001.

*ITI v. KCI,* Case No. 07–589, Motion to dismiss for lack of jurisdiction over the subject matter, proposed order, opening brief in support of motion, and declarations, filed by KCI on Oct. 15, 2007. DED–002.

*ITI v. KCI,* Case No. 07–589, Stipulation to extend time regarding briefing schedule on defendant's motion to dismiss and certificate of service, filed by ITI on Oct. 23, 2007, Order Entered Oct. 26, 2007. DED–003.

*Kinetic Concepts, Inc., et al. v. Medela AG et al.,* Case No. 2:07cv187 in the United States District Court Eastern District of Texas Marshall Division, Complaint with request for jury trial with cover sheet, filed by KCI on May 15, 2007. MDIV187–001.

*KCI v. Medela,* Case No. 2:07cv187, Answer to complaint and counterclaim, filed by Medela Inc. on Jul. 10, 2007. MDIV187–002.

*KCI v. Medela,* Case No. 2:07cv187, Motion to change venue, with proposed order and exhibits, filed by Medela, Inc. on Jul. 10, 2007. MDIV187–003.

*KCI v. Medela,* Case No. 2:07cv187, Motion to dismiss for lack of personal jurisdiction, with proposed order and exhibits A–C, filed by Medela AG on Jul. 11, 2007. MDIV187–004.

*KCI v. Medela,* Case No.1 2:07cv187, Response to motion to change venue, with proposed order and exhibits, filed by KCI on Aug. 1, 2007. MDIV187–005.

*KCI v. Medela,* Case No. 2:07cv187, Answer to Counterclaim, filed by KCI on Aug. 2, 2007. MDIV187–006.

*KCI v. Medela,* Case No. 2:07cv187, Response in opposition to motion to dismiss for lack of personal jurisdiction, with proposed order, index, and exhibits, filed by KCI on Aug. 2, 2007. MDIV187–007.

*KCI v. Medela,* Case No. 2:07cv187, Reply to response to motion to change venue, with exhibit, filed by Medela, Inc. on Aug. 13, 2007l. MDIV187–008.

*KCI v. Medela,* Case No. 2:07cv187, Reply to motion to dismiss for lack of personal jurisdiction, with exhibits, filed by Medela AG on Aug. 13, 2007. MDIV187–009.

*KCI v. Medela,* Case No. 2:07cv187, Surreply to reply to response to motion to change venue, filed by KCI on Aug. 23, 2007. MDIV187–010.

*KCI v. Medela,* Case No. 2:07cv187, Surreply to reply to response to motion to dismiss for lack of personal jurisdiction, with exhibits, filed by KCI on Aug. 23, 2007. MDIV187–011.

*Kinetic Concepts, Inc., et al. v. Blue Sky Medical Corporation, et al.,* Case No. 2:07cv188 in the United States District Court Eastern District of Texas Marshall Division, Complaint with request for jury trial, with cover sheet, filed by KCI on May 15, 2007. MDIV188–001.

*KCI v. Blue Sky,* Case No. 2:07cv188, Amended Complaint with request for jury trial and Request for Declaratory Judgment, with exhibit A, filed by KCI on May 15, 2007. MDIV188–002.

*KCI v. Blue Sky,* Case No. 2:07cv188, Answer to Amended Complaint, with Counterclaim, filed by Blue Sky on Jul. 10, 2007. MDIV188–003.

*KCI v. Blue Sky,* Case No. 2:07cv188, Motion to dismiss for lack of jurisdiction, with proposed order, corrected proposed order and exhibits A–E, filed by Smith & Nephew Holdings, Inc., Smith & Nephew, PLC on Jul. 13, 2007. MDIV188–004.

*KCI v. Blue Sky,* Case No. 2:07cv188, Motion to change venue, with proposed order, corrected proposed order and exhibits 1, 4–9, 11, 12, filed by Blue Sky on Jul. 23, 2007. MDIV188–005.

*KCI v. Blue Sky,* Case No. 2:07cv188, Answer to counterclaim filed by KCI on Aug. 2, 2007. MDIV188–006.

*KCI v. Blue Sky,* Case No. 2:07cv188, Response in opposition to motion to dismiss for lack of jurisdiction, with proposed order and exhibits 1–7, filed by KCI on Aug. 6, 2007. MDIV188–007.

*KCI v. Blue Sky,* Case No. 2:07cv188, Response in opposition to motion to change venue, filed by KCI on Aug. 7, 2007. MDIV188–008.

*KCI* v. *Blue Sky*, Case No. 2:07cv188, Reply in support of motion to dismiss for lack of personal jurisdiction, filed by Smith & Nephew Holdings, Inc., Smith & Nephew, PLC on Aug. 16, 2007. MDIV188–009.
*KCI* v. *Blue Sky*, Case No. 2:07cv188, Response to motion to change venue, with exhibits 13–15, filed by Blue Sky on Aug. 16, 2007. MDIV188–010.
*KCI* v. *Blue Sky*, Case No. 2:07cv188, Surreply to reply to response to motion to dismiss for lack of jurisdiction, filed by KCI on Aug. 28, 2007. MDIV188–011.
*KCI* v. *Blue Sky*, Case No. 2:07cv188, Surreply to reply to response to motion to change venue, filed by KCI on Aug. 28, 2007. MDIV188–012.
Svedman, P., et al., "Staphylococcal wound infection in the pig: Part I. Course," Ann. Plast. Surg., 23(3):212–218, (Sep. 1989). NPL–684.
Sanden, G., et al., "Staphylococcal wound infection in the pig: Part II: Inoculation, quantification of bacteria and reproducibility," Ann. Plast. Surg., 23(3):219–223, (Sep. 1989). NPL–685.
*ITI* v. *KCI*, Case No. 07–589, Plaintiff's answering brief in opposition to defendants' motion to dismiss, with exhibits, filed by ITI on Nov. 14, 2007. DED–004.
M. Gosta Arturson, *The Pathophysiology of Severe Thermal Injury, JBCR*, 6(2):129–146 (Mar.–Apr.) 1985. NPL–020.
R. A.F. Clark et al., The Molecular and Cellular Biology of Wound Repair, Chapter 1 (1988) NPL–085.
Jeter, K.F. et al. (eds.), "Managing Draining Wounds and Fistulae: New and Established Methods," Chronic Wound Care: Health Management Publications, 1990, pp. 240–246. NPL–223.
Aeros, "Moblvac II." NPL–004.
Aeros, Aeros Instruments, Inc. 1111 Lakeside Drive, Gurnee, IL 60031, Aug. 1993. "Care–E–Vac." NPL–005.
Emerson, Series 55. J. H. Emerson Co., 22 Cottage Park Ave., Cambridge, MA 02140. "Emerson Post–Operative Suction Pumps." NPL–139.
Emerson, J. H. Emerson Co., (address: same as above). "Emerson Transport Suction Unit." NPL–138.
Aeros, Aeros Instruments, Inc. 3411 Commercial Ave., Northbrook, IL 60062. Oct. 1988. Part No. 1504–02 7M. "Instavac Aspirator." NPL–006.
"Pleur–evac. Adult–Pediatric, Non–Meterd." Code No. A–4000. Control No. F7961J. NPL–333.
Instruction Manual, Creative Medical Laboratories, Inc. P.O. Box 6347, Rochester, Minn. 55903. "TUGS" (Transportable Universal Gradient Suction). NPL–221.
Deknatel, Div. of Howmedica, Inc. Quenns Village, NY 11429. "Pleur–evac." NPL–111.
Sparta Instrument Corp. 26602 Corporate Ave., Hayward, CA 94545. "Power Source Multi–Purpose Surgical Aspirator." NPL–383.
Wells Johnson Company, 2045 N. Forbes Blvd., Suite 106, Tuscon, AZ. "Point 5 Aspirator." NPL–433.
Microtek Heritage, Inc. P.O. Box 2487, Columbus, MS 39704. "Wound–Evac ET." NPL–284.
Fleischmann, W. *Wund Forum Spezial*. IHW '94. "Vakuumversiegelung zur Behandlung von Probelmwunden" (with English translation: "Vacuum sealing for Treatment of Problematical Wounds." NPL–160.
Fleischmann, W. *Acta Orthopaedica Belgica*. vol. 58, Suppl. I–1992 "Treatment of Bone and Soft Tissue Defects in Infected Nonunion." NPL–159.

Fleischmann, W. Strecker W. Bombelli M, Kinzi L. *Unfall Chirurg*. Springer–Variag 1993. 96:488–92 "Vakuumversiegelung zur Behandlung des Weichteilschadens bei offenen Frakturen." with English translation [Vacuum sealing as treatment of soft tissue damage in open fractures]. [German] NPL–157.
Valenta, A.L. *American Journal of Nursing*. Apr. 1994. "Using the Vacuum Dressing Alternative for Difficult Wounds." 94:44–5 NPL–414.
Bier, A., "Hyperemia by Suction Apparatus" Chapter VIII, Hyperemia as a Therapeutic Agent, Chicago, IL, Roberts Publishing, 74–85, (1905). NPL–216.
Saunders, J. W., The Lancet, pp. 1286–1287, Jun. 28, 1952, "Negative–Pressure Device for Controlled Hypotension during Surgical Operations" NPL–356.
Landis, et al., Robinette Foundation of the Hospital of the University of Pennsylvania, "The Effects of Alternate Suction and Pressure on Blood Flow to the Lower Extremities" (Sep. 1933). NPL–249.
Hargens et al., Space Physiology Laboratory, Life Science Division, NASA Ames Research Center, "Control of Circulatory Function in Altered Gravitational Fields" (Feb. 1992). NPL–189.
Wolthius et al, Physiological Reviews, 54: 566–595, Jul. 1974, "Physiological Effects of Locally Applied Reduced Pressure in Man" NPL–441.
Viljanto et al., Br. J. Surg., 63: 427–430, 1976, "Local Hyperalimentation of Open Wounds" NPL–419.
Dillon, R. Angiology—The Journal of Vascular Diseases, pp. 47–56, Jan. 1986, "Treatment of Resistant Venous Stasis Ulcers and Dermatitis with the End–Diastolic Pneumatic Compression Boot" NPL–118.
Lundvall et al., Acta Physiol Scand, 136: 403–409, accepted Jan. 28, 1989, "Transmission of externally applied negative pressure to the underlying tissue. A study on the upper arm of man" NPL–262.
Klemp et al., The Journal of Investigative Dermatology, pp. 725–726 (1989), "Subcutaneous Blood Flow in Early Male Pattern Baldness" NPL–236.
A. Harle, Z. Orthop., 127: 513–517 (1989), "Schwachstellen herkomlicher Drainagen" with English Translation. NPL–192.
Dunlop et al., Br. J. Surg., 77: 562–563 (1990), "Vacuum drainage of groin wounds after vascular surgery: a controlled trail". NPL–125.
Maddin et al., International Journal of Dermatology, 29: 446–450 (1990), "The Biological Effects of a Pulsed Electrostatic Field with Specific Reference to Hair: Electrotrichogenesis" NPL–263.
Nakayama et al., Ann. Plast. Surg., 26:499–502 (1991), "A New Dressing Method for Free Skin Grafting in Hands" NPL–307.
Hargens et al., Aviation, Space and Environmental Medicine, pp. 934–937, Oct. 1991, "Lower Body Negative Pressure to Provide Load Bearing in Space" NPL–188.
Author unknown, Science, Sep. 1992, p. 42, "The Not–So–Bald–Truth" NPL–022.
Techno Takatsuki Co., Ltd., 8–16 Hatchonishimachi, Takatsuki City, Osaka, Japan, "HiBlow Air Pump" NPL–399.
Wells Johnson Company, 2045 N. Forbe Blvd., Suite 106, Tucson, AZ, "Suction Tips" NPL–432.
Industrial Equipment News, P.O. Box 1158, Skokie, IL 60076–9786, "Miscellaneous Equipment" NPL–218.

Letsou et al. "Stimulation of Adenylate Cyclase Activity in Cultured Endothelial Cells Subjected to Cyclic Stretch." Cardiovascular Surgery 3. Toronto. Sep. 1989. 634–639. NPL–253.

Bucalo et al. "Inhibition of Cell Proliferation by Chronic wound Fluid." Wound Repair and Regeneration. 181–186 Jul. 1993 NPL–065.

Falanga, Vincent. "Growth Factors and Chronic Wounds: The need to Understand the Microenvironment." Journal of Dermatology, Bol. 19: 667–672.

Urschel et al. "The Effect of Mechanical Stress on Soft and Hard Tissue Repair; a Review." British Journal of Plastic Surgery. 41, 182–186. 1988. NPL–411.

Gogia, Prem P. "The Biology of Wound Healing." Ostomy/Wound Management. Nov.–Dec. 1992. pp. 12, 14–16, 18–20, 22 NPL–172.

Wysocki et al. "Wound Fluid from Chronic Leg Ulcers Contains Elevated Levels of Metalloproteinases MMP–2 and MMP–9." The Society for Investigative Dermatology, Inc. Jul. 1993. 64–68 NPL–450.

Olenius et al. "Mitotic Activity in Expanded Human Skin." Plastic and Reconstructive Surgery. Feb. 1993. 213–216. NPL–318.

Mulder, G. D. et al. (eds.), *Clinicians' Pocket Guide to Chronic Wound Repair*, (Spartanburg, SC. Wound Healing Publications), 1991, pp. 54–55. NPL–317.

Chariker, M. E. et al. (eds), "Effective Management of Incisional and Cutaneous Fistulae with Closed Suction Wound Drainage," Contemporary Surgery, vol. 34, Jun. 1989, pp. 59–63. NPL–073.

Rastgeldi, S.: I. Pressure Treatment of Peripheral Vascular Diseases. II. Intermittent Pressure Treatment of Peripheral Vascular Disease. Opuscula Medica, Suppl. XXVII, 1972. NPL–343.

OP–Journal Nr. 3, Jahr. 6, Dec. 1990, pp. 31–35 W. Fleischmann, M. Mentzel, L. Kinzl "BWS, Gefahren und Komplikationen der Therapie" with English Trans. NPL–156.

Zumtobel et al., (1991) "Wunddrainage in der Elektiveund Notfallchirurgie" Wolfgang Pabst Verlag, relevant p. 12, left column. English Translation attached. NPL–455.

Saechtling, Kunststoff–Taschenbuch, 24. Ausgabe 1989, S. 439, 477. English Translation attached. NPL–350.

Mutschler, W. Bakker D. J., "Temporarer Hautersautz", ZFA 1989, Heft 24, S. 714–720 als Sonderdruck. English Translation attached. NPl–305.

W. Fleischmann, U. Becker, M. Bischoff, H. Hoekstra, "Vacuum sealing: indication, technique, and results", Eur. J. Orthop & Traumato (1995) 5;37–40. NPL–158.

Argenta LC, Morykwas MJ. Vacuum–assisted closure: a new method for wound control and treatment: clinical experience. Ann Plast Surg 1997;38: 563–577 WFU–31.

Morykwas MJ, Argenta LC, Shelton–Brown EI, McGuirt W. Vacuum–assisted closure: a new method for wound control and treatment: animal studies and basic foundation. Ann Plast Surg 1997; 38:553–62 WFU–29.

Davydov IA, Larichev AB, Smimov AP, Flegontov VB, Vakuum–terapiia v lechenii ostrykh gnoinykh zabolevanii miagkikh tkanei I gnoinyky ran. [Vacuum therapy of acute suppurative diseases of soft tissues and suppurative wounds]. Russian Vestnik Khirurgii Imeni I—I—Grekova 1988; 141: 43–6 with Eng. Trans. DV10.

Davydov IA, Abramov AI, Larichev AB. Vakuum–terapiia v preduprezhdenii posleoperatsionnoi ranevol infektsil. [Vacuum therapy in the prevention of postoperative wound infection]. Russian Vestnik Khirurgii Imen I—I—Grekov 1991; 147:91–5, with English Translation. DV12.

Iankov NI. Simuliatsiia konsolidatsil perelomov nizhnei cheliusti vaktuumnoi terapiei. [Stimulation of consolidation of mandibular fractures by means of vacuum therapy] Russian. Stomatologiia 1971; 50: 86, with Eng. Trans. NPL–217.

Inoiatov IM, Aleksandrov VB. Lechenie–promezhnostnoi rany posle amputatsii priamoi kishki vakuum–aspiratsie. [Vacuum aspiration in the treatment of the perineal wound following extirpation of the rectum]. Russian. Khirurgiia 1971; 47: 74–8, with English Translation. NPL–220.

Kochnev VA. Primenenie vakuum–drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian. Voprosy Onkologii 1967; 13:102–5, w/Eng. Trans. NPL–239.

Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia I Protezirovanie 1966;27:19–22, with English Translation. NPL–291.

Mirazimov BM, Vasina TA, Mezhericher MI, mikroflora dlitel'no nekazhivaiushchikh ran i effektivnost' metoda vakuumirovaniia. [Microflora of prolonged non–healing wounds and the effectiveness of the vacuum evaporative method]. Russian. Khirugiia 1967; 43: 40–3, with English Translation. NPL–290.

Mirazimov BM. Vorbereitung von Wunden und Geschwuren zur Hautplastik unter Anwendung der Vakuumierung [Preparation of wounds and abcessses for dermatoplasty by means of a vacuum device]. German. Beitrage zur Orthopadie und Traumatologie. 1967; 14:224–30, with Eng. Translation. NPL–292.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411–5, w/Eng. Trans. NPL–311.

Volkov LA. Ispol'zovanie vakuum–drenazhnoi sistemy v khirurgicheskoi praktike. [Use of vacuum–drainage system in surgical practice]. Russian. Klinicheskaia Khirurgiia. 1973;7:54–5, with English Translation. NPL–423.

Teder H, Sanden G, Svedman P. Continuous Wound Irrigation in the Pig, J Invest Surg 1990;3;339–407 NPL–400.

Nakayama Y, Tomotari I, Soeda S. A New Method for the Dressing of Free Skin Grafts. Plast Reconstr Surg 1990;86:1216–1219 NPL–308.

Brock WB, Barker DE, Burns RP. Temporary Closure of open abdominal wounds: the vacuum pack. Amer Surg 1995;61:30–5 NPL–059.

Shein M, Saadia R, Jameson JR, Decker GAG. The "sandwich technique" in the Management of the Open Abdomen. Br J Surg 1986;73:369–70 NPL–363.

Broome A. Hansson L, Lundgren F, Smedberg S. Open Treatment of Abdominal Septic Catastrophies. World J. Surg 1983;7:792–6 NPL–061.

Vatanasapt V, Areemit S, Jeeravipoolvam P, et al. Red rubber bulb, cheap and effective vacuum drainage. Journal of the Medical Association of Thailand 1989;72:193–7 NPL–417.

Brummelkamp WH, Taat CW, Slors JF. High–vacuum drainage and primary perineal wound closure in abdominoperineal excision of the rectum. Netherlands Journal of Surgery 1991;43:236–9 NPL–063.

Morykwas J, Argenta LC. Nonsurgical modalities to enhance healing and care of soft tissue wounds. Journal of the Southern Orthopaedic Association 1997;6:279–88 WFU–04.

Sames CP. Sealing of wounds with vacuum drainage [letter] Br Med J 1977;2:1123 NPL–353.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255 NPL–087.

Greer SE, Longaker MT, Margiotta M, Matthews AJ, Kasabian A. The Use of Subatmospheric Pressure Dressing for the Coverage of Radial Forearm Free Flap Donor–Site Exposed Tendon Complications. Ann Plast Surg 1999;43:551–554 NPL–179.

Greer SE, Duthie E, Cartolano B, Koehler KM, Maydick–Youngberg D, Longaker MT. Techniques for Applying Subatmospheric Pressure Dressing to Wounds in Difficult Regions of Anatomy. JWOCN 1999;26:250–3 NPL–177.

Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687 NPL–178.

Genecov DG, Schneider AM, Morykwas MJ, et al. A Controlled subatmospheric pressure dressing increases the rate of skin graft donor site reepithelialization. Ann Plast Surg 1998;40:219–25 WFU–28.

Mendez–Eastman S. Negative pressure wound therapy. Plastic Surgical Nursing 1998;18:27–9, 33–37 NPL–277.

Banwell P. Withey S, Holten I. The use of negative pressure to promote healing [letter; comment]. Brit J Plast Surg 1998;51:79 NPL–033.

Blackburn J H Boemi L, Hall WW. et al. Negative–pressure dressings as a bolster for skin grafts. Ann Plast Surg 1998;40:453–7 NPL–049.

Smith LA, Barker DE, Chase CW, et al. Vacuum Pack Technique of Temporary Abdominal Closure: A Four–Year Experience. Amer Surg 1997;63:1102–8 NPL–378.

McCulloch JM, Kemper CC. Vacuum–Compression Therapy for the Treatment of an Ischemic Ulcer. Physical Therapy 1993;73:165–9 NPL–270.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194–9 NPL–302.

Mirazimov, B.M.: Free Skin Grafting of Wounds and Ulcers using the "Vacuum Treatment" Method. [Orthop. Travmatol. Protez., 28(1):54–58.] with English Trans. 1967 NPL–293.

Greer, Steven E., "Whither Subatmospheric Pressure Dressing?" The Institute of Reconstructive Plastic Surgery, The New York University Medical Center, New York, NY Apr. Issue of Annals of Plastic Surgery 2000. NPL–180.

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996 NPL–344.

Hidden Interest—A Special Report.; When Physicians Double as Entrepreneurs. The New York Times. 11pp. Nov. 30, 1999 NPL–133.

Defranzo, Anthony J., et al., "Vacuum–Assisted Closure for the Treatment of Degloving Injuries." Plastic and Reconstructive Surgery 104 (7) 2145–48: (1999). WFU–35.

Morykwas, Michael J., et al., "Use of Subatmospheric Pressure to Prevent Progression of Partial–Thickness Burns in a Swine Model". Journal of Burn Care & Rehabilitation 20 (1 Part 1): 15–21 (1999) WFU–03.

Morykwas, Michael J., et al., "Use of Subatmospheric Pressure to Prevent Doxorubicin Extravasation Ulcers in a Swine Model". Journal of Surgical Oncology 72:14–17 (1999). WUF–33.

Molnar, Joseph A., et al., "Single–Stage Approach to Skin Grafting the Exposed Skull". Plastic and Reconstructive Surgery 105(1): 174–177 (2000). WFU–32.

Schneider, Andrew M., et al., "A New and Reliable Method of Securing Skin Grafts to the Difficult Recipient Bed". Plastic and Reconstructive Surgery 102(4) 1195–98 (1998). WFU–30.

Rosser, Charles J., et al., "A New Technique to Manage Perineal Wounds". Infections in Urology 1392) 45–47, 56 (2000). WFU–34.

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41–44, 46–50 (1999). NPL–330.

Meara, John G., et al., "Vacuum–Assisted Closure in the Treatment of Degloving Injuries". Annals of Plastic Surgery 42(6) 589–594 (1999). NPL–273.

Obdeijn, Miryam C., et al., "Vacuum–Assisted Closure in the Treatment of Poststernotomy Mediastinitis". Ann Thorac Surgery 68 2358–60 (1999). NPL–315.

Mendez–Eastman, Susan, "When wounds won't heal". RN 20–24 (1998) NPL–282.

Hartnett, Jacqueline M., "Use of Vacuum–Assisted Wound Closure in Three Chronic Wounds". JWOCN 25 (6) 281–290 (1998). NPL–195.

Mendez–Eastman, Susan., "Use of Hyperbaric Oxygen and Negative Pressure Therapy in the Multidisciplinary Care of a Patient with Nonhealing Wounds". JWOCN 26(2) 67–76 (1999). NPl–281.

Wooding–Scott, Margaret e al., "No–Wound is Too Big For Resourceful Nurses". RN, Dec. 1988, 22–25. NPL–444.

Davydov, et al., "Pathenogenic mechanism of the effect of vacuum therapy on the course of the wound process". Khirurgiia, Jun. 1990 (with English translation). DV13.

Davydov, et al., "Vacuum therapy in the treatment of suppurative lactation mastitis". Vestn. Khir., Nov. 1986 (with English translation). DV8.

Davydov, et al., "Bacteriological and cytological evaluation of the vacuum therapy of suppurative wounds". Vestn. Khir., Oct. 1988 (with English translation). DV2.

Davydov, et al., "Basis of the use of forced early secondary suture in the treatment of suppurative wounds by the vacuum therapy method". Vestn. Khir., Mar. 1990 (with English translation). DV1.

Borzov, et al., "Vacuum therapy of some skin diseases". Vestn. Dermatol. Venerol:, Aug. 1965 (with English translation). NPL–055.

M.J. Morykwas and L.C. Argenta, "Techniques in Use of V.A.C. Treatment (in English)", Acta Chir. Austriaca Supplement Nr. 150, 1998, p. 3–4 of 2–28. WFU–02.

Garcia–Rinaldi, et al., "Improving the Efficiency of Wound Drainage Catheters", J. Surg., 1975, pp. 372–373. NPL–169.

Raffl, et al. "The Five Year Survival Rate for Gastric Cancer: Statistical Study from Syracuse Medical Center", Cancer, 6:756–759, Jul. 1953. NPL–339.

Raffl, et al., The Use of Negative Pressure Under Skin Flaps After Radical Mastectomy, Ann. Surg. 136: 1048, Dec. 1952. NPL–340.

Marie Knight, "A Second Skin for Patients with Large Drainage Wounds," Nursing 6(1) p. 37, 1976. NPL–238.

Oscar Ramirez, "Optimal Wound Healing under Op–Site Dressing" Plas. & Recon. Surg., 73(3): 474–475; 1984. NPL–341.

Helen Bibleheiner, "Dealing with a Wound that Drains 1.5 Liters per Day," RN Aug. 1986, NPL–046.

Peter Schwab, "Primary Closure of the Perineal Wound After Proctectomy" Mayo Clin. Proc., Mar. 1974, vol. 49. NPL–362.

Interlocutory Decision in Opposition proceedings in favor of patentee (Wake Forest—Argenta, et al.) dated Feb. 17, 2003 EPOPWH2–06.

Letter Supplemental to Notice of Opposition to European Patent No. 0688189 dated Nov. 12, 2002. EPOPWH2–05.

Notice of Opposition to European Patent No. 0688189 dated Jun. 12, 2001. EPOPWH2–02.

Opposer's Appeal from Interlocutory Decision—dated Jun. 27, 2003. EPOPWH2–08.

Communication from EPO, Summons to Attend Oral Proceedings Pursuant to Rule 71(1) EPC, European Patent 0,620,720, 6 pages, Aug. 12, 2003. EPOPWH1–08.

Avery, C., et al., "Negative pressure wound dressing of the radial forearm donor site", International Journal of Oral Maxillofacial Surgery, 2000; 29, pp. 198–200. NPL–024.

Armstrong, David G., et al., "Outcomes of Subatmospheric Pressure Dressing Therapy on Wounds of the Diabetic Foot", Ostomy/Wound Management 2002; 48(4): 64–68. NPL–019.

Brown, Karen M., et al., "Vacuum–Assisted Closure in the Treatment of a 9–Year–Old Child with Severe and Multiple Dog Bite Injuries of the Thorax", Society of Thoracic Surgeons, 2001; 72:1409–1410. NPL–062.

Catarino, Pedro A., et al., "High–Pressure Suction Drainage via a Polyurethane Foam in the Management of Poststemotomy Mediastinitis", Ann Thorac Surg 2000; 70:1891–5. NPL–071.

Mendez–Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314–323. NPL–278, NPL–686.

Cooper, Susan Mary, "Topical negative pressure in the treatment of pressure ulcers", Letters posted in the Journal of the American Acad of Dermatology, Aug., Part 1, 1999, p. 280. NPL–099.

Davydov, I.A., et al., "Concept of clinico–biological control of the wound". Vestnik khirurgii imeni I.I. Grekova, v. 146, issue 2, 1991, 132–6 (with English translation). DV5.

de la Torre, Jorge I., MD, et al., "Healing a Wound with an Exposed Herrington Road: A Case Study", Ostomy Wound Management, pp. 18–19, May 2002, vol. 48, Issue 5. NPL–108.

de Lange, M.Y.,. et al., "Vacuum–assisted closure: indications and clinical experience", Eur J Plast Surg (2000) 23;178–182. NPL–109.

Deva, Anand, K., et al., "Topical negative pressure in wound management". MJA, Vo. 173, pp. 128–131, Aug. 7, 2000. NPL–113.

Elwood, Eric. T., et al., "Negative–Pressure Dressings in the Treatment of Hidradenitis Suppurativa", Ann Plast Surgery Jan. 2001; 46:49–51. NPL–136.

Evans, D. and Land, L., "Topical negative pressure for treating chronic wounds: a systematic review", British Journal of Plastic Surgery (2001), 54, 238–242. NPL–144.

Fabian, Thaddeus S., MD, "The Evaluation of Subatmospheric Pressure and Hyperbaric Oxygen is Ischemic Full–Thickness Wound Healing", The American Surgeon, Dec. 2000, vol. 66, 1136–1143. NPL–146.

Fenn, C.H. and Butler, P.E.M., "Abdominoplasty wound–healing complications: assisted closure using foam suction dressing", British Journal of Plastic Surgery (2001), 54, 348–351. NPL–150.

Giovannini, Uberto M., MD, "Negative Pressure for the Management of an Exposed Vascular Dacron Polyester Patch", Annals of Plastic Surgery, 47(5):577–578, 2001. NPL–171.

Gustafsson, Ronny, MD, "Vacuum–assisted closure therapy guided by C–reactive protein level in patients with deep sternal wound infection", The Journal of Thoracic and Cardiovascular Surgery, vol. 123, No. 5, pp. 895–900, May 2002. NPL–181.

Gwan–Nulla, Daniel N., MD and Casal, Rolando S., MD, "Toxic Shock Syndrome Associated with the Use of the Vacuum–Assisted Closure Device", Ann Plastic Surgery 2001;47:552–554. NPL–183.

Hersh, Robert E., MD, et al., "The Vacuum–Assisted Closure Device as a Bridge to Sternal Wound Closure", Ann Plast Surg. 2001; 46: 250–254. NPL–203.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167–171. NPL–205.

Joseph, Emmanuella, MD, et al., "A Prospective Randomized Trial of Vacuum–Assisted Closure Versus Standard Therapy of Chronic Nonhealing Wounds", Wounds 2000: 12(3): 60–67. NPL–228.

Josty, I.C., et al., "Vacuum–assisted closure: an alternative strategy in the management of degloving injuries of the foot", British Journal of Plastic Surgery (2001), 54, pp. 363–365. NPL–229.

Kostiuchenok, B.M., et al. "Vacuum Treatment in the Surgical Management of Suppurative Wounds", Izdatelstvo Meditsina, St. Petersburg, 1986, Sep.; 137(9): 18–21 (with English Translation). NPL–241.

Kovacs, Laszlo H., MD, "Necrotizing Fasciitis", Annals of Plastic Surgery, vol. 47, No. 6, Dec. 2001, pp. 680–682. NPL–242.

Kranser, Diane L., "Managing Wound Pain in Patients with Vacuum–Assisted Closure Devices", Ostomy Wound Management 2002; 48(5): 38–43. NPL–243.

Mendez–Eastman, Susan, RN, CPSN, CWCN, "wound therapy", Nursing2002, vol. 32, No. 5, May, pp. 59–63 and 1 sheet of quiz. NPL–280.

Mooney, James F., III., "Treatment of Soft Tissue Defects in Pediatric Patients Using the V.A.C. TM System", Clinical Orthopedics and Related Research, No. 376, pp. 26–31, Jul. 2000. WFU–26.

Scheufler, O., et al., "Problem–adapted application of vacuum occlusion dressings: case report and clinical experience", Eur. J. Plast Surg (2000) 23: 386–390. NPL–360.

Sposato, G., et al., "Ambulant vacuum–assisted closure of skin–graft dressing in the lower limbs using a portable mini–VAC device", British Journal of Plastic Surgery (2001), 54, 235–237. NPL–385.

Tang, Augustine T.M., et al., "Novel application of vacuum assisted closure technique to the treatment of sternotomy wound infection", European Journal of Cardio–Thoracic Surgery 17 (2000) 482–484. NPL–396.

Wu, S.H., et al., "Vacuum therapy as an intermediate phase in wound closure: a clinical experience", Eur J Surg (2000) 23;174–177. NPL–449.

Zhivotaev VM. Vacuum therapy of postoperative infected wounds of the urinary bladder, Klinicheskaia Khiurgiia. 1970;5:36–39. (in Russian) (and 1 sheet printout from PubMed). NPL–453.

The Kremlin Papers . . . perspectives in wound care, "A collection of published studies complementing the research and innovation of wound care", Russian Medical Journal "Vestnik Khirurgii", 5 Russian Articles from 1986–1991, translated by BlueSky Medical Group Inc. © 2004 NPL–244.

Interlocutory decision in Opposition proceedings in favor of patentee (Wake Forest—Argenta, et al.) dated May 19, 2004. EPOPWH1–13.

*Kinetic Concepts, Inc., et al.* vs. *Bluesky Medical Corporation, et al.*; Civil Action No. SA 03 CA 0832: Plaintiff's Original Complaint dated Aug. 28, 2003. BS–120.

*Kinetic Concepts, Inc., et al.* vs. *Bluesky Medical Corporation, et al.*; Civil Action No. SA 03 CA 0832: Plaintiffs' First Amended Complaint dated Sep. 8, 2003. BS–121.

*Kinetic Concepts, Inc., et al.* vs. *Bluesky Medical Corporation, et al.*; Civil Action No. SA 03 CA 0832: Defendant BlueSky Medical Corporation's Original Answer to Plaintiff's First Amended Complaint dated Sep. 30, 2003. BS–122.

*Kinetic Concepts, Inc., et al.* vs. *Bluesky Medical Corporation, et al.*; Civil Action No. SA 03 CA 0832: Answer, Additional Defenses, Counterclaims and Jury Demand of Medela, Inc. (Response due: Oct. 27, 2003—20 days after service) dated Oct. 6, 2003. BS–123.

*Kinetic Concepts, Inc., et al.* vs. *Bluesky Medical Corporation, et al.*; Civil Action No. SA 03 CA 0832; Plaintiff's Reply to Defendant BlueSky Medical Corporation's Counterclaim dated Oct. 23, 2003. BS–124.

*Kinetic Concepts, Inc., et al.* vs. *Bluesky Medical Corporation, et al.*; Civil Action No. SA 03 CA 0832; Summary of Appendix in Support of Medela AG's Motion to Dismiss for Lack of Personal Jurisdiction or, Alternatively, to Dismiss for Failure to State a Claim and for Partial Summary Judgment dated Oct. 24, 2003. BS–125.

*Kinetic Concepts, Inc., et al.* vs. *Bluesky Medical Corporation, et al.*; Civil Action No. SA 03 CA 0832: Original Answer of Defendant Patient Care Systems, Inc., dated Oct. 7, 2003. BS–126.

*Kinetic Concepts, Inc., et al.* vs. *Bluesky Medical Corporation, et al.*; Civil Action No. SA 03 CA 0832: Medela AG's Motion to Dismiss for Lack of Personal Jurisdiction or Alternatively, to Dismiss for Failure to State a Claim and For Partial Summary Judgment dated Oct. 24, 2003. BS–127.

*Kinetic Concepts, Inc., et al.* vs. *Bluesky Medical Corporation, et al.*; Civil Action No. SA 03 CA 0832: Plaintiff's Reply to Defendant Medela, Inc.'s Counterclaim dated Oct. 27, 2003. BS–128.

*Kinetic Concepts, Inc., et al.* vs. *Bluesky Medical Corporation, et al.*; Civil Action No. SA 03 CA 0832: Plaintiff's Response to Medela AG's Motion to Dismiss for Lack of Personal Jurisdiction, Motion to Dismiss for Failure to State a Claim, and Motion for Partial Summary Judgment, dated Nov. 10, 2003. BS–129.

3M™, Tegaderm Family of Transparent Dressings for Chronic Wounds, pp. 1–8 (2002). NPL–002.

Alper, Joseph C., et al., "The In Vitro Response of Fibroblasts to the Fluid that Accumulates Under a Vapor–Permeable Membrane". Journal of Investigative Dermatology, 84:513–515, 1985. NPL–013.

Alper, Joseph C., et al., "Use of the Vapor Permeable Membrane for Cutaneous Ulcers: Details of application and side effects", Journal of the American Academy of Dermatology, vol. 11, No. 5, Part I, Nov. 1984, pp. 858–866. (NPL–014).

Angermeier, Marla C., et al., "Vapor–Permeable Membrane Therapy for Ulcers of Osteomyelitis", J. Dermatol. Surg. Oncol,, 10:5, May 1984, pp. 384–388. NPL–016.

Bourke, et al., "Comparison Between Suction and Corrugated Drainage After Simple Mastectomy: A Report on Controlled Trial", Br. J. Surg., vol. 63, 1976, pp. 67–69. NPL–056.

ConstaVac™ Closed Wound Drainage System, Stryker Instruments, 2 pages. NPL–092.

Eaglstein, William H., "Experiences with Biosynthetic Dressings", Journal of the American Academy of Dermatology, vol. 12, No. 2, Part 2, Feb. 1985, pp. 434–440. NPL–129.

Falanga, Vincent, et al., "A Therapeutic Approach to Venous Ulcers", Journal of the American Academy of Dermatology, vol. 14, No. 5, Part I, May 1986, pp. 777–784. NPL–147.

Friedman, S., et al., "Treatment of Dermabrasion Wounds with a Hydrocolloid Occlusive Dressing", Arch Dermatol, vol. 121, Dec. 1985, pp. 1486–1487. NPL–166.

Friedman, Stephen J., et al., "Management of Leg Ulcers with Hydrocolloid Occlusive Dressing", Arch. Dermatol., vol. 120, Oct. 1984, pp. 1329–1336. NPL–167.

Holland, K.T., et al., "A Comparison of the In Vivo Antibacterial Effects of OpSite, Tegaderm and Ensure dressings", Journal of Hospital Infection, 1985, 6, pp. 299–303. NPL–209.

Jeter, Katherine F., et al., "Wound Dressings of the Nineties: Indications and Contraindications", Clinics in Podiatric Medicine and Surgery, vol. 8, No. 4, Oct. 1991, pp. 799–816. NPL–224.

Katz, Stuart, et al., "Semipermeable Occlusive Dressings", Arch Dermatol, vol. 122, Jan. 1986, pp. 58–62. NPL–231.

Lewis, R.T., "Knitted Polypropylene (Marlex) Mesh in the Repair of Incisional Hernias", The Canadian Journal of Surgery, vol. 27, No. 2, Mar. 1984, pp. 155–157. NPL–256.

Lower Extremity Ulcers, Chapter 9, pp. 47–57. NPL–259.

Microtek Medica, Inc. "The Microtek Complete Closed Wound Drainage System", 6 pages. NPL–285.

Rovee, David T., et al., "Effect of Local Wound Environment on Epidermal Healing", Dept. of Skin Biology, Johnson & Johnson Research, New Brunswick, NJ, pp. 159–181 (1972). NPL–348.

Satas, Donatas, "Handbook of Pressure–Sensitive Adhesive Technology", Silicone Release Coatings, Van Nostand Reinhold Company, 1982, pp. 384–403. NPL–355.

Turner, T.D., "A Look at Wound Dressings", Health and Social Service Journal, May 4, 1979, pp. 529–531. NPL–405.

Turner, T.D., "Recent Advances in Wound Management Products", pp. 3–6 NPL–406.

Turner, T.D., "Semipermeable Films as Wound Dressings", Welsh School of Pharmacy, University of Wales, Great Britain (Jul. 31, 1984). NPL–407.

Turner, T.D., "The Development of Wound Management Products", Chronic Wound Care, pp. 31–46. NPL–408.

Turner, T.D., et al., "Wound Management Product Selection", Journal of Sterile Services Managmenet, Apr. 1985, pp. 3–6. NPL–409.

Varghese, Mathew C., et al., "Local Environment of Chronic Wounds Under Synthetic Dressings", Arch. Dermatol, vol. 122, Jan. 1986, pp. 52–57. NPL–416.

Viljanto, J., "Cellstic: A Device for Wound Healing Studies in Man. Description of the Method", Journal of Surgical Research, 20, 1976, pp. 115–119. NPL–420.

Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236–239. NPL–425.

Wilson, John L., et al., "Loss of Blood Volume in Spinal Surgery with Use of Closed Wound Suction: An Experimental Study", Southern Medical Journal, Jul. 1968, pp. 761–763, read before the Section on Orthopaedic and Traumatic Surgery, Southern Medical Association, 61st Annual Meeting, Miami Beach, FL, (Nov. 13–16, 1967). NPL–437.

Winter, G.D., "Healing of Skin Wounds and the Influence of Dressings on the Repair Process", pp. 46–60 of "Surgical dressings and wound healing: proceedings of a symposium held on Jul. 7–8, 1970 at the University of Bradford", Crosby Lockwood for Bradford University Press, (1971). NPL–439.

Kohlman, P., et al., "Pouching Procedure To Collect Drainage From Around A Biliary Drainage Catheter", Ostomy/Wound Management, Nov./Dec. 1991, pp. 47–50, V. 37. NPL–240.

Alper, J., "Recent Advances in Moist Wound Healing", Southern Medical Journal, Nov. 1986, pp. 1398–1404, V. 79, N.11. NPL–011.

Reid, D., "Information on Cupping or Using Suction Cups on Wounds and for Healing Purposes", from Chines Herbal Medicine (2 pages). NPL–345.

Sheppard, M.D., "Sealed drainage of wounds," The Lancet, Jun. 14, 1952, pp. 1174–1176. NPL–410.

Putney, F., "The Use of Continuous Negative Pressure After Laryngectomy and Radial Neck Dissection", Surgery, Gynecology & Obstetrics, Aug. 1956, pp. 244–246. NPL–336.

Pleupump MK II, printouts from websites, www.xenamedical.se and www.landstinget.sormland.se, Aug. 14, 2001 (12 pages). NPL–332.

Brummelkamp, W., et al., "High–vacuum Drainage and Primary Perineal Wound Closure in Abdominoperineal Excision of the Rectum", The Netherland Journal of Surgery, 1991, pp. 236–239, V. 43, No. 6. NPL–063.

"Wound Suction; Better Drainage With Fewer Problems", Nursing 75, Oct., pp. 52–55 (1975). NPL–447.

Grams Aspirator, et al., Grams Medical, catalog pages (3 pages) (prices as of Aug. 1991 and Sep. 1992). NPL–175.

Medela Dominant promotional literature (2 pages of photos) (labeled circa 1984–1985). NPL–274.

Engdahl, O., et al., "Quantification of Aspirated Air Volume Reduces Treatment Time in Pneumothorax", Eur. Respir. J., 1990, 3, pp. 649–652. NPL–140.

Usage Manual Pleurasug TDR (2 pages of diagrams with descriptions). NPL–412.

Spengler, M., et al., "Performance of Filtered Sump Wound Drainage Tubes", Surgery, Gynecology & Obstetricsq, Mar. 1982, pp. 333–336, vol. 154. NPL–384.

Hallstrom, B., et al., "Postoperative Course After Total Hip Arthroplasty: Wound Drainage Versus No Drainage", Orthopaedic Review, Jul. 1992, pp. 847–851. NPL–185.

Miles, W., et al., "A Method of Performing Abdominoperineal Excision for Carcinoma of the Rectum and of the Terminal Portion of the Pelvic Colon", The Lancet, Dec. 19, 1908, pp. 1812–1813. NPL–287.

Benjamin, P., "Faeculent Peritonitis: A Complication of Vacuum Drainage", Br. J. Surg., 1980, pp. 453–454, vol. 67. NPL–042.

Sagi, A., et al., "Burn Hazard From Cupping—An Ancient Universal Medication Still in Practice", Burns, 1988, pp. 323–325, vol. 14, No. 4. NPL–351.

Agrama, H., et al., "Functional Longevity of Intraperitoneal Drains", The American Journal of Surgery, Sep. 1976, pp. 418–421, vol. 132. NPL–009.

Magee, C., et al., "Potentiation of Wound Infection by Surgical Drains", The American Journal of Surgery, May 1976, pp. 547–549, vol. 131. NPL–264.

Birdsell, D., et al., "The Theoretically Ideal Donor Site Dressing", Annals of Plastics Surgery, Jun. 1979, pp. 535–537, vol. 2, No. 6. NPL–048.

Cruse, P., et al., "A Five–Year Prospective Study of 23,649 Surgical Wounds", Surgical Wounds/Cruse and Foord, Aug. 1973, pp. 206–210, vol. 107. NPL–105.

Aubrey, D., et al., "Treatment of the Perineal Wound After Proctectomy by Intermittent Irrigation", Arch. Surg., Oct. 1984, pp. 1141–1144, vol. 119. NPL–021.

Mayo, C., "The One–Stage Combined Abdominoperineal Resection for Carcinoma of the Rectum, Rectosigmoid and Sigmoid", Surgical Clinics of North America, Aug. 1939, pp. 1011–1019. NPL–268.

Draper, J., "Make the dressing fit the wound", Nursing Times, Oct. 9, 1985, pp. 32–35. NPL–122.

Schumann, D., et al., "Preoperative Measures to Promote Wound Healing", Nursing Clinics of North America, Dec. 1979, pp. 683–699, vol. 14, No. 4. NPL–361.

Besst, J., et al., "Wound Healing—Intraoperative Factors", Nursing Clinics of North America, Dec. 1979, pp. 701–712, vol. 14, No. 4, NPL–044.

Cooper, D., et al., "Postsurgical Nursing Intervention as an Adjunct to Wound Healing", Nursing Clinics of North America, Dec. 1979, pp. 713–726, Nursing Clinics of North America, vol. 14, No. 4. NPL–097.

O'Bryne, C., "Clinical Detection and Management of Postoperative Wound Sepsis", Nursing Clinics of North America, Dec. 1979, pp. 727–741, vol. 14, No. 4. NPL–316.

Keith, C., "Would Management Following Head and Neck Surgery", Nursing Clinics of North America, Dec. 1979, pp. 761–778, vol. 14, No. 4. NPL–233.

Tenta, L., et al., "Suction Drainage of Wounds of the Head and Neck", Surgery, Gynecology & Obstetrics, Dec. 1989, p. 558, vol. 169. NPL–401.

Firlit, C., et al., "Surgical Wound Drainage: A Simple Device for Collection", journal of Urology, Aug. 1972, pp. 327, vol. 108. NPL–153.

Moloney, G., "Apposition and Drainage of Large Skin Flaps", Oxford, England, pp. 173–179 (Feb. 1957). NPL–296.

Worth, M., et al., "The Effectiveness of Bacterial Filtration in Vented Wound Drains", Journal of Surgical Research, 1979, pp. 405–407, 27. NPL–446.

Flynn, M., et al., "Promoting Wound Healing: Wound Healing Mechanisms", American Journal of Nursing, Oct. 1982, pp. 1544–1558. NPL–162.

Miles, W., "Technique of the Radical Operation for Cancer of the Rectum", The British Journal of Surgery, 1914–1915, pp. 292–305. NPL–286.

Hilton, P., "Surgical Wound Drainage: A Survey of Practices Among Gynaecologists in the British Isles", British Journal of Obstetrics and Gynaecology, Oct. 1988, pp. 1063–1069, vol. 95. NPL–207.

Milsom, I., et al., "An Evaluation of a Post–Operative Vacuum Drainage System", Current Medical Research and Opinion, 1979, pp. 160–164, vol. 6, No. 2. NPL–289.

Fox, J., et al., "The Use of Drains in Subcutaneous Surgical Procedures", The American Journal of Surgery, Nov. 1976, pp. 673–674, vol. 132. NPL–164.

Hilsabeck, J., "The Presacral Space as a Collector of Fluid Accumulations Following Rectal Anastomosis", American Society of Colon and Rectal Surgeons, (Oct. 1982), pp. 680–684, vol. 25, No. 7. NPL–206.

Hulten, L., et al., "Primary Closure of Perineal Wound After Protocolectomy or Rectal Excision", Acta Chir Scand 137, 1971, pp. 467–469. NPL–215.

Landes, R., "An Improved Suction Device for Draining Wounds", Arch. Surg., May 1972, pp. 707, vol. 104. NPL–248.

Hugh, T., "Abdominal Wound Drainage", The Medical Journal of Australia, May 4, 1987, pp. 505. NPL–214.

Eisenbud, D., "Modern Wound Management", Adadem Publishing, pp. 109–116 (Jan. 1999). NPL–134.

Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley–Liss, Inc., pp. 257–265. NPL–128.

Bruno, P., "The Nature of Wound Healing", Nursing Clinics of North America, Dec. 1979, pp. 667–682, vol. 14, No. 4. NPL–064.

Bar–El, Y., et al., "Potentially Dangerous Negative Intrapleural Pressures Generated by Ordinary Pleural Drainage Systems", Chest, Feb. 2001, pp. 511–514, vol. 119, No. 2. NPL–036.

Agarwala, S., et al., "Use of Mini–Vacuum Drains in Small Surgical Wounds", Plastic and Reconstructive Surgery, Apr. 1998, pp. 1421–1422, vol. 101, n. 5. NPL–008.

Nasser, A., "The Use of the Mini–Flap Wound Suction Drain in a Maxillofacial Surgery", Annals of the Royal College of Surgeons of England, 1986, pp. 151–153, vol. 68. NPL–309.

Hunt, T.K., et al. eds., "Dead Space" and "Drainage", Fundamentals of Wound Management, pp. 416–447 (1979). NPL–186.

Lumley, J., et al., "The Physical and bacteriological Properties of Disposable and Non–Disposable Suction Drainage Units in the Laboratory", Br. J. Surg, 1974, pp. 832–837, vol. 61. NPL–261.

Britton, B., et al., "A Comparison Between Disposable and Non–disposable Suction Drainage Units: A Report of a Controlled Trial", Br. J. Surg., 1979, pp. 279–280, vol. 66. NPL–057.

McFarlane, R., "The use of Continuous Suction Under Skin Flaps", British Journal of Plastic Surgery, pp. 77–86 (1958–1959). NPL–271.

Fay, M., "Drainage Systems: Their Role in Wound Healing", AORN Journal, Sep. 1987, pp. 442–455, vol. 46, No. 3. NPL–149.

Taylor, V., "Meeting the Challenge of Fistulas & Draining Wounds", Nursing80, Jun., pp. 45–51. NPL–398.

Orgill, D., "Curent Concepts and Approaches to Would Healing", Critical Care Medicine, Sep. 1988, pp. 899–908, vol. 16, No. 9. NPL–320.

Part III. Resolving Selected Clinical Dilemmas, pp. 17–20. NPL–328.

"Making Sense of Wound Drainage", Nursing Times, Jul. 5, 1989, pp. 40–42, vol. 85, No. 27. NPL–265.

Manualectric Breastpump, Catalog pages (4 pages), diagrams and descriptions. NPL–266.

Harkiss, K., "Leg Ulcers Cheaper in the Long Run", Community Outlook, Aug. 1985, pp. 19, 21, 22, 24 & 26 NPL–190, NPL–601.

Westaby, S. (Editor), "Wound Care No. 43; Which Dressing and Why", Nursing Times, Jul. 21, 1982, pp. 41–44. NPL–434.

OpSite Wound Dressings, "Do Your Pressure Sore Dressings Shape Up to the OpSite Standard", 2 pages of advertisements. NPL–319.

Dow Corning Silastic® Foam Dressing: A New Concept in the Management of Open Granulating Wounds, 2 pages of advertisements. NPL–121.

Cobb, J., "Why Use Drains", The Journal of Bone and Joint Surgery, Nov. 1990, pp. 993–995, vol. 72–B, No. 6. NPL–088.

Garcia–Rinaldi, R., "Improving the Efficiency of Wound Drainage Catheters", the Journal of Surgery, Sep. 1975, pp. 372–373, vol. 130. NPL–169.

$Pleur_x$ Plerual Catheter, Denver Biomedical, 4 pages of brochure. NPL–334.

Silvis, R., et al., "The Use of Continuous Suction Negative Pressure Instead of Pressure Dressing", Annals of Surgery, Aug. 1955, pp. 252–256, vol. 142, No. 2. NPL–374.

Van Way, C., "Prevention of Suction–Induced Gastric Mucosal Damage in Dogs", Gastric Suction, 1987, pp. 774–777, vol. 15, No. 8. NPL–415.

Moserova, J., "The Healing and Treatment of Skin Defects", pp. 103–151 (1989) NPL–299.

Rabkin, J., et al., "Infection and Oxygen, Problem Wounds: The Role of Oxygen", pp. 1–15 (1987). NPL–338.

Paradise Valley Hospital, The Center for Wound Healing and Hyperbaric Medicine, 3 pages of brochure. NPL–326.

DuoDerm Hydroactive™ Dressing, "In wound management—Now, a proven environment for fast healing",1 page advertisement. NPL–126.

Howmedica porto–vac®, "Gentle, Steady Wound Drainage", 1 page advertisement. NPL–212.

Silicone from CUI (Cox–Uphoff International), "Flexability", 1 page advertisement. NPL–371.

Curtin, L., "Wound Management: Care and Cost—An Overview", Nursing Management, Feb. 1984, pp. 22–25, vol. 15. NPL–106.

Grabowski, S., "Leczenie ran z zastosowaniem podcisnienia", article, pp. 19–21, English abstract on p. 21 and 1 sheet printout from PubMed, (Jan. 1, 1964). NPL–174.

Royle, G., et al., "Disposable Drains", Annals of the Royal College of Surgery of England, 1984, 1 page, vol. 66. NPL–349.

Meehan, P., "Open Abdominal Wounds: A Creative Approach to a Challenging Problem", Pregressions, 1992, pp. 3–8, 11, vol. 4, No. 2. NPL–276.

Stansby, G., et al., "Vacuum Drainage of Groin Wounds After Vascular Surgery", Br. J. Surg., Oct. 1990, pp. 1194–1195, vol. 77, No. 10. NPL–391.

Edlich, R., et al., "Evaluation of a New, Improved Surgical Drainage System", The American Journal of Surgery, Feb. 1985, pp. 295–298, vol. 149. NPL–130.

Broader, J., et al., "Management of the Pelvic Space After Proctectomy", Br. J. Surg., 1974, pp. 94–97, vol. 61. NPL–058.

Ayoub, M., et al., "A study of cutaneous and intracompartmental limb pressures associated with the combined use of tourniquets and plaster casts", May 1986, pp. 497, vol. 68–B, No. 3. NPL–025.

Cooper, D., "Optimizing Wound Healing: A Practice Within Nursing's Domain", Nursing Clinics of North America, Mar. 1990, pp. 165–180, vol. 25, No. 1. NPL–095.

Cooper, D., "Wound Healing", Nursing Clinics of North America, pp. 163–164 (Mar. 1990). NPL–096.

Hollis, H., et al., "A Practical Approach to Wound Care in Patients With Complex Enterocutaneous Fistulas", Surgery, Gynecology & Obstetrics, Aug. 1985, pp. 178–180, vol. 161. NPL–210.

Fingerhut, A., "Passive vs. Closed Suction Drainage After Perineal Would Closure Following Abdominoperineal Rectal Excision for Carcinoma", Dis Colon Rectum, Sep. 1995, pp. 926–932, vol. 38, No. 9. NPL–152.

Cook Pneumothorax Catheter Set, Wayne Pneumothorax Catheter Set, Emergency Medicine, Videotape advertisement. NPL–094.

Schaffer, D., "Closed Suction", Nursing97, Nov., http://www.springnet.com, pp. 62–64. NPL–357.

Carroll, P., "The Principles of Vacuum and Its Use in the Hospital Environment", Ohmeda, pp. 1–30 and cover sheet. NPL–070.

Morykwas, M.J., et al., "Use of Negative Pressure to Increase the Rate of Granulation Tissue Formation in Chronic Open Wounds", The FASEB Journal, (799–800), Feb. 19, 19963. WFU–13.

Orringer, J.S., et al., "Management of Wounds in Patients with Complex Enterocutaneous Fistulas", Surgery, Gynecology & Obstetrics, Jul. 1987, vol. 165. NPL–323.

*Kinetic Concepts, Inc., et al., v. Bluesky Medical Corporation, et al.,* Civil Action No. SA–03–CA–0832–RF, U.S. Dist. Count, W. Dist. of TX San Antonio Div., Report of Katherine F. Jeter, Nov. 28, 2004. BS–11.

Swearingen, P.L., "The Addition–Wesley Photo–Atlas of Nursing Procedures", 9 pages, © 1984. NPL–393.

Mulder, G.D., et al., Clinicians' Pocket Guide to Chronic Wound Repair, Wound Healing Publications Second Edition, 1992, pp. 1–107. NPL–300.

Opposition to EP 0,620,720, Appeal of Opponent Paul Hartmann AG, dated Sep. 20, 2004 (with English translation). EPOPWH1–15.

Opposition EP to 0,620,720, Patentee's Grounds of Appeal dated Sep. 29, 2004, 31 pages. EPOPWH1–18.

Peacock, E.E., Jr., Wound Repair:, Repair of Skin Wounds, 1984, pp. 172–175. NPL–329.

Murray, J., et al., "On the Local and General Influence on the Body if Increased and Diminished Atmospheric Pressure", The Lancet, V. 1, 1834–1835; pp. 909–917. NPL–303.

Herrmann, L., et al., "The Conservative Treatment of Arteriosclerotic Peripheral Vascular Diseases", pp. 750–760 (Oct. 1934). NPL–199.

Versatile 1 Wound Vacuum System™ for The Promotion of Wound Healing, Wound Application instructions, 1 page advertisement. NPL–418.

Bluesky Medical "The Versatile One!™", Wound Drainage and More, 1 page advertisement. (Labeled Spring 2003). NPL–050.

Chariker–Jeter® Wound Sealing Kit, Would Application Instructions, 1 page advertisement. NPL–078.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Brief on Claim Construction dated Mar. 7, 2005. BS–151.

*Kinetic Concepts, Inc., et al., v. Bluesky Medical Corporation, et al.,* Civil Action No. SA–03–CA–0832–RF, U.S. District Court, W. Dist. of Texas San Antonio Div., Medela AG and Medela, Inc's Opening Memorandum Regarding Construction of the Patent Claims dated Mar. 7, 2005. BS–152.

*Kinetic Concepts, Inc., et al., v. Bluesky Medical Corporation, et al.,* Civil Action No. SA–03–CA–0832–RF, U.S. District Court, W. Dist. of Texas San Antonio Div., BlueSky Medical Group Incorporated Opening Markman Brief Regarding U.S. Patent Nos. 4,969,880 and 5,636,643. BS–153.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Responsive Claim Construction Brief dated Mar. 28, 2005. BS–148.

*Kinetic Concepts, Inc., et al., v. Bluesky Medical Corporation, et al.,* Civil Action No. SA–03–CA–0832–RF, U.S. District Court, W. Dist. of Texas San Antonio Div., Declaration of Michael J. Morykwas in Support on Plaintiffs' Responsive Claim Construction Brief dated Mar. 24, 2005. BS–149.

*Kinetic Concepts, Inc., et al., v. Bluesky Medical Corporation, et al.,* Civil Action No. SA–03–CA–0832–RF, U.S. District Court, W. Dist. of Texas San Antonio Div., Declaration of Wilson C. Hayes in Support on Plaintiffs' Responsive Claim Construction Brief dated Mar. 25, 2005. BS–150.

Johnson, Frank E., "An Improved Technique for Skin Graft Placement Using A Suction Drain", pp. 585–586 (Dec. 1984). NPL–226.

Dewan, P.A., et al., "An Alternative Approach To Skin Graft Donor Site Dressing", Aust. N.Z. J. Surg. 1986, 56, 509–510. NPL–116.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Reply Brief on Claim Construction dated Apr. 18, 2005. BS–147.

*Kinetic Concepts, Inc., et al., v. Bluesky Medical Corporation, et al.,* Civil Action No. SA–03–CA–0832–RF, U.S. District Court; W. Dist. of Texas San Antonio Div., Medela AG and Medela, Inc.'s Response on Claim Construction dated Mar. 28, 2005. BS–154.

*Kinetic Concepts, Inc., et al., v. Bluesky Medical Corporation, et al.,* Civil Action No. SA–03–CA–0832–RF, U.S. District Court, W. Dist. of Texas San Antonio Div., Bluesky Medical Group Incorporated's Opposition Markman Brief Regarding U.S. Patent Nos. 4,969,880 and 5,636,643. BS–155.

Opposition EP to 0,620,720, Third Party Observations dated Feb. 15, 2005. EPOPWH1–19.

*Kinetic Concepts, Inc., et al., v. Bluesky Medical Corporation, e al.,* Civil Action No. SA–03–CA–0832–RF, U.S. District Court, W. Dist. of Texas San Antonio Div., Plaintiffs' Markman Presentation of May 12, 2005. BS–156.

*Kinetic Concepts, Inc., et al., v. Bluesky Medical Corporation, et al.,* Civil Action No. SA–03–CA–0832–RF, U.S. District Court, W. Dist. of Texas San Antonio Div., Blue Sky Medical Corp.'s Markman Presentation dated May 12, 2005. BS–157.

*Kinetic Concepts, Inc., et al., v. Bluesky Medical Corporation, et al.,* Civil Action No. SA–03–CA–0832–RF, U.S. District Court, W. Dist. of Texas San Antonio Div., Medela's Markman Presentation dated May 12, 2005. BS–158.

Opposition EP to 0,620,720, Response to Opponent Paul Hartmann AG dated Apr. 25, 2005 (with English translation). EPOPWH1–17.

Davies, J.W.L., "Synthetic materials for covering burn wounds: Progress towards perfection. Part I. Short term dressing materials", Burns, 1983, Nov.; 10(2), 94–103. NPL–107.

Lamke, L.O., et al., "The evaporative water loss from burns and the water–vapour permeability of grafts and artificial membranes used in the treatment of burns", Burns, 3, 159–165, 1977. NPL–247.

Barnett, A., et al., "Comparison of Synthetic Adhesive Moisture Vapor Permeable and Fine Mesh Gauze Dressings for Split–Thickness Skin Graft Donor Sites", The American Journal of Surgery, vol. 145, Mar. 1983, pp. 379–381. NPL–038.

Alper, J., et al., "Moist wound healing under a vapor permeable membrane", Journal of the American Academy of Dermatology, vol. 8, No. 3, Mar. 1983, pp. 347–353. NPL–012.

James, J.H., et al., "The use of Opsite, A Vapour Permeable Dressing, on Skin Donor Sites", British Journal of Plastic Surgery (1975), 28, 107–110. NPL–222.

Nahas, L.F., et al., "Use of Semipermable Polyurethane Membrane for Skin Graft Dressings", Plastic and Reconstructive Surgery, Jun. 1981, pp. 791–792. NPL–306.

Edlich, R.F., et al., "Surgical Devices in Wound Healing Management", Wound Healing Biochemical & Clinical Aspects, W.B. Saunders Company, © 1992, pp. 581–599. NPL–131.

Orr, RK, et al., "Early Discharge After Mastectomy. A Safe Way of Diminishing Hospital Cost", Am.Surg. Mar. 1987; 53(3) Abstract. NPL–322.

Otolaryngology, Head and Neck Surgery, The C.V. Mosby Company, © 1986, pp. 1716, 1724 and 2521. NPL–324.

Otolaryngology, vol. III, Head and Neck, W.B. Saunders Company, © 1980, pp. 2963. NPL–325.

Lore, Jr., J.M., "An Atlas of Head and Neck Surgery", Second Edition, vol. II, W.B. Saunders Company, © 1973. NPL–258.

*Kinetic Concepts, Inc., et al., v. Bluesky Medical Corporation, et al.,* Civil Action No. SA–03–CA–0832–RF, U.S. District Court, W. Dist. of Texas San Antonio Div., Letter Brief from BlueSky Medical dated May 31, 2005. BS–159.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiff's First Letter Brief from Markman hearing dated May 26, 2005. BS–160.

*Kinetic Concepts, Inc., et al., v. Bluesky Medical Corporation, et al.,* Civil Action No. SA–03–CA–0832–RF, U.S. District Court, W. Dist. of Texas San Antonio Div., Plantiff's Second Letter Brief from Markman hearing dated May 31, 2005. BS–161.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Louis C. Argenta, M.D., Apr. 29, 2005. BS–68.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Michael Allan Batalia, PhD. Jan. 12, 2005. BS–69.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Michael John Morykwas, PhD. Jan. 13, 2005. BS–70.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendents Medela AG and Medela, Inc.'s Motion for Leave to Amend Designation of Expert Witnesses dated May 18, 2005. BS–162.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Annswer to Defendant Bluesky Medical Group Incorporated's Crossclaim dated Jun. 1, 2005. BS–163.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiff's Answer to Defendant Richard Weston's Counterclaim dated Jun. 1, 2005. BS–164.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Medela Inc.'s Amended Counterclaim dated Jun. 1, 2005. BS–165.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Medela AG's Amended Counterclaims dated Jun. 1, 2005. BS–166.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Objections and Answers to Medela's Supoena in a Civil Case for Production of Documents and Deposition on Written Questions to Wake Forest University Baptist Medical Center dated Jun. 1, 2005. BS–167.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela, Inc. and Medela AG's Reply in Support of Motion for Leave to File Amended Answers to Third Amended Complaint, Additional Defenses, Second Amended Counterclaims and Jury Demands dated Jun. 1, 2005. BS–168.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Opposition to Medela AG and Medela, Inc.'s Motion for Leave to Amend Designation of Expert Witnesses and Request for Hearing dated Jun. 1, 2005. BS–169.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Objections and Answers to Medela, Inc.'s Supoena in a Civil Case and Deposition on Written Questions to Dr. Joseph Molnar and Dr. Lawrence Webb dated Feb. 24, 2005. BS–170.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Shelly Taylor dated Nov. 23, 2004. BS–71.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Michael Miller, D.O. dated Mar. 8, 2005. BS–72.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela AG's First Supplemental Response to Plaintiffs' First Interrogatories To Defendant Medela AG dated Jul. 13, 2005. BS–179.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela Inc.'s First Supplemental Response to Plaintiffs' First Interrogatories To Defendant Medela, Inc. dated Aug. 16, 2005. BS–180.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Matthew C. Dainman, Feb. 3, 2005. BS–73.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Ronald C. Hamaker, May 26, 2005. BS–74.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Mordechai Twena, Jan. 25, 2005. BS–75.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Preliminary Proposed Constructions of Newly Asserted Claims From the '643 and '081 Patents dated Sep. 12, 2005. BS–181.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Opposition to Defendant Bluesky Medical Group Incorporated's and Richard Weston's Motion for Summary Judgment on the '643 Patent, including Declaration of Wilson C. Hayes in Support Thereof including Exhibits. BS–182.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Opposition to Defendant Bluesky Medical Group Incorporated's and Richard Weston's Motion for Summary Judgment on the '880 Patent, including Declaration of Wilson C. Hayes in Support Thereof including Exhibits. BS–183.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Answer To Fourth Amended Complaint, Additional Defenses, Third Amended Counterclaims and Jury Demand of Defendant Medela AG, Jul. 18, 2005. BS–184.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Answer To Fourth Amended Complaint, Additional Defenses, Third Amended Counterclaims and Jury Demand of Defendant Medela, Inc., Jul. 18, 2005. BS–185.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Valery Gilevich (Dec. 14, 2004). BS–49.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela, Inc., and Medela AG's Motion for Entry of Amended Protective Order with Exhibits dated Oct. 7, 2005. BS–186.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Videotaped Deposition transcript of Carr Lane Quackenbush dated Oct. 6, 2004. BS–79.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela AG's Answer to Plaintiffs' Second Interrogation dated Oct. 7, 2005. BS–187.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela AG's Affidavit of Mitchell D. Lukin Pursuant to Local Rule CV–33(a) dated Oct. 7, 2005. BS–188.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela AG's Response to Plaintiffs' Second Request for Production of Documents dated Oct. 7, 2005. BS–189.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Medela AG's Response to Plaintiffs' Third Request for Production of Documents dated Oct. 7, 2005. BS–190.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Medela, Inc.'s Response to Plaintiffs' Second Request for Production of Documents dated Oct. 7, 2005. BS–191.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Opening Brief on Claim Construction of Disputed Claim Terms From the '643 and '081 Patents with Exhibits dated Oct. 6, 2005. BS–192.

*Kinetic Concepts, Inc., et al., v. Bluesky Medical Corporation, et al.,* Civil Action No. SA–03–CA–0832–RF, U.S. District Court, W. Dist. of Texas San Antonio Div., Medela, Inc.'s Second Set of Interrogatories To Wake Forest University Health Sciences dated Oct. 7, 2005. BS–193.

*Kinetic Concepts, Inc., et al., v. Bluesky Medical Corporation, et al.,* Civil Action No. SA–03–CA–0832–RF, U.S. District Court, W. Dist. of Texas San Antonio Div., Medela, Inc.'s Eighth Set of Requests For Production To Plaintiffs Kinetic Concepts, Inc., KCI Licensing, Inc., KCI, USA, Inc., and Wake Forest University Health Sciences dated Oct. 7, 2005. BS–194.

*Kinetic Concepts, Inc., et al., v. Bluesky Medical Corporation, et al.,* Civil Aciton No. SA–03–CA–0832–RF, U.S. District Court, W. Dist. of Texas San Antonio Div., Order Grating Joint Motion to Extend Deadlines dated Sep. 30, 2005. BS–195.

*Kinetic Concepts, Inc., et al., v. Bluesky Medical Corporation, et al.,* Civil Action No. SA–03–CA–0832–RF, U.S. District Court, W. Dist. of Texas San Antonio Div., BlueSky Medical Group Inc.'s Additional Supplemental Discovery Production with Bates Labels and Cover Letter dated Sep. 30, 2005. BS–224.

*Kinetic Concepts, Inc., et al., v. Bluesky Medical Corporation, et al.,* Civil Action No. SA–03–CA–0832–RF, U.S. District Court, W. Dist. of Texas San Antonio Div., Joint Motion for Entry of Order Adopting the Parties' Stipulated Claim Term Constructions dated Oct. 6, 2005. BS–196.

*Kinetic Concepts, Inc., et al., v. Bluesky Medical Corporation, et al.,* Civil Action No. SA–03–CA–0832–RF, U.S. District Court, W. Dist. of Texas San Antonio Div., Order Adopting the Parties' Stipulated Claim Term Constructions. BS–197.

*Kinetic Concepts, Inc., et al., v. Bluesky Medical Corporation, et al.,* Civil Action No. SA–03–CA–0832–RF, U.S. District Court, W. Dist. of Texas San Antonio Div., Promotional Slide Presentation BlueSky Medical Negative Pressure Wound Care with Versatile 1 Presentation Presented by Penny Campbell and Shelly Burdette–Taylor 27 pages (dated Oct. 14, 2005). NPL–067.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky Medical Group Inc. and Richard Weston's Reply to Plaintiff's Opposition to Defendant Bluesky Medical Group Inc. and Richard Weston's Motions for Partial Summary Judgment dated Sep. 28, 2005. BS–198.

*Kinetic Concepts, Inc., et al.., v. Bluesky Medical Corporation, et al.,* Civil Action No. SA–03–CA–0832–RF, U.S. District Court, W. Dist. of Texas San Antonio Div., Order Granting Plaintiffs' Unopposed Motion to Supplement The Record for its response to Bluesky's Motion for Partial Summary Judgment dated Oct. 13, 2005. BS–200.

*Kinetic Concepts, Inc., et al., v. Bluesky Medical Corporation, et al.,* Civil Action No. SA–03–CA–0832–RF, U.S. District Court, W. Dist. of Texas San Antonio Div., Order Granting Medela, Inc., And medela AG's Unopposed Motion to Extend Deadlines for Markman Briefing dated Oct. 13, 2005. BS–201.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Unopposed Motion to Supplement the Record in Support of Their Response to Bluesky's Motion For Partial Summary Judgment on Counts Twelve, Thirteen, and Fifteen dated Oct. 10, 2005. BS–202.

Barillo, D., et al., "Management of Burns to the Hand", Wounds 15,(1):4–9, 2003 Health Management Publications, Inc., Posted Feb. 13, 2003. NPL–037.

Medical Technology & Innovation, "Medical Technology is Extending Life, Reducing Costs", vol. 1, Issue 46, Dec. 4, 200. NPL–275.

Wu, Lisa C., et al., "Vacuum–Assisted Closure for the Treatment of Sternal Wounds: The Bridge Between Debridement and Definitive Closure", printout from www.plasticsurgery.org., 3 pages (printout dated Apr. 20, 2005). NPL–448.

*Kinetic Concepts, Inc., et al., v. Bluesky Medical Corporation, et al.,* Civil Action No. SA–03–CA–0832–RF, U.S. District Court, W. Dist. of Texas San Antonio Div., Joint Claim Construction and Prehearing Statement dated Sep. 16, 2005. BS–204.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendants' Opening Brief Regarding Claim Construction for The '081 Patent and Certain Claims of the '643 Patent dated Oct. 5, 2005. BS–203.

Bertone, A., "Management of Exuberant Granulation Tissue", Wound Management, pp. 551–562 (Dec. 1989), NPL–043.

Taber's Cyclopedia Medical Dictionary, Edition 18, pp. 937, 942 and 1375. NPL–394.

Harris, Ann, et al., "Hypergranulation Tissues: a Nontraumatic Method of Management", Ostomy/Would Management, vol. 40, No. 5, Jun. 1994. NPL–193.

Opposition EP to 0620720, Patentee Response to Grounds of Appeal Filed by Opponent, Paul Hartmann AG, with Exhibits dated Apr. 25, 2005. EPOPWH1–16.

Opposition EP to 0620720, Opponents Response to Grounds of Appeal Filed by Patentee (with translation), dated Apr. 25, 2005. EPOPWH1–17.

Opposition EP to 0620720, Patentees' Grounds of Appeal, dated Sep. 29, 2004. EPOPWH1–18.

Opposition EP to 0620720, Third–Party Communication dated Feb. 15, 2005 (R.G.C. Jenkins & Co.) EPOPW1–19.

Opposition EP to 0620720, Interlocutory Decision dated May 19, 2004. EPOPWH1–13.

Opposition EP to 0620720, Communication of Patentee dated Nov. 25, 2003. EPOPWH1–12.

Opposition EP to 0620720, Third–Party Communication dated Nov. 12, 2003 (R.G.C. Jenkins & Co.) EPOPWH1–11.

Opposition EP to 0620720, Third–Party Communication dated Aug. 14, 2003. (R.G.C. Jenkins & Co.) EPOPWH1–09.

Opposition EP to 0620720, Communication of Patentee dated Nov. 9, 2001. EPOPWH1–10.

Webster's New Universal Unabridged Dictionary Deluxe Second Edition, p. 631. NPL–431.

Opposition EP to 0620720, Communication of Opponent Mondomed dated Aug. 8, 2001. (Margot Muller–Gerbes) EPOPWH1–07.

Opposition EP to 0620720, Communication of Opponent Mondomed dated May 3, 2001. (Margot Muller–Gerbes). EPOPWH1–06.

Opposition EP to 0620720, Communication of Patentee dated Sep. 22, 200. EPOPWH1–05.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky Medical Group Incorporated's and Richard Weston's Motion for Summary Judgment on the '643 Patent with Exhibits dated Aug. 120, 2005. BS–205.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky Medical Group Incorporated's and Richard Weston's Motion for Summary Judgment on the '880 Patent with Exhibits dated Aug. 10, 2005. BS–206.

Bier, A., et al., Bier's Hyperemic Treatment, "Hyperemia by suction apparatus", Hyperemia as a Therapeutic Agent, Chicago, IL, Roberts Publishing; 1905: 74–85. NPL–216.

*Kinetic Concepts, Inc., et al., v. Bluesky Medical Corporation, et al.,* Civil Action SA–03–CA–0832–RF, U.S. District Court, W. Dist. of Texas San Antonio Div., Plaintiffs' Sureply Further Opposing Defendant and '880 Patents with Exhibits dated Oct. 14, 2005. BS–133.

Chariker–Jeter Technique Tutorial by Penny E. Campbell, Wound Care Solution, 1 page tutorial chart. NPL–075.

Bluesky Medical, Negative Pressure Wound Therapy, Product Catalog Fall 2005, "Finally a choice . . . " 8 pages. NPL–053.

Chariker–Jeter Status Link from the website www.trademark.com/cbi–bin/tmlist. Oct. 14, 2005, 1 page.

Bluesky Medical Support, printout of webpages www.woundvacuum.com/Standard%20Pages/support.htm, Oct. 11, 2005, pp. 1–3. NPL–051.

Healing of Full Thickness Defects in Swine NPL–197.

Opposition of EP to 0,620,720, Summons to Oral Proceedings Appeal dated Dec. 21, 2005. EPOPWH1–20.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs Letter to Honorable Royal Furgeson dated Jan. 3, 2006. BS–130.

*Kinetic Concepts, Inc., et al., v. Bluesky Medical Corporation, et al.,*, Civil Action No. SA–03–CA–0832–RF, U.S. District Court, W. Dist. of Texas San Antonio Div., Defendants Letter to Honorable Royal Furgeson dated Jan. 3, 2006. BS–131.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Reply Claim Construction Brief with Exhibits dated Nov. 11, 2005. BS–132.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Surreply Further Opposing Defendant Bluesky Medical Group Incorporated's and Richard Weston's Motions for Summary Judgment on the '643 and '880 Patents with Exhibits dated Oct. 14, 2005. BS–133.

*Kinetic Concepts, Inc., et al., v. Bluesky Medical Corporation, et al.,* Civil Action No. SA–03–CA–0832–RF, U.S. District Court, W. Dist. of Texas San Antonio Div. Plaintiffs' Opposition to Defendant Bluesky Medical Group Incorporated's and Richard Weston's Motion for Summary Judgment on the '880 Patent with Exhibits dated Sep. 12, 2005. BS–134.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky and Richard Weston's First Amended Cross-claims and Answer to Plaintiffs' Fourth Amended Complaint, Counterclaims, and Joinder of Wake Forest University dated Nov. 15, 2005. BS–135.

Webster, J.G., "Prevention of Pressure Sores", © IOP Publishing Ltd 1991, The Adam Hilger Series on Biomedical Engineering, pp. 199–223. NPL–430.

Garcia–Velasco, M., et al., "Compression Treatment of Hypertrophic Scars in Burned Children", The Canadian Journal of Surgery, V.21, No. 5, Sep. 1978, pp. 450–452. NPL–170.

Rose, M.P., et al., "The Clinical Use Of A Tubular Compression Bandage, Tubigrip, for Burn–Scar Therapy: A Critical Anaylis", Burns (1985) 12, 58–64. NPL–347.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky and Richard Weston's Objections and Responses to Plaintiffs' Fifth Request for Production dated Dec. 9, 2005. BS–136.

*Kinetic Concepts, Inc., et al., v. Bluesky Medical Corporation, et al.,* Civil Action No. SA–03–CA–0823–RF, U.S. District Court, W. Dist. of Texas San Antonio Div., Defendants' Response Brief Regarding Second Claim Construction Hearing ('081 Patent and Certain Claims of the '643 patent), with Exhibits dated Oct. 25, 2005. BS–137.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Medela, Inc.'s Objections and Responses to Plaintiffs' Sixth Request for Production of Documents dated Dec. 9, 2005. BS–138.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendant Bluesky and Richard Weston's First Amended Cross-claim and Answer to Plaintiffs' Fourth Amended Complaint, Counterclaims, and Joinder of Wake Forest University dated Nov. 15, 2005. BS–139.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Responsive Claim Construction Brief on the Disputed Claim Terms from the '6443 and '081 Patents with Exhibits dated Oct. 25, 2005. BS–140.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Markman Hearing Medela Presentation, pp. 1–78. BS–245.

Opposition EP to 0,618,189 New European Patent Specification EP 0688189B2. EPOPWH2–01.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Supplemental Expert Report of Wilson C. Hayes, Ph.D. Concerning Infringement of Newly Asserted Claims of U.S. Patent Nos. 5,636,643 and 5,645,081 dated Dec. 19, 2005. BS–55.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Dennis P. Orgill, M.D., Ph.D. with Exhibits dated Dec. 29, 2005. BS–1.

Opposition EP to 0,618,189 Decision to Maintain the European Patent in Amended Form (Article 102(3) EPC) dated Apr. 22, 2005, 1 page. EPOPWH2–10.

Opposition EP to 0,618,189 Letter relating to Appeal Procedure dated Mar. 5, 2004, 10 pages. EPOPWH2–09.

Opposition EP to 0,618,189 Letter relating to Appeal Procedure dated Jun. 7, 2003. EPOPWH2–08.

Opposition EP to 0,618,189 Interlocutory Decision in Opposition Proceedings with Grounds for the Decision dated Feb. 17, 2003. EPOPWH2–06.

Opposition EP to 0,618,189 Minutes of the Oral Proceedings, Documents for the Maintenance of the Patent as Amended, Annex to the Commuication dated Feb. 17, 2003. EPOPWH2–07.

Opposition EP to 0,618,189 Letter Pursuant to Rule 71a EPC and all Other Letter during Oral Proceedings dated Nov. 11, 2002. EPOPWH2–04.

Opposition EP to 0,618,189 Reply of the Patent Proprietor to the Notice(s) of Opposiiton dated Mar. 15, 2002. EPOPWH2–03.

Opposition EP to 0,618,189 Notice of Opposition dated Jun. 12, 2001. EPOPWH2–02.

Murray, Y., "Tradition Rather Than Cure", Wound Care, Nursing Times, Sep. 21, vol. 84, No. 38, 1988. NPL–304.

*Kinetic Concepts, Inc., et al.,* v. *Bluesky Medical Corporation, et al.,* Civil Action No. SA03–CA–0832–RF, U.S. District Court, W. Dist of Texas San Antonio Div., Plaintiffs Response to Clain Construction Reply Letter dated Jan. 6, 2006. BS–142.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendants Medela Claim Construction Letter dated Jan. 5, 2006. BS–143.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Harriet W. Hopf, M.D. on New Claims dated Jan. 4, 2006. BS–2.

*Kinetic Concepts, Inc., et al.,* v. *Bluesky Medical Cororation, et al.,* Civil Action No. SA–03–CA–0832–RF, U.S. District Court, W. Dist. of Texas San Antonio Div., Expert Report of Lydia Razran Stone, Ph.D. dated Dec. 29, 2005 with CV. BS–3.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs Fourth Amended Complaint with Declaration of Trang Tran with Exhibits dated Jun. 30, 2005. BS–144.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcript Deposition of Michael John Morykwas dated Dec. 6, 2005 with Exhibits. BS–64.

Spurlock, Gareth, "The Management of Open Joint Injuries", Wound Management, Veterinary Clinics of North American Equina Practice, vol. 5, No. 3, Dec. 1989. NPL–386.

Tittel, K., et al., "VariDyne—new standards in postoperative wound drainge", Jahrgang 14 91988), Nr. 2, Apr., vol. 14 (1988), No. 2, Apr., pp. 104–107. NPL–403.

Queen, D., et al., "The preclinical evaluation of the Water Vapour Transmission Rate Through Burn Wound Dressings", Biomaterials 1987 vol. 8, Sep., pp. 367–371. NPL–337.

Wood, R.A.B., et al., "Foam Elastomer Dressing in the Management of Open Granulating Wounds: Experience with 250 Patients", Br. J. Surg., vol. 64 (1977), pp. 554–557. NPL–443.

Waymack, J.P., et al., "An Evaluation of Aquaphor Gauze Dressing in Burned Children", Burns (1986) 12, 443–448. NPL–428.

Winter, George D., "Epidermal Wound Healing Under a New Polyurethane Foam Dressing (Lyofoam)", Plastic & Reconstructive Surgery, Nov. 1975, Vo. 56, No. 5, pp. 531–537. NPL–438.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition Transcript of Doris Ritter–Wiegand with Exhibits dated Dec. 15, 2005. BS–65.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcript of Videotaped Deposition of Katherine Jeter with Exhibits dated Nov. 29, 2005. BS–66.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Supplemental Expert Report of Mark Chariker, M.D. dated Dec. 19, 2005. BS–24.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Vincent B. Pizziconi, Ph.D. with Exhibits dated Dec. 23, 2005. BS–5.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Amended Order Construing Patent '643 Claims Terms dated Jan. 25, 2006. BS–145.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Order Construing Patents '643 and '081 Claim Terms dated Jan. 24, 2006. BS–146.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Michael A. O'Neil dated Jan. 4, 2006. BS–6.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Partial Transcript of Videotaped Deposition James Spahn dated May 4, 2005. BS–67.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Report of Professor Thomas K. Hunt, M.D., pp. 1–14, (with exhibits) Jan. 13, 2005. BS–29.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Report of Mark Chariker, M.D., pp. 1–8, Jan. 13, 2005. BS–8.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Report of James Spahn, M.D., pp. 1–6 and Exhibit C pp. 9–10, Jan. 6, 2005. BS–9.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Michael H. Baniak, pp. 1–79 and Exhibit D pp. 1–3 including un–published materials listed therein and Exhibit E pp. 1–5, Jan. 7, 2005. BS–10.

*Kinetic Concepts, Inc., et al.,* v. *Bluesky Medical Corporation, et al.,* Civil Action No. SA–03–CA–0832–RF, U.S. Dist. Count, W. Dist. of TX San Antonio Div., Report of Katherine F. Jeter, Nov. 28, 2004. BS–11.

*Kinetic Concepts, Inc., et al.,* v. *Bluesky Medical Corporation, et al.,* Civil Action No. SA–03–CA–0832–RF, U.S. Dist. Count, W. Dist. of TX San Antonio Div., Report of Wilson C. Hayes, Ph.D, Nov. 29, 2004, pp. 1–15, and Exhibit C (2 pages). BS–12.

Banwell, P, et al., "Topical Negative Pressure TNP Focus Group Meeting", Proceedings, London, UK 2003, pp. 1–111. WFU–24.

Proceedings from the 2003 National V.A.C.® Education Conference, supplement to the Apr. 2004 Wounds, 40 pages. NPL–335.

Dieu, T., et al., "Too Much Vacuum–Assisted Closure", ANZ J. Surg. 2003; 73: 105–71060 NPL–117.

Chester, D., et al., "Adverse Alteration of Wound Flora with Topical Negative–Pressure Therapy: A Case Report", British Journal of Plastic Surgery, 2002, pp. 510–511. NPL–082.

Alvarez, A., et al., "Vacuum–Assisted Closure for Cutaneous Gastrointestinal Fistual Management", Gynecologic Oncology, 80, 413–416 (2001). NPL–015.

Nienhuijs, S.W., et al., "Can Topical Negative Pressure Be Used To Control Complex Enterocutaneous Fistulae?", Journal of Wound Care, V. 12, No. 9, Oct. 2003, pp. 343–345. NPL–313.

Erdmann, D., et al., "Abdominal Wall Defect and Enterocutaneous Fistula Treatment with the Vacuum–Assisted Closure (V.A.C.) System", Plastic and Reconstructive Surgery, vol. 108, No. 7, pp. 2066–2068 (Dec. 2001). NPL–141.

Maddin, W. Stuart, et al., "The Biological Effects of a Pulsed Electrostatic Field with Specific Reference to Hair", Pharmacology and Therapeutics, Jul.–Aug. 1990, V. 29, No. 6, pp. 446–450. NPL–263.

Morykwas, M. and Argenta, L., "Use of Negative Pressure to Increase the Rate of Granulation Tissue Formation in Chronic Open Wounds", The FASEB Journal, Experimental Biology '93, New Orleans, Louisiana, Mar. 28–Apr. 1, 1993, 800 (Feb. 19, 1993). WFU–13.

Orringer, Jay, et al., "Management of Wounds in Patients with Complex Enterocutaneous Fistulas", Surgery, Gynecology & Obstetrics, Jul. 1987, V. 165, pp. 79–80. NPL–323.

Lohman, R., et al., "Discussion: Vacuum Assisted Closure: Microdeformations of Wounds and Cell Proliferation", Plastic and Reconstructive Surgery, Oct. 2004, pp. 1097–1098. NPL–257.

Defranzo, A.J., et al., "109: Use of Sub–Atmospheric Pressure for Treatment of Gunshot Injuries", Plastic Surgical Forum, V. XXIII, Los Angeles, CA, Oct. 14–18, 2000, pp. 180–181. WFU–05.

Marks, M., et al., "Management of Complex Soft Tissue Defects in Pediatric Patients Using the V.A.C. Wound Closure", Plastic Surgical Forum, V. XXI, Boston, MA, Oct. 3–7, 1998, pp. 215–216. WFU–09.

Morykwas, M. and Argenta, L., "Use of Negative Pressure to Prevent Progression of Partial Thickness Burns", American Burn Association, V. 26, $26^{th}$ Annual Meeting, Apr. 20–23, 1994, Orlando, Florida, pp. 157. WFU–14.

Morykwas, M. and Argenta, L., "Vacuum Assisted Closure (VAC Therapy) for Secondary Closure of Dehisced and Infected Wounds", Wound Repair and Regeneration, Jul.–Sep. 1995, pp. 361. WFU–11.

Morykwas, M. and Argenta, L., "Treatment of Burned Extremities Using Vacuum Therapy (The V.A.C.)", Wound Repair and Regeneration, V. 3, N. 3, Jul.–Sep. 1995, pp. 367. WFU–15.

Webb, L. and Morykwas, M., et al., "The Use of Vacuum–Assisted Closure in Composite Wound Management", The Third Riva Congress, Current Perspectives in Fracture Management and Orthopaedic Reconstruction, May 10–14, 2000, Italy, pp. 137. WFU–20.

Morykwas, M. and Webb, L., "Sub–Atmospheric Pressure for the Treatment of Lower Extremity Wounds", The Third Riva Congress, Current Perspectives in Fracture Management and Orthopaedic Reconstruction, May 10–14, 2000, Italy, pp. 135–136. WFU–18.

Argenta, L., et al., "Use of V.A.C. for Treatment of Dehisced Sternal Incisions", Plastic Surgical Forum, V. XXIII, Los Angeles, CA, Oct. 14–18, 2000, pp. 172–174. WFU–06.

Morykwas, M., et al., "Isolated Muscle Flap Survival with Complete Venous Occlusion: Varying Delay in External Application of Sub–atmospheric Pressure", Plastic Surgical Forum, V. XXi, Boston, MA, Oct. 3–7, 1998, pp. 237. WFU–16.

Morykwas, M., et al., "Vacuum–Assisted Closure: A New Method for Wound Control and Treatment: Animal Studies and Basic Foundation", Annals of Plastic Surgery, V. 38, N. 6, Jun. 1997, pp. 553–562. WFU–29.

Argenta, L. and Morykwas, M., "Vacuum–Assisted Closure: A New Method for Wound Control and Treatment: Clinical Experience", Annals of Plastic Surgery, V. 38, N. 6, Jun. 1997, pp. 563–577. WFU–31.

Morykwas, M. and Argenta, L., "V.A.C. Experience and Difficult Wounds", des Journees Regionales des Plaies et Cicatrisations, Sep. 22–23, 1997, pp. 76–90. WFU–01.

Genecov, D., et al., "A Controlled Subatmospheric Pressure Dressing Increases the Rate of Skin Graft Donor Site Reepithelialization", Annals of Plastic Surgery, V. 40, N. 3, Mar. 1998, 219–225. WFU–28.

Morykwas, M. and Argenta, L., "Techniques in Use of V.A.C.™ Treatment", ACA—Acta Chir. Austriaca, Supplement NR. 150, 1998, pp. 3–4 of 2–28. WFU–02.

Morykwas, M. and Argenta, L., "Use of the V.A.C.™ For Treament of a Traumatic Left Hip Disarticulation", ACA—Acta Chir. Austriaca, Supplement Nr. 150, 1998, pp. 24–25 and cover sheet. WFU–12.

Morykwas, M., et al., "Use of Subatmospheric Pressure to Prevent Progression of PartialpThickness Burns in a Swine Model", Journal of Burn Care & Rehabilitation, Jan./Feb. 1999, pp. 15–21. WFU–03.

Banwell, P., et al., "Application of Topical Sub–Atmospheric Pressure Modulates Inflammatory Cell Extravasation in Experimental Partial Thickness Burns", Wound Repair and Regeneration, Jul./Aug. 1999, V. 7, N. 4, pp. A286–287. WFU–08.

Morykwas, M., et al., "Use of Subatmospheric Pressure to Prevent Doxorubicin Extravasion Ulcers in a Swine Model", Journal of Surgical Oncology, 199; 72:14–17. WFU–33.

Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation. WFU–07.

Mooney, J., et al., "Treatment of Soft Tissue Defects in Pediatric Patients Using the V.A.C.™ System", Clinical Orthopaedics and Related Research, No. 376, Jul. 2000, p. 26–31. WFU–26.

Morykwas, M., et al., "The Effect of Externally Applied Subatmospheric Pressure on Serum Myoglobin Levels After a Prolonged Crused/Ischemia Injury", The Journal of Trauma Injury, Infection and Critical Care, Sep. 2002, V. 53, N. 3, pp. 537–540. WFU–19.

Molnar, J., et al., "Acclerationof Integra Incorporation in Complex Tissue Defects with Subatmospheric Pressure", Plastic and Reconstructive Surgery, Apr. 15, 2004, pp. 1339–1346. WFU–10.

Morykwas, M. and Argenta, L., "Nonsurgical Modalities to Enhance Healing and Care of Soft Tissue Wounds", Journal of the Southern Orthopaedic Association, V. 6, N. 4, 1997, pp. 279–288. WFU–04.

Schneider, A., et al., "A New and Reliable Method of Securing Skin Grafts to the Difficult Recipient Bed", Plastic and Reconstructive Surgery, Sep. 1998, pp. 1195–1198. WFU–30.

Rosser, C., et al., "A New Technique to Manage Perineal Wounds", Infections in Urology, Mar./Apr. 2000, V. 13, N.2, pp. 45–47 & 56. WFU–34.

Defranzo, A.J., et al., "The Use of Vacuum–Assisted Closure Therapy for the Treatment of Lower–Extremity Wounds with Exposed Bone", Plastic and Reconstructive Surgery, Oct. 2001, V. 108, N. 5, pp. 1184–1191. WFU–25.

Morykwas, M., "The Use of The V.A.C. Wound Treatment System for Acute and Subacute Wounds", Plaies & Cicatrices, Would Closure Healing, Apr. 21, 22 and 23, 1999. WFU–17.

Webb, L., et al., "Negative Pressure Wound Therapy in the Management of Orthopedic Wounds", Ostomy Wound Management, Apr. 2004, V. 50, Issue 4A (Suppl.), pp. 26–27 and cover sheet. WFU–22.

Webb, L., et al., "Wound Management With Vacuum Therapy", English abstract from website printout and German article, http://www.ncbi_nlm_nih.gov/entrez/query.fcgi?cmd=Retrieve&db=pubmed&dot=Abstra ..., Dec. 2, 2004, 2 pages website printout, German article, Oct. 2001, pp. 918–926. WFU–23.

Webb, "New Techniques in Wound Management: Vacuum–Assisted Wound Closure", Journal of the American Academy of Orthopaedic Surgeons, V. 10, N. 5, Sep./Oct. 2002, pp. 303–311. WFU–21.

Morkywas, M. and Argenta, L., "Sub–Atmospheric Pressure Wound Treatment and Cultured Keratinocyte Allografts, Cultured Human Keratinocytes and Tissue Engineered Skin Substitutes", © 2001 Georg Thieme Verlag, pp. 343–346. WFU–27.

Molnar, J., et al., "Single–Stage Approach to Skin Grafting the Exposed Skull", Plastic and Reconstructive Surgery, Jan. 2000, V. 105, N. 1, 174–177. WFU–32.

Scherer, L, et al., "The Vacuum Assisted Closure Device: A Method of Securing Skin Grafts and Improving Graft Survival", Arch. Surg., V. 137, Aug. 2002, pp. 930–934. NPL–359.

Defranzo, A., et al., "Vacuum–Assisted Closure for the Treatment of Degloving Injuries", Plastic and Reconstructive Surgery, Dec. 1999, V. 104, N. 7, pp. 2145–2148. WFU–35.

Miller, P., et al., "Late Fascial Closure in Lieu of Ventral Hernia: The Next Step in Open Abdomen Management", the Journal of Trauma Injury, Infection and Critical Care, Nov. 2002, V. 53, N. 5, pp. 843–849. NPL–288.

Betancourt, S., "A Method of Collecting the Effluent From Complicated Fistula of the Small Intestine", 1986, p. 375. NPL–045.

Dorland's Illustrated Medical Dictionary, Twenty–Fifth Edition, 1974, pp. 1112. NPL–120.

Hopf, H., et al., "Adjuncts to preparing wounds for closure Hyperbaric oxygen, growth factors, skin substitutes, negative pressure wound therapy (vacuum–assisted closure)", Foot Ankle Clin N Am 6, 2001, pp. 661–682. NPL–211.

Chariker–Jeter® Wound Drainage Kit, BlueSky Medical, 2 page advertisement with copy of business card from Quality Medical Supply. NPL–077.

Chariker–Jeter® Wound Drainage Kit Instructions, Item #500.7777, BlueSky Medical, 2 pages. NPL–076.

Wooding–Scott® Wound Drainage Kit Contents, Item #500.8888, 1 page. NPL–445.

Montgomery, B., "Easy Dressing of Large, Draining Abdominal Wounds using Moisture Vapor–Permeable Film", pp. 417–418, Techniques for Surgeons, Wiley Medical Publication, © 1985. NPL–297.

Davydov, Y., et al., "Pathogenic Mechanism of the Effect of Vacuum Therapy on the Course of the Wound Process", Jun. 1990, 16 pages of English Translation and abstract. DV13.

Borzov, M., et al., "Vacuum Therapy of Some Skin Diseases", Vestnik dermatologii venerologii, n. 8, Aug. 1965, pp. 50–56,(13 pages of English translation by R. McElroy and 1 sheet printout from PubMed). NPL–055.

Herrmann, L., et al., "The Pavaex (Passive Vascular Exercise) Treatment of Obliterative Arterial Diseases of the Extremeties", The Journal of Medicine, Dec. 1933, pp. 524–529. NPL–200.

Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697–704. NPL–198.

Sturr, R., Evaluation of Treatment of Peripheral Vascular Disease by Alternating Positive and Negative Pressure, Philadelphia, Archives of Physical Therapy, Sep. 1938, pp. 539–543. NPL–392.

Balin, A., et al., "Oxygen Modulates Growth of Human Cells at Physiologic Partial Pressures", Laboratory for Investigative Dermatology, J. Exp. Med. ©, the Rockefeller University Press, v. 160, Ju.. 1984, pp. 152–166. NPL–029.

Saran Resins and Films, "Fresh Thinking". website printout, 6 pages, Jan. 20, 2004. NPL–354.

Bluesky Medical, "A Leader in Suction Technology—Wound Drainage Experts", printout of website, 55 pages, Apr. 8, 2003, www.blueskymedical.com. NPL–052.

Garcia–Rindaldi, R., et al., "Improving the Efficiency of Wound Drainage Catheters", v. 130, Sep. 1975, pp. 372–373. NPL–169.

Davydov, et al., "Would Healing Under the Conditions of Vacuum Draining", Khirurgiia (Mosk) 1992, (7–8):21–6 (with English translation by Scientific Translation Services). DV14.

Davydov, et al., "Vacuum therapy in the treatment of acute suppurative diseases of soft tissue and suppurative wounds", Vestn. Khir. Sep. 1988 (with English translation by Ralph McElroy Co.). DV10.

Coyle, M., et al., "A Case Study: Positive Outcomes to Negative Pressure Wound Therapy—A collaborative assessment", Hospital of Saint Raphael, 1 page charge. NPL–102.

Nemoto, H., et al., "Stories From the Bedside: Purple Urine Bage Syndrome Development in Ileal Conduit", WCET, Journal 23(2), pp. 31–34. NPL–310.

Baker, B., "Negative–Pressure Therapy Looks Promising", Skin & Allergy News, Feb. 2000, p. 14. NPL–028.

McCallon, S., et al., "Vacuum–Assisted Closure versus Saline–Moistened Gauze in the Healing of Postoperative Diabetic Foot Wounds", Ostomy Wound Management, Aug. 2000, v.46, Issue 8.pp. 28–29, 31–32, 34. NPL–269.

Clinicians' Pocket Guide to Chronic Wound Repair, Wound Healing Publications, Second Edition, © 1992, 106 pages. NPL–300.

Biblehimer, H., "Dealing with A Wound That Drains 1.5 Liters A Day", RN, Aug. 1986, pp. 21–23. NPL–046.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report of Dennis P. Orgill, M.D., Ph.D., Feb. 18, 2005. BS–13.

*Kinetic Concepts, Inc., et al., v. Bluesky Medical Corporation, et al.,* Civil Action No. SA–03–CA–0832–RF, U.S. District Court, W. Dist. of Texas San Antonio Div., Rebuttal Expert Report of Wilson C. Hancs, Ph.D. in Response to the Report of Michael H. Baniak (Feb. 18, 2005). BS–14.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report of John T. Goolkasian in Rebuttal to Report of Michael H. Baniak (Feb. 18, 2005). BS–15.

*Kinetic Concepts, Inc., et al., v. Bluesky Medical Corporation, et al.,* Civil Action No. SA–03–CA–0832–RF, U.S. District Court, W. Dist. of Texas San Antonio Div., Rebuttal Expert Report of Louis C. Argenta, M.D. to Expert Report of Michael H. Baniak (Feb. 18, 2005). BS–16.

Banwell, P. et al., "Topical Negative Pressure TNP Focus Group Meeting", Proceedings, London, UK, 203, pp. 112–232. WFU–24.

*Kinetic Concepts, Inc., et al., v. Bluesky Medical Corporation, et al.,* Civil Action No. SA–03–CA–0832–RF, U.S. District Court, W. Dist. of Texas San Antonio Div., Ordering Adopting Stipulations of Parties Regarding Claim Term Construction dated May 12. 2005. BS–171.

*Kinetic Concepts, Inc., et al., v. Bluesky Medical Corporation, et al.,* Civil Action No. SA–03–CA–0832–RF, U.S. District Court, W. Dist. of Texas San Antonio Div., Order Construing Patent '643 Claim Terms dated Jun. 28, 2005. BS–172.

Opposition EP to 0,620,720, Patentee's Response to Grounds of Appeal Filed By Opponent, Paul Hartmann AG dated Apr. 25, 2006. EPOPWH1–16.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiff's Fourth Amended Complaint dated Jun. 30, 2005. BS–173.

*Kinetic Concepts, Inc., et al., v. Bluesky Medical Corporation, et al.,* Civil Action No. SA–03–CA–0832–RF, U.S. District Court, W. Dist. of Texas San Antonio Div., Kinetic Concepts, Inc.'s Supplemental Answers to Bluesky Medical Corporation's First Set of Interrogatories dated Jul. 6, 2005. BS–174.

*Kinetic Concepts, Inc., et al., v. Bluesky Medical Corporation, et al.,* Civil Action No. SA–03–CA–0832–RF, U.S. District Court, W. Dist. of Texas San Antonio Div., KCI Licensing, Inc.'s Supplemental Answers to Medela, Inc.'s First Set of Interrogatories dated Jul. 6, 2005. BS–175.

*Kinetic Concepts, Inc., et al., v. Bluesky Medical Corporation, et al.,* Civil Action No. SA–03–CA–0832–RF, U.S. District Court, W. Dist. of Texas San Antonio Div., Wake Forest University Health Sciences' Supplemental Answers to Medela Inc.'s First Set of Interrogatories dated Jul. 6, 2005. BS–176.

*Kinetic Concepts, Inc., et al., v. Bluesky Medical Corporation, et al.,* Civil Action No. SA–03–CA–0832–RF, U.S. District Court, W. Dist. of Texas San Antonio Div., Amended Answer to Third Amended Complaint, Additional Defenses, Second Amended Counterclaims and Jury Demand of Medela, Inc. dated Apr. 29, 2005. BS–177.

*Kinetic Concepts, Inc., et al., v. Bluesky Medical Corporation, et al.,* Civil Action No. SA–03–CA–0832–RF, U.S. District Court, W. Dist. of Texas San Antonio Div., Answer to Third Amended Complaint, Additional Defenses, Amended Counterclaims and Jury Demand of Defendant Medela AG dated Feb. 11, 2005. BS–178.

*Kinetic Concepts, Inc., et al., v. Bluesky Medical Corporation, et al.,* Civil Action No. SA–03–CA–0832–RF, U.S. District Court, W. Dist. of Texas San Antonio Div., Deposition transcript with Exhibits of Mark Chariker dated May 6, 2005. BS–76.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of David S. Zamierowski dated Feb. 15, 2005. BS–77.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Harriet W. Hopf dated May 10, 2005, along with Supplemental Expert Report with Exhibits dated May 25, 2005. BS–17.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Susan Mendez–Eastman dated Jan. 7, 2004. BS–18.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Jose Diaz dated Nov. 26, 2004. BS–19.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Jeffrey Niezgoda dated Nov. 23, 2004. BS–20.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Kathleen Satterfield dated Nov. 29, 2004. BS–21.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Exhibits 281–288 of previously submitted Transcription of Deposition of Michael John Morykwas, PhD. dated Jan. 13, 2005. BS–78.

Thomas, S., et al., "Comparative Review of the Properties of Six Semipermeable Film Dressings", The Pharmaceutical Journal, Jun. 18, 1988, pp. 785–789. NPL–402.

Baker, B., "Abundance of Web Sites on Wound Care Management", Family Practice News, Mar. 1, 2000, pp. 52. NPL–027.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27–29. NPL–101.

Townsend, P.L.G., "The Quest For A Cheap and Painless Donor–Site Dressing", Burns, 2, pp. 82–85 (Jan. 1976). NPL–404.

Langworthy, M., et al., "Treatment of the Mangled Lower Extremity After a Terrorist Blast Injury", Clinical Orthopaedics and Related Research, No. 422, pp. 88–96 (May 2004). NPL–251.

Park, G.B., et al., "The Design and Evaluation of a Burn Wound Covering", Supplied by The British Library—"The Word's Knowledge", pp. 11–15 (1978). NPL–327.

Acu–derm® Transparent Moisture, Vapor Permeable Polyurethane Dressing, pp. 1–13 and cover sheet. NPL–003.

3M Ioban 2, Breathability, Conformability and Strength, Breathability—Moisture Vapor Transmission Rate and Conformability and Strength—Tensile Strength, Elongation and Fn Modulus Test (1 page). NPL–001.

"Moist Wound Dressings" from Physicians Instruction Book for Moist Wound Healing. NPL–295.

Svedman, P., "A dressing allowing continuous treatment of a biosurface," IRCS Medical Science: Biomedical Technology; Clinical Medicine; Surgery and Transplantation, 7:221 (1979). (Exhibit D–407). NPL–387.

Johnson, F., "An Improved Technique for Skin Graft Placement Using a Suction Drain," Surgery, Gynecology & Obstetrics, p. 585–586, Dec. 1984, (Exhibit D132). NPL–226.

Davydov, Y., et al., "Bacteriological and Cytological Assessment of Vacuum Therapy of Purulent Wounds," Vestn. Khir., 48–52, English translation by IRC, (Oct. 1988). (Exhibit D–290). NPL–616.

Davydov, Y., et al. "Vacuum Therapy in the Treatment of Purulent Lactation Mastitis", Vestn. Khir. p. 66–70, English translation by IRC, (Sep. 1986), (Exhibit D–292). NPL–617.

Meyer, W., et al., "Bier's Hyperemic Treatment," W.B. Saunders & Co., 1908 (Exhibit D246) NPL–283.

Chariker/Jeter/Tintle Slides "Closed Wound Suction" by Dr. Mark Chariker et al., 41 sheets, pp. 1–10, 19, 55–84 (D–041) (allegedly dated 1985 and 1986) NPL–079.

Jeter, K., list of publications, 4 sheets (D–161) NPL–225.

Chariker/Jeter, Spartanburg General Hospital Progress Notes, dated 1986, 25 pages, (Exhibit D–158) NPL080.

Spahn/Hamaker slide entitled "Poor man's irrigation/vacuum dressing used since 1970's," (Exhibit D–135) NPL–382.

*KCI* v. *BlueSky,* Final Jury Instructions, 84 pages, delivered by jury Jul., 14, 2006. BS–207.

*KCI* v. *BlueSky*, Trial Transcript, dated Jun. 1, 2006 BS–99.

*KCI* v. *BlueSky*, Trial Transcript of Argenta, dated Jun. 2, 2006 BS–100.

*KCI* v. *BlueSky*, Trial Transcript of Argenta/Morykwas, dated Jun. 5, 2006 BS–101.

*KCI* v. *BlueSky*, Trial Transcript of Morykwas/Leininger/Weston, dated Jun. 6, 2006 BS–102.

*KCI* v. *BlueSky*, Trial Transcript of Weston, dated Jun. 7, 2006 BS–103.

*KCI* v. *BlueSky*, Trial Transcript of Weston, dated Jun. 8, 2006 BS–104.

*KCI* v. *BlueSky*, Trial Transcript of Niezgoda, dated Jun. 9, 2006 BS–105.

*KCI* v. *BlueSky*, Trial Transcript of Miller/Anderson/Ware, dated Jun. 19, 2006 BS –106.

*KCI* v. *BlueSky*, Trial Transcript of Ware/Resietter/Condor/Malackowski, dated Jun. 20, 2006 BS–107.

*KCI* v, *BlueSky*, Trial Transcript of Malackowski/Dairman/Leszkiewicz/Banes/John, dated Jun. 21, 2006 BS–108.

*KCI* v. *BlueSky*, Trial Transcript of Johnson/Quackenbush, dated Jun. 29, 2006 BS–109.

*KCI* v.*BlueSky*, Trial Transcript of Quackenbuch/Laurel, dated Jun. 30, 2006 BS–110.

*KCI* v. *BlueSky*, Trial Transcript for Escobedo/Satterfield/Chariker, dated Jul. 5, 2006 BS–111.

*KCI* v. *BlueSky*, Trial Transcript for Chariker/Hamaker/Spahn/Jeter/Hopf, dated Jul. 6, 2006 BS–112.

*KCI* v. *BlueSky*, Trial Transcript for Hopf/Lockhart, dated Jul. 7, 2006 BS–113.

*KCI* v. *BlueSky*, Trial Transcript for Hopf, dated Jul. 10, 2006 BS–114.

*KCI* v. *BlueSky*, Trial Transcript for Pizziconi/Orgill, dated Jul. 11, 2006 BS–115.

*KCI* v. *BlueSky*, Trial Transcript for Orgill/Bridi/McGregor/Girolami/Taylor, dated Jul. 12, 2006 BS–116.
*KCI* v. *BlueSky*, Trial Transcript for Campbell, dated Jul. 13, 2006 BS–117.
*KCI* v. *BlueSky*, Trial Transcript dated Jul. 14, 2006 BS–118.
*KCI* v. *BlueSky*, Trial Transcript dated Jul. 17, 2006 BS–119.
*KCI* v. *BlueSky*, Expert Report of Mark Chariker, with Exhibits, dated Jan. 7, 2005. BS–23.
*KCI* v. *BlueSky*, Supplemental Expert Report of Mark Chariker, M.D., with Exhibits, dated Dec. 19, 2005. BS–24.
*KCI* v. *BlueSky*, Supplemental Expert Report of Harriet Hopf, with Exhibits, dated Nov. 18, 2005. BS–25.
*KCI* v. *BlueSky*, Amended Expert Report of Harriet W. Hopf, M.D. on New Claims, with Exhibits, dated Feb. 10, 2006. BS–26.
*KCI* v. *BlueSky*, Expert Report of Harriet W. Hopf, M.D. Responsive to Plaintiff's Asserted Claims for Relief, with Exhibits, dated Feb. 10, 2006. BS–27.
*KCI* v. *BlueSky*, Supplemental Expert Report of Harriet W. Hopf, M.D. with Exhibits, dated Jun. 23, 2006. BS–28.
*KCI* v. *BlueSky*, Report of Katherine F. Jeter, with Exhibits, dated Nov. 28, 2004. BS–11.
*KCI* v. *BlueSky*, Supplemental Expert Report of Michael O'Neil, dated Feb. 22, 2006. BS–31.
*KCI* v. *BlueSky*, Rebuttal Expert Report of Harriet W. Hopf, M.D. with Exhibits, dated Mar. 11, 2008. BS–32.
*KCI* v. *BlueSky*, Rebuttal Report to Plaintiffs' Rebuttal Expert Report by Michael O'Neil, dated Mar. 12, 2006. BS–33.
*KCI* v. *BlueSky*, Attachments to Expert Report of Michael A. O'Neil. BS–34.
*KCI* v. *BlueSky*, Expert Report of Vincent Pizziconi, with Exhibits, dated Dec. 31, 2005. BS–35.
*KCI* v. *BlueSky*, Amended Expert Report of Vincent B. Pizziconi, Ph.D., with Exhibits, dated Feb. 6, 2006. BS–36.
*KCI* v. *BlueSky*, Expert report of Vincent B. Pizziconi, Ph.D. responsive to plaintiff's asserted claims for relief, with exhibits, dated Feb. 14, 2008. BS–37.
*KCI* v. *BlueSky*, Amended expert report of Vincent B. Pizziconi, Ph.D. responsive to plaintiff's asserted claims for relief, with exhibits, dated Feb. 16, 2006. BS–38.
*KCI* v. *BlueSky*, Rebuttal Expert Report of Vincent B. Pizziconi, Ph.D., with Exhibits, dated Mar. 12, 2006. BS–39.
*KCI* v. *BlueSky*, Supplemental Expert Report of Vincent B. Pizziconi, Ph.D. with Exhibits, dated Jun. 23, 2006. BS–40.
*KCI* v. *BlueSky*, Supplemental expert report of Lydia Razran Stone, Ph.D., with exhibits, dated Mar. 8, 2006. BS–41.
*KCI* v. *BlueSky*, Expert Report of Lydia Razran Stone, Ph.D., with Exhibits, dated Dec. 29, 2005. BS–42.
*KCI* v. *BlueSky*, Expert Report of Louis C. Argenta in Response to Report of Katherine Jeter, with Exhibits, dated Jan. 5, 2005. BS–43.
*KCI* v. *BlueSky*, Responsive Expert Report of Louis C. Argenta to Reports of Hopf, O'Neil, Pizziconi & Chariker, dated Feb. 27, 2006. BS–44.
*KCI* v. *BlueSky*, Responsive Expert Report of Louis C. Argenta to Supplemental Expert Report of O'Neil, dated Mar. 13, 2006. BS–45.
*KCI* v. *BlueSky*, Rebuttal Report of Louis C. Argenta in Response to James Spahn, Mark Chariker & Thomas Hunt. BS–46.
*KCI* v. *BlueSky*, Responsive Expert Report of Louis C. Argenta, M.D. to Expert Supplemental Reports of Hopf and Pizziconi, with Exhibits, dated Jul. 8, 2006. BS–47.

*KCI* v. *BlueSky*, Responsive Expert Report of Valery Gilevich, M.D. to Expert Report of Lydia Razran Stone, Ph.D. BS–48.
*KCI* v. *BlueSky*, Expert Report of Valery Gilevich, dated Dec. 14, 2004, with Exhibits (Exhibit P–47). BS–49.
*KCI* v. *BlueSky*, Rebuttal expert report of John T. Goolkasian, dated Feb. 22, 2006. BS–50.
*KCI* v. *BlueSky*, Supplemental Rebuttal Expert Report of John T. Goolkasian, with Exhibits, dated Mar. 10, 2006. BS–51.
*KCI* v. *BlueSky*, Report of Wilson C. Hayes, PhD, with Exhibits, dated Nov. 29, 2004. BS–12.
*KCI* v. *BlueSky*, Expert Report of Wilson Hayes in Response to Reports of James Spahn and Mark Chariker, with Exhibits, dated Jan. 31, 2005. BS–53.
*KCI* v. *BlueSky*, Expert Report of Wilson Hayes in Response to Report of Katherine Jeter, with Exhibits, dated Jan. 7, 2005. BS–54.
*KCI* v. *BlueSky*, Supplemental Expert Report of Wilson C. Hayes, Ph.D. Concerning Infringement of Newly Asserted Claims of U.S. Patent Nos. 5,636,643 and 5,645,081, with Exhibits, dated Dec. 19, 2005. BS–55.
*KCI* v. *BlueSky*, Responsive Expert Report of Wilson Hayes in Response to Hopf, Chariker, Izziconi, and O'Neil Regarding Patent Validity, with Exhibits, dated Feb. 27, 2006. BS–56.
*KCI* v. *BlueSky*, Rebuttal Expert Report Wilson C. Hayes, Ph.D. in Response to the Reports of Harriet Hopf and Vincent Pizziconi Regarding Plaintiffs' Asserted Claims for Relief, with Exhibits. (Mar. 7, 2006). BS–57.
*KCI* v. *BlueSky*, Expert Report of Jeffery Niezgoda in Response to Katherine Jeter, dated Jan. 7, 2005. BS–58.
*KCI* v. *BlueSky*, Expert Report of Jeffery Niezgoda in Response to James Spahn, Thomas Hunt & Mark Chariker, dated Jan. 31, 2005. BS–59.
*KCI* v. *BlueSky*, Supplement to Expert Report of Jeffery Niezgoda, with Exhibits, dated Jan. 4, 2006. BS–60.
*KCI* v. *BlueSky*, Expert Report of Dennis P. Orgill, M.D., Ph.D., with Exhibits, dated Feb. 20, 2006. BS–61.
*KCI* v. *BlueSky*, Rebuttal Expert Report of Dennis Orgill to Amended Expert Reports of Harriet Hopf and Vincent Pizziconi, with Exhibits, dated Mar. 13, 2006. BS–62.
*KCI* v. *BlueSky*, Supplemental Expert Report of Dennis P. Orgill, M.D., Ph.D., with Exhibits, dated Jul. 6, 2006. BS–63.
*KCI* v. *BlueSky*: BlueSky Medical Group Inc. and Richard Weston's motion to exclude certain expert testimony dated Apr. 21, 2006. Bs–208.
*KCI* v. *BlueSky*: Medela's Motion to exclude proposed trial testimony of plaintiff's experts Louis C. Argenta, Dennis P. Orgill and Wilson C. Hayes, dated Apr. 21, 2006. BS–209.
*KCI* v. *BlueSky*: Plaintiff's motion to exclude opinions of Vincent Pizziconi dated Apr. 21, 2006. BS–210.
*KCI* v. *BlueSky*: Plaintiff's motion to exclude certain opinions of Michael O'Neil dated Apr. 21, 2006. BS–211.
*KCI* v. *BlueSky*: Medela's response to plaintiff's motion to exclude opinions of Harriet Hopf with Exhibits dated Apr. 28, 2006. BS–212.
*KCI* v. *BlueSky*: Medela's response to plaintiff's motion to exclude opinions of Michael O'Neil and motion to exclude opinions of John T. Goolkasian with Exhibits dated Apr. 28 2006. BS–213.

*KCI* v. *BlueSky*: Medela's response to plaintiff's motion to exclude opinions of James Spahn dated Apr. 28, 2006. BS–214.
*KCI* v. *BlueSky*: Plaintiff's response to Medela's motion to exclude proposed trial testimony of Louis C. Argenta, Dennis P. Orgill, and Wilson C. Hayes, dated May 1, 2006. Bs–215.
*KCI* v. *BlueSky*: Medela's Renewed Motion for Judgment as a Matter of Law, or, in the alternative, a New Trial, on Patent Invalidity, dated Sep. 3, 2006. BS–216.
*KCI* v. *BlueSky*: Medela's Motion for a New Trial on Unenforceability, dated Sep. 13, 2006. BS–217.
Claim Chart of Asserted Claims of U.S. Patent 5,636,643 to Argenta, 3 pages. BS–218.
Claim Invalidity Analysis of U.S. Patent 5,636,643 to Argenta, et al., 34 pages, Mar. 2004. BS–219.
*KCI* v. *BlueSky*: Letter dated Dec. 9, 2005 from the Honorable Royal Ferguson to attorneys in *KCI* v. *BlueSky* regarding claim construction. BS–220.
*KCI* v. *BlueSky*, Letter from Valery Gilevich, M.D. to Kirt S. O'Neil, dated May 28, 2006 concerning review of English translation of Russian article. BS–221.
*KCI* v. *BlueSky*, Second Amended Order Construing Patent '643 and '081 Claim Terms dated Jun. 29, 2006. BS–222.
Alexander, J.W., et al., "Clinical evaluation of epigard, a new synthetic substitute for homograft and heterograft skin," J. of Trauma, 13:374–383, (1973) NPL–010.
Anon., "Standard Test Methods for Water Vapor Transmission of Materials," ASTM, Designation: E 96/E 96M–05, Published Jun. 2005, 11 sheets, (Exhibit D–184) NPL–017.
Bertone, A.L., et al., "Management of Exuberant Granulation Tissue," Veterinary Clinic of North America—Equine Practice, vol. 3, pp. 551–562, (1989). NPL–043.
Byers, R.M., "Clinical effects of closed suction drainage on wound healing in patients with head and neck cancer," Arch. Otolaryngol., vol. 108:723–6, (Nov. 1982). NPL–066.
Cesany, P., "Suction in the Treatment of Torpid Ulcerations," Rozhledy v chirurgii, 48–9, MINC022894–MINC022898, cover sheet and pp. 406–409 English abstract on p. 409 (1 sheet printout from PubMed) (Sep. 1969). NPL–072.
Chinn, S.D., "Closed wound suction drainage," J. Foot Surg., vol. 24: 76–81, (Jan.–Feb. 1985). NPL–083.
Davydov, Y., et al., "Bacteriological and Cytological Assessment of Vacuum Therapy of Purulent Wounds", Vestn. Khir., cover sheet and pp. 48–52, in Russian, English abstract provided on p. 52, (1988), (Exhibit D–172). DV3.
Davydov, Y., et al., "Vacuum Therapy in the Treatment of Purulent Lactation Mastitis," Vestn. Khir. Cover sheet and pp. 66–70, in Russian, English abstract provided on p. 70, (1986), (Exhibit D–173). DV6.
Davydov, Y.A., et al., "Vacuum Therapy in Treatment of Acute Purulent Diseases of Soft Tissues and Purulent Wounds," Vestnik Khirurgili (Surgeon's Herald), Medicine Publishers 1986, 5 sheets, (Exhibit P–528) DV11.
Email dated Jan. 14, 2002 with attachments, including "Report of Meeting with DG Consulting" dated Jan. 10, 2002, 5 sheets, (Exhibit D–157). NPL–137.
Westaby, S., "Treatment of purulent wounds and fistulae with an adhesive wound irrigation device," Annals of the Royal College of Surgeons, vol. 63: 353–6 (1981). NPL–145.
Fox, R., "A rapid screen for drug abuse," The Pharmaceutical Journal, 789, (1988) NPL–165.

Hartz, R.R., et al., "Healing of the Perineal Wound," Arch. Surg., vol. 115, 471–474, (1980), (Exhibit D–395).
Letter dated Jan. 25, 2002 from Charles C. Valauskas to Mr. Richard Weston Regarding: Argenta "Wound Treatment" Patent Evaluation, 15 pages, (Exhibit D–388). NPL–254.
Letter to European Patent Office regarding Observations by a third party pursuant to Art. 115 EPC, 4 sheets, dated Mar. 6, 2006. EPOP1WH1–26.
Letter to Mr. Urs Tanner from Michael Baniak dated Aug. 23, 2004 re: Updated Opinion of Non–infringement and Invalidity of Zamierowski U.S. Patent 4,969,880 and Argenta U.S. Patent 5,636,643 (Exhibit D–140). NPL–255.
Mizuno, K., "Suctioning Sponge," Arch. Opthalmol., vol. 101:294, (Feb. 1983). NPL–294.
Morykwas, Laboratory Notebook pages and charts; 38 pages (Exhibit D–46) dated prior to Mar. 1993 WFU–45.
Morykwas, Laboratory notebook pages and charts, 16 sheets, (Exhibit D–286) dated prior to Mar. 1993 WFU–46.
Morykwas, Laboratory notebook pages and charts, 17 sheets, (Exhibit D–233) dated prior to Nov. 1991 WFU–47.
Morykwas, Laboratory notebook pages of charts, Aug. 29 and Dec. 19, 3 sheets, (Exhibit P–664) dated prior to Nov. 1991 WFU–48.
Nikolov, A., "Method of treatment of postphlebitic and varicose tropic ulcers on the lower extremities by vacuum [Vacuum treatment method in postphlebitic and varicose trophic ulcers of the lower extremities]", Khirurgiia, pp. 368–374, (English abstract on p. 371 and 1 sheet printout from PubMed) (1981) NPL–314.
O'Leary, P., ed., et al., "Techniques for Surgeons," John Wiley & Sons, 3 cover sheets and pp. 417–418, article by Barbara Ann Montgomery, "142: Easy Dressing of Large, Draining Abdominal Wounds Using Moisture Vapor–Premeable Film," (1985). NPL–297.
Opposition EP to 0620720, Communications of Opponent Hartman (Brief in Reply to Patentee's Brief Oct. 15, 1999) dated Mar. 8, 2000 (and English translation). EPOPWH1–04.
Opposition EP to 0620720, Communication of Opponent Hartman (Opening Brief) dated Dec. 16, 1998). EPOPWH1–01.
Opposition EP to 0620720, Communication of Opponent Hartman dated Jul. 19, 2004. EPOPWH1–14.
Opposition EP to 0620720, Communication of Opponent Hartman dated Sep. 20, 2004 with Eng. Translation. EPOPWH1–15.
Opposition EP to 0620720, Communication of Opponent Mondomed dated Dec. 17, 1998. EPOPWH1–02.
Opposition EP to 0620720, Communication of Patentee (Response Brief) dated Oct. 15, 1999. EPOPWH1–03.
Opposition EP to 0620720, Patentee's Grounds of Appeal, dated Sep. 29, 2004, with English translation. EPOPWH1–18.
Opposition EP to 0620720, Preliminary Opinion of Opposition Division dated Aug. 11, 2003 (5 pages), Summons to Oral Proceedings Pursuant to Rule 71(1) EPC Dated Aug. 12, 2003, (6 pages). EPOPWH1–08.
Photographs of wound coverings, 16 sheets. (Exhibit D–240) (allegedly dated 1989). NPL–331.
Slides and photographs, 19 sheets, (Exhibit D–152) (allegedly dated 1987). NPL–376.
Slides, drawings, photographs and presentation slides, 20 sheets, (Exhibit D–151) (allegedly dated 1987). NPL–377.

Smith, S.R., "Surgical drainage," Br. J. Hosp. Med., pp. 308–315, (Jun. 1985). NPL–379.

Svedman, "A dressing system providing fluid supply and suction drainage used for continuous or intermittent irrigation," Ann. Plast. Surg., vol. 17, 9 pages, (Aug. 1986). NPL–389.

Svedman, "Irrigation treatment in split thickness skin grafting of intractable leg ulcers," Scand. J. Plast. Reconstr. Surg., vol. 19.211–213, (1985). NPL–390.

Svedman, "A dressing allowing continuous treatment of a biosurface," IRCS Medical Science: Biomedical Technology; Clinical Medicine; Surgery and Transplantation, 7:221 (1979), with annotations. NPL–388.

Viljanto, J., "Eine neue Methods zur Behandlung offener Wundflachen," ("A new method for treatment of open wounds") Annales Chirugine et Gynaecologia Fennia, 60:94–100, (English abstract on first page and 1 sheet printout from PubMed) (1972). NPL–421.

Yusupov, Yu. N.,. et al., 5 sheets of English translation of "Active Draiage of Wounds", Vestnik khirurgii imeni I.I. Grekova 1987, 138(4), 42–46 (1987), also attached are 3 pages of English translation by BlueSky publishing entitled "Active Wound Drainage" by Usupov and Yupifanov, Vestisik Khirugii, Apr. 42–46 (1987) (1 sheet printout from PubMed). NPL–452.

Morykwas, Laboratory Notebook pages and charts; (D–46) dated prior to Nov. 1991 WFU–49.

Morykwas, Laboratory Notebook pages and charts; (D–286) dated prior to Nov. 1991 WFU–50.

*KCI* v. *BlueSky*, Deposition of Penny Campbell with Exhibits dated Jan. 17, 2005. BS–80.

*KCI* v. *BlueSky*, Transcript of Deposition of Mark Chariker, M.D., with Exhibits, dated Apr. 5, 2006. BS–81.

*KCI* v. *BlueSky*, Transcript of Deposition of Harriet W. Hopf, M.D., with Exhibits, dated Jul. 4, 2006. BS–82.

*KCI* v. *BlueSky*, Deposition transcript with Exhibits of Thomas K. Hunt dated Apr. 21, 2005. BS–83.

*KCI* v. *BlueSky*, Transcript of Deposition of Donna Goudberg Lockhart, with Exhibits, dated Jul. 7, 2006. BS–84.

*KCI* v. *BlueSky*, Transcript of Deposition of Marie Louisse Lachute McGregor, dated Jul. 11, 2006. Bs–85.

*KCI* v. *BlueSky*, Transcript of Deposition of Michael A. O'Neil, with Exhibits, dated Apr. 6, 2006. BS–86.

*KCI* v. *BlueSky*, Transcript of Deposition of Vincent B. Pizziconi, Ph.D., with Exhibits, dated Apr. 7, 2006. BS–87.

*KCI* v. *BlueSky*, Transcript of Deposition of David Tumey, with Exhibits, dated Jun. 15, 2008. BS–88.

*KCI* v. *BlueSky*, Transcript of Deposition of Tianning Xu, with Exhibits, dated Apr. 27, 2006. BS–89.

*KCI* v. *BlueSky*, Videotaped Deposition of Louis C. Argenta, M.D., with Exhibits, Winston–Salem, North Carolina, Friday, Mar. 17, 2006. BS–90.

U.S. Appl. No. 10/647,068—Official Action P02977US1–OA–10 (Jan. 17, 2008).

Meehan, P.A., "Open abdominal wounds: a creative approach to a challenging problem", Progressions, 4(2):3–8, 11 (1992). NPL–276.

N.A. Bagautdinov, "Variant of External Vacuum Aspiration in the Treatment of Purulent Diseases of Soft Tissues," in Current Problems of Modern Clinical Surgery: Interdepartmental Collection, edited by V.Ye Volkov et al. (Chuvashia State University, Cheboksary, U.S.S.R. 1985) pp. 94–96.

G. Živadinović, V. Ðukić, Ž. Maksimović, Ð. Radak and P. Peska, "Vacuum Therapy in the Treatment of Peripheral Blood Vessels," *Timok Medical Journal* 11 (1986) 161–164.

Selections from W. Meyer and V. Schmieden, *Bier's Hyperemic Treament in Surgery, Medicine, and the Specialist: A Manual of Its Practical Application* (W.B. Saunders Co., Philadelpha, PA 1909) pp. 17–25, 44–64, 90–96, 167–170, and 210–211.

W.M. Chardak, D.A., Brueska, A.P. Santomaurio, and G. Fazekas, "Experimental Studies on Synthetic Substitutes for Skin and Their Use in the Treatment of Burns,"*Annals of Surgery* 155 (1962) 127–139.

U.S. Appl. No. 07/792,001, Amendment and Reply under 37 C.F.R. § 1.111, mailed Apr. 29, 1996.

In re U.S. Patent No. 5,645,081, Control No. 90/008,692, Reply and Request for Reconsideration under 37 C.F.R. § 1.111, filed Apr. 28, 2008, in the U.S. Patent and Trademark Office.

*Kinetic Concepts, Inc.* v. *BlueSky Med. Corp.*, No. SA–03–CA–0832, Plaintiffs' Fourth Amended Complaint (W.D. Tex. Jun. 30, 2005) ("Amended Complaint").

*Kinetic Concepts, Inc.* v. *BlueSky Med. Group, Inc.*, Nos. 2007–1340, –1341, –1342, Brief of Appellants, Medela AG and Medela, Inc. (Fed. Cir. May 23, 2007).

*Kinetic Concepts, Inc.* v. *BlueSky Med. Group, Inc.*, Nos. 2007–1340, –1341, –1342, Brief of Kinetic Concepts, Inc., KCI Licensing, Inc., KCI USA, Inc., and Wake Forest University Health Sciences (Fed. Cir. Mar. 3, 2008).

*Kinetic Concepts, Inc.* v. *BlueSky Med. Group, Inc.*, Nos. 2007–1340, –1341, –1342, Reply Brief of Appellants, Medela AG and Medela, Inc. (Fed. Cir. May 16, 2008).

Selections from *Kinetic Concepts, Inc.* v. *BlueSky Med. Corp.*, No. SA–03–CA–0832, in the U.S. District Court for the Western District of Texas.

D.P. Orgill, L.R. Bayer, J. Neuwalder, and R.C. Felter, "Microdeformational Wound Therapy—A New Era in Wound Healing," *Global Surgery: Future Directions in Surgery* (Touch Briefings, London, U.K. 2005) pp. 22–25.

M.J. Morykwas, B.J. Faler, D.J. Pearce, and L.C. Argenta, "Effects of Varying Levels of Subatmospheric Pressure on the Rate of Granulation Tissue Formation in Experimental Wounds in Swine," *Annals of Plastic Surgery* 47 (2001) 457–551.

*V.A.C. Therapy Clinical Guidelines: A Reference Source for Clinicians* (KCI Licensing Inc., San Antonio, TX 2007).

R. Fujimori, M. Hiramoto, and S. Qfuji, "Sponge Fixation Method for Treament of Early Scars," *Plastic & Reconstructive Surgery* 47 (1968) 322–327.

*Kirk–Othmer Encyclopedia of Chemical Technology*, edited by A. Standen (John Wiley & Sons, Inc., $2^{nd}$ ed., vol. 14 1967) p. 227.

Declaration of Dr. Ian L. Gordon, M.D., Ph.D.

Declaration of Dr. Kenneth R. Diller, Sc.D.

\* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–82 is confirmed.

* * * * *